(12) United States Patent
Gouvea et al.

(10) Patent No.: US 11,578,347 B2
(45) Date of Patent: Feb. 14, 2023

(54) ANAEROBIC FERMENTATIVE PRODUCTION OF FURANDIMETHANOL AND ENZYMATIC PRODUCTION OF FURANDICARBOXYLIC ACID

(71) Applicant: Braskem S.A., Camacari (BR)

(72) Inventors: Iuri Estrada Gouvea, Campinas (BR); Ana Karina Brambilla Costa, Campinas (BR); Marcos Rogerio Simoes, Campinas (BR); Veronica Leite Queiroz, Campinas (BR); Aline Silva Romão Dumaresq, Campinas (BR)

(73) Assignee: BRASKEM S.A., Camacari (BR)

( * ) Notice: Subject to any disclaimer, the term of this patent is extended or adjusted under 35 U.S.C. 154(b) by 0 days.

(21) Appl. No.: 17/463,988

(22) Filed: Sep. 1, 2021

(65) Prior Publication Data

US 2022/0064682 A1 Mar. 3, 2022

Related U.S. Application Data

(60) Provisional application No. 63/073,271, filed on Sep. 1, 2020.

(51) Int. Cl.
| | |
|---|---|
| *C12N 9/88* | (2006.01) |
| *C12P 17/04* | (2006.01) |
| *C12N 1/16* | (2006.01) |
| *C12N 15/81* | (2006.01) |
| *C12R 1/865* | (2006.01) |

(52) U.S. Cl.
CPC ............. *C12P 17/04* (2013.01); *C12N 1/165* (2021.05); *C12N 15/81* (2013.01); *C12R 2001/865* (2021.05)

(58) Field of Classification Search
CPC .............. C12P 17/04; C12N 9/16; C12N 9/88
See application file for complete search history.

(56) References Cited

FOREIGN PATENT DOCUMENTS

| WO | 2010015122 A1 | 2/2010 |
| WO | 2014086702 A2 | 6/2014 |

OTHER PUBLICATIONS

Almeida, João R M et al., "NADH- vs NADPH-coupled reduction of 5-hydroxymethyl furfural (HMF) and its implications on product distribution in", Applied Microbiology and Biotechnology, Apr. 1, 2008, vol. 78, No. 6, pp. 939-945, Germany (7 pages).
Laadan, Boaz et al., "Identification of an NADH-dependent 5-hydroxymethylfurfural-reducing alcohol dehydrogenase in Saccharomyces cerevisiae", Yeast, Jan. 1, 2008, vol. 25, No. 3, pp. 191-198,Sweden (8 pages).
Wang, Yu et al., "Industrial production, application, microbial biosynthesis and degradation of furanic compound, hydroxymethylfurfural (HMF)", AIMS Microbiology, Jan. 1, 2018, vol. 4, No. 2, pp. 261-273, USA (13 pages).
Miller, Danielle et al., "Biosynthesis of the 5-(Aminomethyl)-3-furanmethanol Moiety of Methanofuran", Biochemistry, Jul. 10, 2014, vol. 53, No. 28, p. 4635-4647, USA (13 pages).
International Search Report and Written Opinion dated Dec. 6, 2021, for International Application No. PCT/BR2021/050374 filed on Sep. 1, 2021.

*Primary Examiner* — Tekchand Saidha
(74) *Attorney, Agent, or Firm* — Morgan, Lewis & Bockius LLP

(57) ABSTRACT

The present disclosure provides recombinant microorganisms and methods for the anaerobic production of 2,4-furandimethanol from one or more carbon sources. The microorganisms and methods provide redox-balanced and ATP positive pathways for co-producing 2,4-furandimethanol with ethanol and for co-producing 2,4-furandimethanol with ethanol and acetone and/or isopropanol. The method provides recombinant microorganisms that express endogenous and/or exogenous nucleic acid molecules encoding polypeptides that catalyze the conversion of a carbon source into 2,4-furandimethanol and that couple the 2,4-furandimethanol pathway with an additional metabolic pathway. The present disclosure further provides enzymatic production of 2,4-furandicarboxylic acid.

24 Claims, 10 Drawing Sheets

Specification includes a Sequence Listing.

FIG. 5A
| MssI site | GPD1 5' Flank | Zeocin marker | GPD1 3' Flank | MssI site |

FIG. 5B
| MssI site | GPD2 5' Flank | Geneticin marker | GPD2 3' Flank | MssI site |

FIG. 5C
| MssI site | GPD1 5' Flank | pTDH3 | MfnB1 | tTEF1 | Zeocin marker | GPD1 3' Flank | MssI site |

FIG. 5D
| MssI site | GPD2 5' Flank | pTEF1 | MfnB1 | tADH1 | pTPI1 | ADH1mut | tPGK1 | Geneticin marker | GPD2 3' Flank | MssI site |

SEQUENCE LISTING

```
<160> NUMBER OF SEQ ID NOS: 21

<210> SEQ ID NO 1
<211> LENGTH: 531
<212> TYPE: PRT
<213> ORGANISM: Methylovorus sp

<400> SEQUENCE: 1

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
        35                  40                  45

Glu Ile His Asp Gly Leu Arg Pro Trp Leu Pro Arg Leu Ser Gly Asp
    50                  55                  60

Lys Phe Phe Trp Pro Asn Leu Thr Ile His Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Val Ser Asn Arg Gly Leu Pro Arg
            100                 105                 110

Asp Tyr Asp Glu Trp Gln Ala Leu Gly Ala Asp Gly Trp Asp Trp Gln
        115                 120                 125

Gly Val Leu Pro Tyr Phe Ile Lys Thr Glu Arg Asp Ala Asp Tyr Gly
    130                 135                 140

Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
                165                 170                 175

Glu Ala Ala Gly Leu Pro Asn Ile His Asp Gln Asn Ala Arg Phe Asp
```

```
                180                 185                 190
Asp Gly Tyr Phe Pro Ala Phe Thr Leu Lys Gly Glu Glu Arg Phe
            195                 200                 205

Ser Ala Ala Arg Gly Tyr Leu Asp Ala Ser Val Arg Val Arg Pro Asn
        210                 215                 220

Leu Ser Leu Trp Thr Glu Ser Arg Val Leu Lys Leu Leu Thr Thr Gly
225                 230                 235                 240

Asn Ala Ile Thr Gly Val Ser Val Leu Arg Gly Arg Glu Thr Leu Gln
                245                 250                 255

Val Gln Ala Arg Glu Val Ile Leu Thr Ala Gly Ala Leu Gln Ser Pro
            260                 265                 270

Ala Ile Leu Leu Arg Thr Gly Ile Gly Pro Ala Ala Asp Leu His Ala
        275                 280                 285

Leu Gly Ile Pro Val Leu Ala Asp Arg Pro Gly Val Gly Arg Asn Leu
    290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
                325                 330                 335

Ile Arg Ala Ser Ser Gly Val Asp Pro Ala Thr Pro Ser Asp Leu Phe
            340                 345                 350

Leu His Ile Gly Ala Asp Pro Val Ser Gly Leu Ala Ser Ala Val Phe
        355                 360                 365

Trp Val Asn Lys Pro Ser Ser Thr Gly Trp Leu Lys Leu Lys Asp Ala
    370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Thr His Tyr
                405                 410                 415

Phe Ala Ala Pro Ser Leu Ala Lys Tyr Gly Leu Ala Leu Ala Leu Ser
            420                 425                 430

Arg Phe Ala Ala Pro Gln Pro Gly Gly Pro Leu Leu Asn Asp Leu Leu
        435                 440                 445

Gln Asp Glu Ala Ala Leu Glu Arg Tyr Leu Arg Thr Asn Val Gly Gly
    450                 455                 460

Val Trp His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                485                 490                 495

Arg Val Ala Asp Ala Ser Ile Met Pro Thr Val Pro Thr Ala Asn Thr
            500                 505                 510

Asn Leu Pro Thr Leu Met Leu Ala Glu Lys Ile Ala Asp Ala Ile Leu
        515                 520                 525

Thr Gln Ala
    530

<210> SEQ ID NO 2
<211> LENGTH: 579
<212> TYPE: PRT
<213> ORGANISM: Cupriavidus basilensis

<400> SEQUENCE: 2

Met Asp Thr Pro Arg Glu Arg Phe Asp Tyr Val Ile Val Gly Gly Gly
1               5                   10                  15
```

```
Ser Ala Gly Cys Val Leu Ala Asn Arg Leu Ser Gln Asp Pro Ala Ile
            20                  25                  30

Arg Val Ala Leu Ile Glu Ala Gly Val Asp Thr Pro Pro Asp Ala Val
            35                  40                  45

Pro Ala Glu Ile Leu Asp Ser Tyr Pro Met Pro Leu Phe Phe Gly Asp
 50                  55                  60

Arg Tyr Ile Trp Pro Ser Leu Gln Ala Arg Ala Val Ala Gly Gly Arg
 65                  70                  75                  80

Ser Lys Val Tyr Glu Gln Gly Arg Val Met Gly Gly Ser Ser Ile
                85                  90                  95

Asn Val Gln Ala Ala Asn Arg Gly Leu Pro Arg Asp Tyr Asp Glu Trp
            100                 105                 110

Ala Ala Ser Gly Ala Ser Gly Trp Ser Trp Gln Asp Val Leu Pro Tyr
            115                 120                 125

Phe Arg His Leu Glu Arg Asp Val Asp Tyr Gly Asn Ser Pro Leu His
            130                 135                 140

Gly Ser His Gly Pro Val Pro Ile Arg Arg Ile Leu Pro Gln Ala Trp
145                 150                 155                 160

Pro Pro Phe Cys Thr Glu Phe Ala His Ala Met Gly Arg Ser Gly Leu
                165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
            195                 200                 205

Tyr Leu Asp Ala Asp Thr Arg Arg Ala Asn Leu Arg Ile Tyr Ala
210                 215                 220

Glu Thr Thr Val Arg Lys Leu Val Val Ser Gly Arg Glu Ala Arg Gly
225                 230                 235                 240

Val Ile Ala Met Arg Ala Asp Gly Ser Arg Leu Ala Leu Asp Ala Gly
                245                 250                 255

Glu Val Ile Val Ser Ala Gly Ala Leu Gln Ser Pro Ala Ile Leu Met
            260                 265                 270

Arg Ala Gly Ile Gly Asp Ala Gly Ala Leu Gln Ala Leu Gly Ile Glu
            275                 280                 285

Val Val Ala Asp Arg Pro Gly Val Gly Arg Asn Leu Gln Asp His Pro
290                 295                 300

Ala Leu Thr Phe Cys Gln Phe Leu Ala Pro Gln Tyr Arg Met Pro Leu
305                 310                 315                 320

Ser Arg Arg Arg Ala Ser Met Thr Ala Ala Arg Phe Ser Ser Gly Val
                325                 330                 335

Pro Gly Gly Glu Ala Ser Asp Met Tyr Leu Ser Ser Ser Thr Arg Ala
            340                 345                 350

Gly Trp His Ala Leu Gly Asn Arg Leu Gly Leu Phe Phe Leu Trp Cys
            355                 360                 365

Asn Arg Pro Phe Ser Arg Gly Gln Val Ser Leu Ala Gly Ala Gln Pro
370                 375                 380

Asp Val Pro Pro Met Val Glu Leu Asn Leu Leu Asp Asp Glu Arg Asp
385                 390                 395                 400

Leu Arg Arg Met Val Ala Gly Val Arg Lys Leu Val Gln Ile Val Gly
                405                 410                 415

Ala Ser Ala Leu His Gln His Pro Gly Asp Phe Phe Pro Ala Thr Phe
            420                 425                 430

Ser Pro Arg Val Lys Ala Leu Ser Arg Val Ser Arg Gly Asn Val Leu
```

```
                435                 440                 445
Leu Thr Glu Leu Leu Gly Ala Val Leu Asp Val Ser Gly Pro Leu Arg
    450                 455                 460

Arg Ser Leu Ile Ala Arg Phe Val Thr Gly Gly Ala Asn Leu Ala Ser
465                 470                 475                 480

Leu Leu Thr Asp Glu Ser Ala Leu Glu Gly Phe Val Arg Gln Ser Val
            485                 490                 495

Phe Gly Val Trp His Ala Ser Gly Thr Cys Arg Met Gly Ala His Ala
                500                 505                 510

Asp Arg Ser Ala Val Thr Asp Ala Ala Gly Arg Val His Asp Val Gly
            515                 520                 525

Arg Leu Arg Val Ile Asp Ala Ser Leu Met Pro Arg Leu Pro Thr Ala
        530                 535                 540

Asn Thr Asn Ile Pro Thr Ile Met Leu Ala Glu Lys Ile Ala Asp Thr
545                 550                 555                 560

Met Gln Ala Glu Arg Arg Ala Val Arg Pro Ala Ser Ser Glu Val Ala
                565                 570                 575

His Pro Ser

<210> SEQ ID NO 3
<211> LENGTH: 579
<212> TYPE: PRT
<213> ORGANISM: Cupriavidus necator

<400> SEQUENCE: 3

Met Asp Thr Pro Arg Glu Arg Phe Asp Tyr Val Ile Val Gly Gly Gly
1               5                   10                  15

Ser Ala Gly Cys Val Leu Ala Asn Arg Leu Ser Gln Asp Pro Ala Ile
                20                  25                  30

Arg Val Ala Leu Ile Glu Gly Gly Val Asp Thr Pro Pro Asp Ala Val
            35                  40                  45

Pro Val Glu Ile Leu Asp Ser Tyr Pro Met Pro Leu Phe Phe Gly Asp
        50                  55                  60

Arg Tyr Ile Trp Pro Ser Leu Gln Ala Arg Ala Val Ala Gly Gly Arg
65                  70                  75                  80

Ser Lys Val Tyr Glu Gln Gly Arg Val Met Gly Gly Ser Ser Ser Ile
                85                  90                  95

Asn Val Gln Ala Ala Asn Arg Gly Leu Pro Arg Asp Tyr Asp Glu Trp
            100                 105                 110

Ala Ala Ser Gly Ala Pro Gly Trp Ser Trp Gln Asp Val Leu Pro Tyr
        115                 120                 125

Phe Arg Asn Leu Glu Arg Asp Val Asp Tyr Gly Asn Ser Pro Leu His
    130                 135                 140

Gly Ser His Gly Pro Val Pro Ile Arg Arg Ile Leu Pro Gln Ala Trp
145                 150                 155                 160

Pro Pro Phe Cys Thr Glu Phe Ala His Ala Met Gly Leu Ser Gly Leu
                165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
        195                 200                 205

Tyr Leu Asp Ala Asp Thr Arg Arg Ala Asn Leu Arg Ile Tyr Ala
    210                 215                 220

Glu Thr Thr Val Arg Lys Leu Val Val Ser Gly Arg Glu Ala Arg Gly
```

```
            225                 230                 235                 240
    Val Ile Ala Ile Arg Ala Asp Gly Ser Arg Leu Ala Leu Asp Ala Gly
                        245                 250                 255

Glu Val Ile Val Ser Ala Gly Ala Leu Gln Ser Pro Ala Ile Leu Met
                        260                 265                 270

Arg Ala Gly Ile Gly Asp Ala Gly Leu Gln Ala Leu Gly Ile Glu
                        275                 280                 285

Val Val Ala Asp Arg Pro Gly Val Gly Arg Asn Leu Gln Asp His Pro
                        290                 295                 300

Ala Leu Thr Phe Cys Gln Phe Leu Ala Pro Gln Tyr Arg Met Pro Leu
    305                 310                 315                 320

Ser Arg Arg Arg Ala Ser Met Thr Ala Ala Arg Phe Ser Ser Gly Val
                        325                 330                 335

Pro Gly Gly Glu Ala Ser Asp Met Tyr Leu Ser Ser Thr Arg Ala
                        340                 345                 350

Gly Trp His Ala Leu Gly Asn Arg Leu Gly Leu Phe Phe Leu Trp Cys
                        355                 360                 365

Asn Arg Pro Phe Ser Arg Gly Gln Val Ser Leu Ala Gly Ala Gln Pro
    370                 375                 380

Asp Val Pro Pro Met Val Glu Leu Asn Leu Leu Asp Asp Glu Arg Asp
    385                 390                 395                 400

Leu Arg Arg Met Val Ala Gly Val Arg Lys Leu Val Gln Ile Val Gly
                        405                 410                 415

Ala Ser Ala Leu His Gln His Pro Gly Asp Phe Phe Pro Ala Thr Phe
                        420                 425                 430

Ser Pro Arg Val Lys Ala Leu Ser Arg Leu Ser Arg Gly Asn Ala Leu
                        435                 440                 445

Leu Thr Glu Leu Leu Gly Ala Leu Leu Asp Val Ser Gly Pro Leu Arg
                        450                 455                 460

Arg Ser Leu Ile Ala Arg Phe Val Thr Gly Gly Ala Asn Leu Ala Ser
    465                 470                 475                 480

Leu Leu Val Glu Glu Ser Ala Leu Glu Gly Phe Val Arg Gln Ser Val
                        485                 490                 495

Phe Gly Val Trp His Ala Ser Gly Thr Cys Arg Met Gly Ala His Ala
                        500                 505                 510

Asp Arg Ser Ala Val Thr Asp Ala Ala Gly Arg Val His Asp Val Gly
                        515                 520                 525

Arg Leu Arg Val Val Asp Ala Ser Leu Met Pro Arg Leu Pro Thr Ala
                        530                 535                 540

Asn Thr Asn Ile Pro Thr Ile Met Leu Ala Glu Lys Ile Ala Asp Thr
    545                 550                 555                 560

Met Gln Ala Glu Arg Arg Ala Val Arg Leu Ala Ser Ser Glu Val Ala
                        565                 570                 575

His Gln Ser

<210> SEQ ID NO 4
<211> LENGTH: 579
<212> TYPE: PRT
<213> ORGANISM: Cupriavidus pinatubonensis

<400> SEQUENCE: 4

Met Gly Thr Pro Arg Asp Arg Phe Asp Tyr Val Ile Val Gly Gly Gly
1               5                   10                  15

Ser Ala Gly Cys Val Leu Ala Asn Arg Leu Ser Arg Asp Pro Gly Ile
```

```
                     20                  25                  30
Arg Val Ala Leu Ile Glu Gly Gly Val Asp Thr Pro Pro Gly Ala Val
             35                  40                  45
Pro Ala Glu Ile Leu Asp Ser Tyr Pro Met Pro Leu Phe Phe Gly Asp
             50                  55                  60
Arg Tyr Leu Trp Pro Ser Leu Gln Ala Arg Val Ala Gly Gly Arg
 65                  70                  75                  80
Ala Arg Leu Tyr Glu Gln Gly Arg Val Met Gly Gly Ser Ser Ile
                     85                  90                  95
Asn Val Gln Ala Ala Asn Arg Gly Leu Pro Arg Asp Tyr Asp Glu Trp
             100                 105                 110
Ala Ala Ser Gly Ala Pro Gly Trp Ser Trp Gln Glu Val Leu Pro Tyr
             115                 120                 125
Phe Arg Lys Leu Glu Arg Asp Val Asp Phe Ala Ser Ser Pro Met His
             130                 135                 140
Gly Ser Asp Gly Pro Val Pro Ile Arg Arg Ile Leu Pro Pro Ala Trp
145                 150                 155                 160
Pro Pro Phe Cys Thr Ala Phe Ala Gln Ala Met Gly Arg Ser Gly Leu
                 165                 170                 175
Ser Ala Leu Asp Asp Gln Asn Ala Glu Phe Gly Asp Gly Trp Phe Pro
             180                 185                 190
Ala Ala Phe Ser Asn Leu Asp Gly Lys Arg Val Ser Thr Ala Ile Ala
             195                 200                 205
Tyr Leu Asp Ala Asn Thr Arg Lys Arg Thr Asn Leu Arg Ile Phe Ala
             210                 215                 220
Glu Thr Thr Val Lys Glu Leu Val Val Ser Gly Arg Glu Ala Arg Gly
225                 230                 235                 240
Val Ile Ala Val Arg Ala Asp Gly Ala Arg Leu Ala Leu Glu Ala Ala
                 245                 250                 255
Glu Val Ile Val Ser Ala Gly Ala Leu Gln Ser Pro Ala Ile Leu Met
             260                 265                 270
Arg Ala Gly Ile Gly Asp Ala Ala Leu Gln Ala Leu Gly Ile Glu
             275                 280                 285
Val Val Ala Asp Arg Pro Gly Val Gly Arg Asn Leu Gln Asp His Pro
             290                 295                 300
Ala Leu Thr Phe Cys Gln Phe Leu Ala Pro Glu Tyr Arg Met Pro Leu
305                 310                 315                 320
Ala Arg Arg Arg Ser Ser Met Thr Ala Ala Arg Phe Ser Ser Glu Val
                 325                 330                 335
Pro Gly Gly Glu Ala Ser Asp Met Tyr Leu Ser Ser Ser Thr Arg Ala
             340                 345                 350
Gly Trp His Ala Leu Gly Asn Arg Leu Gly Leu Phe Phe Leu Trp Cys
             355                 360                 365
Asn Arg Pro Phe Ser Arg Gly Gln Val Ser Leu Ala Gly Ala Gln Pro
             370                 375                 380
Glu Val Ser Pro Leu Val Glu Leu Asn Leu Leu Asp Asp Glu Arg Asp
385                 390                 395                 400
Leu Arg Arg Met Val Ala Gly Val Arg Arg Leu Val Arg Ile Val Gly
                 405                 410                 415
Ala Ser Ala Leu His Gln His Pro Asp Asp Phe Phe Pro Ala Ile Phe
             420                 425                 430
Ser Pro Arg Val Lys Ala Met Ser Arg Val Ser Pro Gly Asn Ala Leu
             435                 440                 445
```

```
Leu Thr Ala Leu Leu Gly Ala Leu Leu Asp Val Ser Gly Pro Leu Arg
    450                 455                 460

Arg Ser Leu Ile Ala Arg Phe Val Thr Gly Gly Ala Asn Leu Ala Ser
465                 470                 475                 480

Leu Leu Ala Asp Glu Ser Ala Leu Glu Gly Phe Val Arg Gln Ser Val
                485                 490                 495

Phe Gly Val Trp His Ala Ser Gly Thr Cys Arg Met Gly Ala His Ala
                500                 505                 510

Asp Arg Ser Ala Val Thr Asp Thr Thr Gly Arg Val His Asp Val Gly
                515                 520                 525

Arg Leu Arg Val Val Asp Ala Ser Leu Met Pro Arg Leu Pro Thr Ala
            530                 535                 540

Asn Thr Asn Ile Pro Thr Ile Met Leu Ala Glu Lys Ile Ala Asp Ala
545                 550                 555                 560

Met Leu Ala Glu Arg Arg Ala Thr Arg Arg Ala Leu Ser Glu Val Ala
                565                 570                 575

Asp Pro Gly

<210> SEQ ID NO 5
<211> LENGTH: 591
<212> TYPE: PRT
<213> ORGANISM: Pandoraea sp. B-6

<400> SEQUENCE: 5

Met Pro Arg Gly His Ala His Arg Arg Ile Arg Arg His Ser Val Gln
1               5                   10                  15

Asn Val Arg Glu Arg Phe Asp Tyr Val Ile Ile Gly Gly Gly Ser Ala
                20                  25                  30

Gly Cys Val Leu Ala His Arg Leu Ser Ala Asn Arg Glu Leu Arg Val
            35                  40                  45

Ala Leu Ile Glu Ala Gly Ser Asp Thr Pro Pro Gly Ala Ile Pro Ala
50                  55                  60

Glu Ile Leu Asp Ser Tyr Pro Met Pro Val Phe Cys Gly Asp Arg Tyr
65                  70                  75                  80

Ile Trp Pro Glu Leu Lys Ala Lys Ala Thr Ala Ala Ser Pro Leu Lys
                85                  90                  95

Val Tyr Glu Gln Gly Lys Val Met Gly Gly Gly Ser Ser Ile Asn Val
                100                 105                 110

Gln Ala Ala Asn Arg Gly Leu Pro Arg Asp Tyr Asp Asp Trp Ala Glu
            115                 120                 125

Gln Gly Ala Ser Gly Trp Ala Trp Lys Asp Val Leu Pro Tyr Phe Arg
130                 135                 140

Lys Leu Glu Arg Asp Ala Asp Tyr Gly Gly Ser Ala Leu His Gly Ala
145                 150                 155                 160

Asp Gly Pro Val Ala Ile Arg Arg Ile Lys Pro Asp Ala Trp Pro Arg
                165                 170                 175

Phe Cys His Ala Phe Ala Glu Gly Leu Gln Arg Asn Gly Leu Pro Met
            180                 185                 190

Leu Glu Asp Gln Asn Ala Glu Phe Gly Asp Gly Met Phe Pro Ala Ala
        195                 200                 205

Phe Ser Asn Leu Asp Asp Lys Arg Val Ser Thr Ala Val Ala Tyr Leu
    210                 215                 220

Asp Ala Ala Thr Arg Ala Arg Thr Asn Leu Arg Ile Tyr Ser Asn Thr
225                 230                 235                 240
```

Thr Val Glu Arg Leu Ile Val Thr Gly Gln Arg Ala His Gly Val Val
            245                 250                 255

Ala Met Ser Ala Gly Gly Glu Arg Leu Gln Ile Asp Ala Ala Glu Val
            260                 265                 270

Ile Val Ser Ala Gly Ala Leu Gln Ser Pro Ala Leu Leu Leu Arg Ala
            275                 280                 285

Gly Ile Gly Ala Gly Ser Glu Leu Gln Ala Leu Gly Ile Pro Val Val
            290                 295                 300

Ala Asp Arg Pro Gly Val Gly Arg Asn Leu Gln Asp His Pro Ser Leu
305                 310                 315                 320

Thr Phe Cys His Phe Leu Asp Pro Glu Phe Arg Met Pro Leu Ser Arg
            325                 330                 335

Arg Arg Ala Ser Met Thr Ala Ala Arg Phe Ser Ser Gly Leu Asp Gly
            340                 345                 350

Cys Asp Asn Ala Asp Met Tyr Leu Ser Ser Ala Thr Arg Ala Ala Trp
            355                 360                 365

His Ala Leu Gly Asn Arg Leu Gly Leu Phe Phe Leu Trp Cys Asn Arg
            370                 375                 380

Pro Phe Ser Arg Gly Arg Val Gln Leu Thr Ser Ala Asp Pro Phe Thr
385                 390                 395                 400

Pro Pro Arg Val Asp Leu Asn Leu Leu Asp Asp Glu Arg Asp Ala Arg
            405                 410                 415

Arg Met Ala Ile Gly Val Arg Val Ala Gln Ile Val Gln Gln Thr
            420                 425                 430

Ala Leu His Arg His Pro Asp Asp Phe Pro Ala Ala Phe Ser Pro
            435                 440                 445

Arg Val Lys Ala Leu Ser Arg Phe Ser Ala Gly Asn Ala Ala Leu Thr
            450                 455                 460

Lys Val Leu Gly Leu Ala Leu Asp Thr Pro Ala Pro Leu Arg Arg Trp
465                 470                 475                 480

Ile Ile Asp Thr Phe Val Thr Gly Gly Ile Arg Met Ser Ala Leu Leu
            485                 490                 495

Ala Asp Asp Lys Glu Leu Asp Ala Phe Ile Arg Lys Tyr Val Phe Gly
            500                 505                 510

Val Trp His Ala Ser Gly Thr Cys Arg Met Gly Pro Ala Ser Asp Arg
            515                 520                 525

Met Ala Val Thr Asn Gln Glu Gly Leu Val His Asp Val Ala Asn Leu
            530                 535                 540

Arg Val Val Asp Ala Ser Leu Met Pro Lys Leu Pro Ser Ala Asn Thr
545                 550                 555                 560

Asn Ile Pro Thr Ile Met Met Ala Glu Lys Ile Ala Asp Ala Ile Leu
            565                 570                 575

Ala Arg Arg Lys Ala Pro Pro Gly Val Leu Val Ser Ser Glu Ala
            580                 585                 590

<210> SEQ ID NO 6
<211> LENGTH: 531
<212> TYPE: PRT
<213> ORGANISM: Methylovorus sp

<400> SEQUENCE: 6

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val

```
                    20                  25                  30
Leu Leu Ile Glu Ala Gly Ile Asp Thr Pro Glu Asn Asn Ile Pro Pro
            35                  40                  45
Glu Ile His Asp Gly Leu Arg Pro Trp Leu Pro Arg Leu Ser Gly Asp
        50                  55                  60
Lys Phe Phe Trp Pro Asn Leu Thr Ile His Arg Ala Ala Glu His Pro
65                  70                  75                  80
Gly Ile Thr Arg Glu Pro Gln Phe Tyr Glu Gln Gly Arg Leu Leu Gly
                85                  90                  95
Gly Gly Ser Ser Val Asn Met Val Val Ser Asn Arg Gly Leu Pro Arg
            100                 105                 110
Asp Tyr Asp Glu Trp Gln Ala Leu Gly Ala Asp Gly Trp Asp Trp Gln
        115                 120                 125
Gly Val Leu Pro Tyr Phe Ile Lys Thr Glu Arg Asp Ala Asp Tyr Gly
        130                 135                 140
Asp Asp Pro Leu His Gly Asn Ala Gly Pro Ile Pro Ile Gly Arg Val
145                 150                 155                 160
Asp Ser Arg His Trp Ser Asp Phe Thr Val Ala Ala Thr Gln Ala Leu
                165                 170                 175
Glu Ala Ala Gly Leu Pro Asn Ile His Asp Gln Asn Ala Arg Phe Asp
            180                 185                 190
Asp Gly Tyr Phe Pro Pro Ala Phe Thr Leu Lys Gly Glu Glu Arg Phe
        195                 200                 205
Ser Ala Ala Arg Gly Tyr Leu Asp Ala Ser Val Arg Val Arg Pro Asn
        210                 215                 220
Leu Ser Leu Trp Thr Glu Ser Arg Val Leu Lys Leu Leu Thr Thr Gly
225                 230                 235                 240
Asn Ala Ile Thr Gly Val Ser Val Leu Arg Gly Arg Glu Thr Leu Gln
                245                 250                 255
Val Gln Ala Arg Glu Val Ile Leu Thr Ala Gly Ala Leu Gln Ser Pro
            260                 265                 270
Ala Ile Leu Leu Arg Thr Gly Ile Gly Pro Ala Ala Asp Leu His Ala
        275                 280                 285
Leu Gly Ile Pro Val Leu Ala Asp Arg Pro Gly Val Gly Arg Asn Leu
        290                 295                 300
Trp Glu His Ser Ser Ile Gly Val Val Ala Pro Leu Thr Glu Gln Ala
305                 310                 315                 320
Arg Ala Asp Ala Ser Thr Gly Lys Ala Gly Ser Arg His Gln Leu Gly
                325                 330                 335
Ile Arg Ala Ser Ser Gly Val Asp Pro Ala Thr Pro Ser Asp Leu Phe
            340                 345                 350
Leu His Ile Gly Ala Asp Pro Val Ser Gly Leu Ala Ser Ala Arg Phe
        355                 360                 365
Trp Val Asn Lys Pro Ser Ser Thr Gly Trp Leu Lys Leu Lys Asp Ala
        370                 375                 380
Asp Pro Phe Ser Tyr Pro Asp Val Asp Phe Asn Leu Leu Ser Asp Pro
385                 390                 395                 400
Arg Asp Leu Gly Arg Leu Lys Ala Gly Leu Arg Leu Ile Thr His Tyr
                405                 410                 415
Phe Ala Ala Pro Ser Leu Ala Lys Tyr Gly Leu Ala Leu Ala Leu Ser
            420                 425                 430
Arg Phe Ala Ala Pro Gln Pro Gly Gly Pro Leu Leu Asn Asp Leu Leu
        435                 440                 445
```

```
Gln Asp Glu Ala Ala Leu Glu Arg Tyr Leu Arg Thr Asn Val Gly Gly
    450                 455                 460

Val Phe His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                485                 490                 495

Arg Val Ala Asp Ala Ser Ile Met Pro Thr Val Pro Thr Ala Asn Thr
            500                 505                 510

Asn Leu Pro Thr Leu Met Leu Ala Glu Lys Ile Ala Asp Ala Ile Leu
        515                 520                 525

Thr Gln Ala
    530

<210> SEQ ID NO 7
<211> LENGTH: 531
<212> TYPE: PRT
<213> ORGANISM: Methylovorus sp MUT

<400> SEQUENCE: 7

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
        35                  40                  45

Glu Ile His Asp Gly Leu Arg Pro Trp Leu Pro Arg Leu Ser Gly Asp
    50                  55                  60

Lys Phe Phe Trp Pro Asn Leu Thr Val Tyr Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Val Ser Asn Arg Gly Leu Pro Arg
            100                 105                 110

Asp Tyr Asp Glu Trp Gln Ala Leu Gly Ala Asp Gly Trp Asp Trp Gln
        115                 120                 125

Gly Val Leu Pro Tyr Phe Ile Lys Thr Glu Arg Asp Ala Asp Tyr Gly
    130                 135                 140

Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
                165                 170                 175

Glu Ala Ala Gly Leu Pro Asn Ile His Asp Gln Asn Ala Arg Phe Asp
            180                 185                 190

Asp Gly Tyr Phe Pro Pro Ala Phe Thr Leu Lys Gly Glu Glu Arg Phe
        195                 200                 205

Ser Ala Ala Arg Gly Tyr Leu Asp Ala Ser Val Arg Val Arg Pro Asn
    210                 215                 220

Leu Ser Leu Trp Thr Glu Ser Arg Val Leu Lys Leu Leu Thr Thr Gly
225                 230                 235                 240

Asn Ala Ile Thr Gly Val Ser Val Leu Arg Gly Arg Glu Thr Leu Gln
                245                 250                 255

Val Gln Ala Arg Glu Val Ile Leu Thr Ala Gly Ala Leu Gln Ser Pro
            260                 265                 270

Ala Ile Leu Leu Arg Thr Gly Ile Gly Pro Ala Ala Asp Leu His Ala
```

```
            275                 280                 285
Leu Gly Ile Pro Val Leu Ala Asp Arg Pro Val Gly Arg Asn Leu
    290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
                    325                 330                 335

Ile Arg Ala Ser Ser Gly Val Asp Pro Ala Thr Pro Ser Asp Leu Phe
                340                 345                 350

Leu His Ile His Ala Asp Pro Val Ser Gly Leu Ala Ser Ala Arg Phe
            355                 360                 365

Trp Val Asn Lys Pro Ser Ser Thr Gly Trp Leu Lys Leu Lys Asp Ala
370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Lys His Tyr
                    405                 410                 415

Phe Ala Tyr Pro Ser Leu Ala Lys Tyr Gly Leu Ala Leu Ala Leu Ser
                420                 425                 430

Arg Phe Glu Ala Pro Gln Pro Gly Pro Leu Leu Asn Asp Leu Leu
            435                 440                 445

Gln Asp Glu Ala Ala Leu Glu Arg Tyr Leu Arg Thr Asn Val Gly Gly
        450                 455                 460

Val Phe His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
                    485                 490                 495

Arg Val Ala Asp Ala Ser Ile Met Pro Thr Val Pro Thr Ala Asn Thr
                500                 505                 510

Asn Leu Pro Thr Leu Met Leu Ala Glu Lys Ile Ala Asp Ala Ile Leu
            515                 520                 525

Thr Gln Ala
    530

<210> SEQ ID NO 8
<211> LENGTH: 593
<212> TYPE: PRT
<213> ORGANISM: Pleurotus eryngii

<400> SEQUENCE: 8

Met Ser Phe Gly Ala Leu Arg Gln Leu Leu Ile Ala Cys Leu Ala
1               5                   10                  15

Leu Pro Ser Leu Ala Ala Thr Asn Leu Pro Thr Ala Asp Phe Asp Tyr
                20                  25                  30

Val Val Val Gly Ala Gly Asn Ala Gly Asn Val Val Ala Ala Arg Leu
            35                  40                  45

Thr Glu Asp Pro Asp Val Ser Val Leu Val Leu Glu Ala Gly Val Ser
        50                  55                  60

Asp Glu Asn Val Leu Gly Ala Glu Ala Pro Leu Leu Ala Pro Gly Leu
65                  70                  75                  80

Val Pro Asn Ser Ile Phe Asp Trp Asn Tyr Thr Thr Ala Gln Ala
                85                  90                  95

Gly Tyr Asn Gly Arg Ser Ile Ala Tyr Pro Arg Gly Arg Met Leu Gly
            100                 105                 110
```

```
Gly Ser Ser Ser Val His Tyr Met Val Met Arg Gly Ser Thr Glu
            115                 120                 125

Asp Phe Asp Arg Tyr Ala Ala Val Thr Gly Asp Glu Gly Trp Asn Trp
130                 135                 140

Asp Asn Ile Gln Gln Phe Val Arg Lys Asn Glu Met Val Val Pro Pro
145                 150                 155                 160

Ala Asp Asn His Asn Thr Ser Gly Glu Phe Ile Pro Ala Val His Gly
                165                 170                 175

Thr Asn Gly Ser Val Ser Ile Ser Leu Pro Gly Phe Pro Thr Pro Leu
            180                 185                 190

Asp Asp Arg Val Leu Ala Thr Thr Gln Glu Gln Ser Glu Glu Phe Phe
            195                 200                 205

Phe Asn Pro Asp Met Gly Thr Gly His Pro Leu Gly Ile Ser Trp Ser
210                 215                 220

Ile Ala Ser Val Gly Asn Gly Gln Arg Ser Ser Ser Thr Ala Tyr
225                 230                 235                 240

Leu Arg Pro Ala Gln Ser Arg Pro Asn Leu Ser Val Leu Ile Asn Ala
                245                 250                 255

Gln Val Thr Lys Leu Val Asn Ser Gly Thr Thr Asn Gly Leu Pro Ala
            260                 265                 270

Phe Arg Cys Val Glu Tyr Ala Glu Gln Glu Gly Ala Pro Thr Thr Thr
            275                 280                 285

Val Cys Ala Lys Lys Glu Val Val Leu Ser Ala Gly Ser Val Gly Thr
            290                 295                 300

Pro Ile Leu Leu Gln Leu Ser Gly Ile Gly Asp Glu Asn Asp Leu Ser
305                 310                 315                 320

Ser Val Gly Ile Asp Thr Ile Val Asn Asn Pro Ser Val Gly Arg Asn
                325                 330                 335

Leu Ser Asp His Leu Leu Pro Ala Ala Phe Val Asn Ser Asn
                340                 345                 350

Gln Thr Phe Asp Asn Ile Phe Arg Asp Ser Ser Glu Phe Asn Val Asp
            355                 360                 365

Leu Asp Gln Trp Thr Asn Thr Arg Thr Gly Pro Leu Thr Ala Leu Ile
370                 375                 380

Ala Asn His Leu Ala Trp Leu Arg Leu Pro Ser Asn Ser Ser Ile Phe
385                 390                 395                 400

Gln Thr Phe Pro Asp Pro Ala Ala Gly Pro Asn Ser Ala His Trp Glu
            405                 410                 415

Thr Ile Phe Ser Asn Gln Trp Phe His Pro Ala Ile Pro Arg Pro Asp
            420                 425                 430

Thr Gly Ser Phe Met Ser Val Thr Asn Ala Leu Ile Ser Pro Val Ala
            435                 440                 445

Arg Gly Asp Ile Lys Leu Ala Thr Ser Asn Pro Phe Asp Lys Pro Leu
450                 455                 460

Ile Asn Pro Gln Tyr Leu Ser Thr Glu Phe Asp Ile Phe Thr Met Ile
465                 470                 475                 480

Gln Ala Val Lys Ser Asn Leu Arg Phe Leu Ser Gly Gln Ala Trp Ala
                485                 490                 495

Asp Phe Val Ile Arg Pro Phe Asp Pro Arg Leu Arg Pro Thr Asp
            500                 505                 510

Asp Ala Ala Ile Glu Ser Tyr Ile Arg Asp Asn Ala Asn Thr Ile Phe
            515                 520                 525

His Pro Val Gly Thr Ala Ser Met Ser Pro Arg Gly Ala Ser Trp Gly
```

```
                530                 535                 540
Val Val Asp Pro Asp Leu Lys Val Lys Gly Val Asp Gly Leu Arg Ile
545                 550                 555                 560

Val Asp Gly Ser Ile Leu Pro Phe Ala Pro Asn Ala His Thr Gln Gly
                565                 570                 575

Pro Ile Tyr Leu Val Gly Lys Gln Gly Ala Asp Leu Ile Lys Ala Asp
                580                 585                 590

Gln

<210> SEQ ID NO 9
<211> LENGTH: 593
<212> TYPE: PRT
<213> ORGANISM: Pleurotus eryngii MUT1

<400> SEQUENCE: 9

Met Ser Phe Gly Ala Leu Arg Gln Leu Leu Ile Ala Cys Leu Ala
1               5                   10                  15

Leu Pro Ser Leu Ala Ala Thr Asn Leu Pro Thr Ala Asp Phe Asp Tyr
                20                  25                  30

Val Val Val Gly Ala Gly Asn Ala Gly Asn Val Val Ala Ala Arg Leu
                35                  40                  45

Thr Glu Asp Pro Asp Val Ser Val Leu Val Leu Glu Ala Gly Val Ser
50                  55                  60

Asp Glu Asn Val Leu Gly Ala Glu Ala Pro Leu Leu Ala Pro Gly Leu
65                  70                  75                  80

Val Pro Asn Ser Ile Phe Asp Trp Asn Tyr Thr Thr Thr Ala Gln Ala
                85                  90                  95

Gly Tyr Asn Gly Arg Ser Ile Ala Tyr Pro Arg Gly Arg Met Leu Gly
                100                 105                 110

Gly Ser Ser Ser Val His Tyr Met Val Met Met Arg Gly Ser Thr Glu
                115                 120                 125

Asp Phe Asp Arg Tyr Ala Ala Val Thr Gly Asp Glu Gly Trp Asn Trp
                130                 135                 140

Asp Asn Ile Gln Gln Phe Val Arg Lys Asn Glu Met Val Val Pro Pro
145                 150                 155                 160

Ala Asp Asn His Asn Thr Ser Gly Glu Phe Ile Pro Ala Val His Gly
                165                 170                 175

Thr Asn Gly Ser Val Ser Ile Ser Leu Pro Gly Phe Pro Thr Pro Leu
                180                 185                 190

Asp Asp Arg Val Leu Ala Thr Thr Gln Glu Gln Ser Glu Glu Phe Phe
                195                 200                 205

Phe Asn Pro Asp Met Gly Thr Gly His Pro Leu Gly Ile Ser Trp Ser
210                 215                 220

Ile Ala Ser Val Gly Asn Gly Gln Arg Ser Ser Ser Thr Ala Tyr
225                 230                 235                 240

Leu Arg Pro Ala Gln Ser Arg Pro Asn Leu Ser Val Leu Ile Asn Ala
                245                 250                 255

Gln Val Thr Lys Leu Val Asn Ser Gly Thr Thr Asn Gly Leu Pro Ala
                260                 265                 270

Phe Arg Cys Val Glu Tyr Ala Glu Gln Glu Gly Ala Pro Thr Thr Thr
                275                 280                 285

Val Cys Ala Lys Lys Glu Val Val Leu Ser Ala Gly Ser Val Gly Thr
290                 295                 300

Pro Ile Leu Leu Gln Leu Ser Gly Ile Gly Asp Glu Asn Asp Leu Ser
```

```
305                 310                 315                 320
Ser Val Gly Ile Asp Thr Ile Val Asn Asn Pro Ser Val Gly Arg Asn
                325                 330                 335

Leu Ser Asp His Leu Leu Pro Ala Ala Phe Phe Val Asn Ser Asn
                340                 345                 350

Gln Thr Phe Asp Asn Ile Phe Arg Asp Ser Ser Glu Phe Asn Val Asp
                355                 360                 365

Leu Asp Gln Trp Thr Asn Thr Arg Thr Gly Pro Leu Thr Ala Leu Ile
        370                 375                 380

Ala Asn His Leu Ala Trp Leu Arg Leu Pro Ser Asn Ser Ser Ile Phe
385                 390                 395                 400

Gln Thr Phe Pro Asp Pro Ala Ala Gly Pro Asn Ser Ala His Trp Glu
                405                 410                 415

Thr Ile Phe Ser Asn Gln Trp Tyr His Pro Ala Ile Pro Arg Pro Asp
                420                 425                 430

Thr Gly Ser Phe Met Ser Val Thr Asn Ala Leu Ile Ser Pro Val Ala
        435                 440                 445

Arg Gly Asp Ile Lys Leu Ala Thr Ser Asn Pro Phe Asp Lys Pro Leu
        450                 455                 460

Ile Asn Pro Gln Tyr Leu Ser Thr Glu Phe Asp Ile Phe Thr Met Ile
465                 470                 475                 480

Gln Ala Val Lys Ser Asn Leu Arg Phe Leu Ser Gly Gln Ala Trp Ala
                485                 490                 495

Asp Phe Val Ile Arg Pro Phe Asp Pro Arg Leu Arg Asp Pro Thr Asp
                500                 505                 510

Asp Ala Ala Ile Glu Ser Tyr Ile Arg Asp Asn Ala Asn Thr Ile Phe
        515                 520                 525

His Pro Val Gly Thr Ala Ser Met Ser Pro Arg Gly Ala Ser Trp Gly
        530                 535                 540

Val Val Asp Pro Asp Leu Lys Val Lys Gly Val Asp Gly Leu Arg Ile
545                 550                 555                 560

Val Asp Gly Ser Ile Leu Pro Phe Ala Pro Asn Ala His Thr Gln Gly
                565                 570                 575

Pro Ile Tyr Leu Val Gly Lys Gln Gly Ala Asp Leu Ile Lys Ala Asp
                580                 585                 590

Gln

<210> SEQ ID NO 10
<211> LENGTH: 593
<212> TYPE: PRT
<213> ORGANISM: Pleurotus eryngii MUT2

<400> SEQUENCE: 10

Met Ser Phe Gly Ala Leu Arg Gln Leu Leu Ile Ala Cys Leu Ala
1               5                   10                  15

Leu Pro Ser Leu Ala Ala Thr Asn Leu Pro Thr Ala Asp Phe Asp Tyr
                20                  25                  30

Val Val Val Gly Ala Gly Asn Ala Gly Asn Val Val Ala Ala Arg Leu
        35                  40                  45

Thr Glu Asp Pro Asp Val Ser Val Leu Val Leu Glu Ala Gly Val Ser
        50                  55                  60

Asp Glu Asn Val Leu Gly Ala Glu Ala Pro Leu Leu Ala Pro Gly Leu
65                  70                  75                  80

Val Pro Asn Ser Ile Phe Asp Trp Asn Tyr Thr Thr Thr Ala Gln Ala
```

```
                85                  90                  95
Gly Tyr Asn Gly Arg Ser Ile Ala Tyr Pro Arg Gly Arg Met Leu Gly
                100                 105                 110

Gly Ser Ser Ser Val His Tyr Met Val Met Arg Gly Ser Thr Glu
            115                 120                 125

Asp Phe Asp Arg Tyr Ala Ala Val Thr Gly Asp Glu Gly Trp Asn Trp
    130                 135                 140

Asp Asn Ile Gln Gln Phe Val Arg Lys Asn Glu Met Val Val Pro Pro
145                 150                 155                 160

Ala Asp Asn His Asn Thr Ser Gly Glu Phe Ile Pro Ala Val His Gly
                165                 170                 175

Thr Asn Gly Ser Val Ser Ile Ser Leu Pro Gly Phe Pro Thr Pro Leu
                180                 185                 190

Asp Asp Arg Val Leu Ala Thr Thr Gln Glu Gln Ser Glu Glu Phe Phe
            195                 200                 205

Phe Asn Pro Asp Met Gly Thr Gly His Pro Leu Gly Ile Ser Trp Ser
    210                 215                 220

Ile Ala Ser Val Gly Asn Gly Gln Arg Ser Ser Ser Thr Ala Tyr
225                 230                 235                 240

Leu Arg Pro Ala Gln Ser Arg Pro Asn Leu Ser Val Leu Ile Asn Ala
                245                 250                 255

Gln Val Thr Lys Leu Val Asn Ser Gly Thr Thr Asn Gly Leu Pro Ala
                260                 265                 270

Phe Arg Cys Val Glu Tyr Ala Glu Gln Glu Gly Ala Pro Thr Thr Thr
            275                 280                 285

Val Cys Ala Lys Lys Glu Val Val Leu Ser Ala Gly Ser Val Gly Thr
    290                 295                 300

Pro Ile Leu Leu Gln Leu Ser Gly Ile Gly Asp Glu Asn Asp Leu Ser
305                 310                 315                 320

Ser Val Gly Ile Asp Thr Ile Val Asn Asn Pro Ser Val Gly Arg Asn
                325                 330                 335

Leu Ser Asp His Leu Leu Leu Pro Ala Ala Phe Phe Val Asn Ser Asn
                340                 345                 350

Gln Thr Phe Asp Asn Ile Phe Arg Asp Ser Ser Glu Phe Asn Val Asp
            355                 360                 365

Leu Asp Gln Trp Thr Asn Thr Arg Thr Gly Pro Leu Thr Ala Leu Ile
    370                 375                 380

Ala Asn His Leu Ala Trp Leu Arg Leu Pro Ser Asn Ser Ser Ile Phe
385                 390                 395                 400

Gln Thr Phe Pro Asp Pro Ala Ala Gly Pro Asn Ser Ala His Trp Glu
                405                 410                 415

Thr Ile Phe Ser Asn Gln Trp Phe His Pro Ala Ile Pro Arg Pro Asp
                420                 425                 430

Thr Gly Ser Phe Met Ser Val Thr Asn Ala Leu Ile Ser Pro Val Ala
            435                 440                 445

Arg Gly Asp Ile Lys Leu Ala Thr Ser Asn Pro Phe Asp Lys Pro Leu
    450                 455                 460

Ile Asn Pro Gln Tyr Leu Ser Thr Glu Phe Asp Ile Phe Thr Met Ile
465                 470                 475                 480

Gln Ala Val Lys Ser Asn Leu Arg Phe Leu Ser Gly Gln Ala Trp Ala
                485                 490                 495

Asp Phe Val Ile Arg Pro Phe Asp Pro Arg Leu Arg Asp Pro Thr Asp
                500                 505                 510
```

```
Asp Ala Ala Ile Glu Ser Tyr Ile Arg Asp Asn Ala Asn Thr Met Trp
            515                 520                 525

His Pro Val Gly Thr Ala Ser Met Ser Pro Arg Gly Ala Ser Trp Gly
        530                 535                 540

Val Val Asp Pro Asp Leu Lys Val Lys Gly Val Asp Gly Leu Arg Ile
545                 550                 555                 560

Val Asp Gly Ser Ile Leu Pro Phe Ala Pro Asn Ala His Thr Gln Gly
                565                 570                 575

Pro Ile Tyr Leu Val Gly Lys Gln Gly Ala Asp Leu Ile Lys Ala Asp
            580                 585                 590

Gln

<210> SEQ ID NO 11
<211> LENGTH: 647
<212> TYPE: PRT
<213> ORGANISM: Thermothelomyces thermophilus

<400> SEQUENCE: 11

Met Gly Phe Leu Ala Ala Thr Leu Val Ser Cys Ala Ala Leu Ala Ser
1               5                   10                  15

Ala Ala Ser Ile Pro Arg Pro His Ala Lys Arg Gln Val Ser Gln Leu
            20                  25                  30

Arg Asp Asp Tyr Asp Phe Val Ile Val Gly Gly Gly Thr Ser Gly Leu
        35                  40                  45

Thr Val Ala Asp Arg Leu Thr Glu Ala Phe Pro Ala Lys Asn Val Leu
    50                  55                  60

Val Ile Glu Tyr Gly Asp Val His Tyr Ala Pro Gly Thr Phe Asp Pro
65                  70                  75                  80

Pro Thr Asp Trp Ile Thr Pro Gln Pro Asp Ala Pro Pro Ser Trp Ser
                85                  90                  95

Phe Asn Ser Leu Pro Asn Pro Asp Met Ala Asn Thr Thr Ala Phe Val
            100                 105                 110

Leu Ala Gly Gln Val Val Gly Gly Ser Ser Ala Val Asn Gly Met Phe
        115                 120                 125

Phe Asp Arg Ala Ser Arg His Asp Tyr Asp Ala Trp Thr Ala Val Gly
    130                 135                 140

Gly Ser Gly Phe Glu Gln Ser Ser His Lys Trp Asp Trp Glu Gly Leu
145                 150                 155                 160

Phe Pro Phe Phe Gln Lys Ser Val Thr Phe Thr Glu Pro Pro Ala Asp
                165                 170                 175

Ile Val Gln Lys Tyr His Tyr Thr Trp Asp Leu Ser Ala Tyr Gly Asn
            180                 185                 190

Gly Ser Thr Pro Ile Tyr Ser Ser Tyr Pro Val Phe Gln Trp Ala Asp
        195                 200                 205

Gln Pro Leu Leu Asn Gln Ala Trp Gln Glu Met Gly Ile Asn Pro Val
    210                 215                 220

Thr Glu Cys Ala Gly Gly Asp Lys Glu Gly Val Cys Trp Val Pro Ala
225                 230                 235                 240

Ser Gln His Pro Val Thr Ala Arg Arg Ser His Ala Gly Leu Gly His
                245                 250                 255

Tyr Ala Asp Val Leu Pro Arg Ala Asn Tyr Asp Leu Leu Val Gln His
            260                 265                 270

Gln Val Val Arg Val Val Phe Pro Asn Gly Pro Ser His Gly Pro Pro
        275                 280                 285
```

Leu Val Glu Ala Arg Ser Leu Ala Asp Asn His Leu Phe Asn Val Thr
            290                 295                 300

Val Lys Gly Glu Val Ile Ile Ser Ala Gly Leu His Thr Pro Thr
305                 310                 315                 320

Val Leu Gln Arg Ser Gly Ile Gly Pro Ala Ser Phe Leu Asp Asp Ala
            325                 330                 335

Gly Ile Pro Val Thr Leu Asp Leu Pro Gly Val Gly Ala Asn Leu Gln
            340                 345                 350

Asp His Cys Gly Pro Pro Val Thr Trp Asn Tyr Thr Glu Pro Tyr Thr
            355                 360                 365

Gly Phe Phe Pro Leu Pro Ser Glu Met Val Asn Asn Ala Thr Phe Lys
            370                 375                 380

Ala Glu Ala Ile Thr Gly Phe Asp Glu Val Pro Ala Arg Gly Pro Tyr
385                 390                 395                 400

Thr Leu Ala Gly Gly Asn Asn Ala Ile Phe Val Ser Leu Pro His Leu
            405                 410                 415

Thr Ala Asp Tyr Gly Ala Ile Thr Ala Lys Ile Arg Ala Met Val Ala
            420                 425                 430

Asp Gly Thr Ala Ala Ser Tyr Leu Ala Ala Asp Val Arg Thr Ile Pro
            435                 440                 445

Gly Met Val Ala Gly Tyr Glu Ala Gln Leu Leu Val Leu Ala Asp Leu
            450                 455                 460

Leu Asp Asn Pro Glu Ala Pro Ser Leu Glu Thr Pro Trp Ala Thr Ser
465                 470                 475                 480

Glu Ala Pro Gln Thr Ser Ser Val Leu Ala Phe Leu Leu His Pro Leu
            485                 490                 495

Ser Arg Gly Ser Val Arg Leu Asn Leu Ser Asp Pro Leu Ala Gln Pro
            500                 505                 510

Val Leu Asp Tyr Arg Ser Gly Ser Asn Pro Val Asp Ile Asp Leu His
            515                 520                 525

Leu Ala His Val Arg Phe Leu Arg Gly Leu Leu Asp Thr Pro Thr Met
530                 535                 540

Gln Ala Arg Gly Ala Leu Glu Thr Ala Pro Gly Ser Ala Val Ala Asp
545                 550                 555                 560

Ser Asp Glu Ala Leu Gly Glu Tyr Val Arg Ser His Ser Thr Leu Ser
            565                 570                 575

Phe Met His Pro Cys Cys Thr Ala Ala Met Leu Pro Glu Asp Arg Gly
            580                 585                 590

Gly Val Val Gly Pro Asp Leu Lys Val His Gly Ala Glu Gly Leu Arg
            595                 600                 605

Val Val Asp Met Ser Val Met Pro Leu Leu Pro Gly Ala His Leu Ser
            610                 615                 620

Ala Thr Ala Tyr Ala Val Gly Glu Lys Ala Ala Asp Ile Ile Gln
625                 630                 635                 640

Glu Trp Met Asp Lys Glu Gln
            645

<210> SEQ ID NO 12
<211> LENGTH: 988
<212> TYPE: PRT
<213> ORGANISM: Thermothelomyces thermophilus

<400> SEQUENCE: 12

Met Arg Ala Ser Pro Ser Ser Arg Thr Leu Leu Ala Ser Leu Ala Leu

-continued

```
1               5                   10                  15
Ser Ser Leu Pro Leu Ser Phe Gly Gln Leu Ser Ile Pro Thr Asp Leu
                20                  25                  30

Pro Asp Ser Trp Glu Tyr Gln Gly Cys Tyr Thr Asp Val Pro Gly Arg
                35                  40                  45

Thr Ile Asn Ser Ala Ser Tyr Ala Asp Gly Thr Asn Met Thr Asn Ala
 50                      55                  60

Ala Cys Leu Ser Tyr Cys Ala Ser Lys Gly Phe Pro Tyr Ala Gly Thr
 65                  70                  75                  80

Glu Tyr Ser Val Glu Cys Phe Cys Gly Thr Thr Leu Ala Ser Ser Ser
                 85                  90                  95

Ala Lys Val Ala Asp Ser Glu Cys Asn Met Pro Cys Ser Gly Ala Pro
                100                 105                 110

Ser Glu Pro Cys Gly Ala Gly Ser Arg Leu Ser Leu Phe His Ser Ser
                115                 120                 125

Ala Val Thr Gly Pro Ala Ala Asn Pro Gly Val Asn Asp Phe Thr His
            130                 135                 140

Leu Gly Cys Tyr Ala Glu Gly Lys Thr Gly Arg Ala Leu Thr Tyr Asn
145                 150                 155                 160

Pro Gly Leu Pro Gly Ala Asp Met Thr Val Ala Lys Cys Thr Ala Ala
                165                 170                 175

Cys Arg Ala Ala Asn Tyr Ile Leu Ala Gly Val Glu Tyr Gly Gly Glu
                180                 185                 190

Cys Tyr Cys Gly Asn Thr Ile Ala Asn Gly Gly Ala Pro Ala Asp Ser
                195                 200                 205

Gly Cys Ser Met Val Cys Asn Gly Asn Ser Thr Glu Phe Cys Gly Gly
            210                 215                 220

Pro Asp Arg Leu Asn Val Tyr Ser Tyr Lys Asn Gln Tyr Glu Pro Thr
225                 230                 235                 240

Ala Thr Ser Thr Thr Gly Ala Gly Ser Thr Ser Ser Ser Ser Val Pro
                245                 250                 255

Ser Ala Thr Gly Leu Pro Glu Gly Trp Ser Tyr Gln Gly Cys Trp Ile
                260                 265                 270

Asp Gly Lys Gln Gly Arg Ile Leu Pro Tyr Gln Leu Pro Asp Ser Gln
                275                 280                 285

Thr Asn Ser Arg Ala Ala Cys Ala Asn Ala Cys Ala Glu Ala Gly Tyr
            290                 295                 300

Thr Val Ser Gly Thr Glu Tyr Ala Val Gln Cys Phe Cys Gly Asp Ala
305                 310                 315                 320

Ile His Asn Gly Gly Val Glu Thr Asp Glu Ala Asp Cys Ser Thr Pro
                325                 330                 335

Cys Pro Gly Ala Pro Gly Glu Lys Cys Gly Ala Gly Asp Arg Leu Ser
                340                 345                 350

Ile Val Ser Arg Gly Pro Pro Lys Ile Tyr Ala Pro Pro Ala Pro Ile
            355                 360                 365

Glu Lys Ile Gly Asp Trp Glu Tyr Gln Gly Cys Ala Glu Asp Asn Ile
                370                 375                 380

Asn Asp Lys Arg Thr Phe Phe Trp Gln Ile Phe Phe Asn Asp Ile Met
385                 390                 395                 400

Thr Pro Glu Met Cys Leu Asp Arg Cys Ala Glu Phe Gly Tyr His Ala
                405                 410                 415

Ala Gly Leu Glu Tyr Gly Gln Glu Cys Tyr Cys Gly Asp Pro Ala Asn
            420                 425                 430
```

```
Met Ala Thr His Gly Ala Thr Phe Arg Pro Glu Ser Glu Cys Asn Val
            435                 440                 445
Val Cys Ala Gly Asn Ser Thr Ala Ile Cys Gly Gly Leu Ala Arg Leu
    450                 455                 460
Thr Thr Tyr Phe Trp Ile Gly Thr Pro Phe Tyr Ser Trp Asp Phe Pro
465                 470                 475                 480
Gln Asp Trp Arg Ala Gly Lys Tyr Glu Phe Leu Val Asp Gly Val Asn
                485                 490                 495
Ile Pro Leu Ile Thr His Glu Thr Ile Thr Gly Lys Val Ser Phe Ile
                500                 505                 510
Ser Lys Gly Ala Thr Gly Pro Gly Asn Glu Thr Gly Ala Tyr Glu Phe
            515                 520                 525
Asp Pro Ala Thr Leu Glu Phe Arg Glu Leu His Ile Lys Thr Asp Val
        530                 535                 540
Phe Cys Ala Ala Ser Val Thr Leu Pro Asp Lys Ala Gly Arg Gln Leu
545                 550                 555                 560
Asn Val Gly Gly Trp Ala Gly Glu Ala Thr Tyr Gly Thr Arg Leu Tyr
                565                 570                 575
Trp Pro Asp Gly Ala Pro Gly Val Pro Gly Thr His Asp Trp Gln Glu
            580                 585                 590
Asn Val Asn Val Leu His Leu Gln Ala Gly Arg Trp Tyr Pro Ser Val
                595                 600                 605
Leu Val Leu Thr Asn Gly Ser Val Met Val Val Gly Gly Leu Ile Gly
        610                 615                 620
Ser Asn Asp Ala Ala Thr Pro Ser Ile Glu Ile Leu Pro Tyr Thr Gly
625                 630                 635                 640
Thr Pro Pro Leu Tyr Met Asp Trp Leu Asp Arg Thr His Pro Asn Asn
                645                 650                 655
Leu Tyr Pro Phe Leu Cys Ile Leu Pro Gly Gly Gly Ile Phe Val Gln
            660                 665                 670
Tyr Trp Asn Glu Ala Arg Ile Leu Asp Pro Val Thr Phe Asp Thr Val
        675                 680                 685
Lys Thr Leu Pro Asp Ala Pro Gly Ala Pro Asn Asp Pro Lys Gly Gly
        690                 695                 700
Arg Thr Tyr Pro Leu Glu Gly Thr Ala Val Leu Leu Pro Gln Lys Tyr
705                 710                 715                 720
Pro Tyr Thr Asp Pro Leu Gly Val Leu Ile Cys Gly Gly Ser Thr Glu
                725                 730                 735
Gly Pro Gly Asn Ala Leu Asp Asn Cys Val Ser Ile Tyr Pro Glu Ala
            740                 745                 750
Asp Glu Pro Glu Trp Gln Ile Glu Arg Met Pro Ser Phe Arg Val Met
        755                 760                 765
Thr Cys Met Ala Pro Leu Pro Asp Gly Thr Tyr Leu Ile Ala Asn Gly
        770                 775                 780
Ala Leu His Gly Val Ala Gly Phe Gly Leu Val Gly Pro Asn Leu
785                 790                 795                 800
Asn Ala Leu Leu Tyr Asp Pro Ser Lys Pro Leu Gly Ser Arg Ile Thr
                805                 810                 815
Val Ala Ala Asn Thr Thr Ile Ala Arg Met Tyr His Ser Glu Ala Ile
                820                 825                 830
Thr Leu Leu Asp Gly Arg Val Leu Ile Ser Gly Ser Asn Pro Glu Asp
            835                 840                 845
```

```
Gly Val Asn Pro Glu Glu Tyr Arg Val Glu Val Phe Leu Pro Pro Tyr
    850                 855                 860

Leu Leu Ala Gly Lys Pro Arg Pro Thr Phe Thr Leu Glu Asn Arg Asp
865                 870                 875                 880

Trp Ala His Gly Gln Thr Gly Ile Pro Phe Thr Leu Gly Ser Pro Ala
                885                 890                 895

Arg Asn Gly Asp Ile Thr Ala Thr Leu Leu Gly Ser Val Ala Ser Thr
                900                 905                 910

His Gly Asn Ser Met Gly Ala Arg Thr Leu Met Pro Arg Val Ser Cys
            915                 920                 925

Arg Gly Thr Ser Cys Thr Val Asp Ala Pro Thr Ala Asn Ile Cys
            930                 935                 940

Pro Pro Gly Trp Tyr Gln Phe Phe Val Leu Asp Gly Ile Pro Ala
945                 950                 955                 960

Val Gly Val Tyr Val Arg Ile Gly Gly Asp Ala Gly Gln Ile Gly Asn
                965                 970                 975

Trp Pro Gln Ala Pro Asp Phe Ser Val Pro Gly Val
                980                 985
```

<210> SEQ ID NO 13
<211> LENGTH: 680
<212> TYPE: PRT
<213> ORGANISM: Fusarium graminearum

<400> SEQUENCE: 13

```
Met Lys His Leu Leu Thr Leu Ala Leu Cys Phe Ser Ser Ile Asn Ala
1               5                   10                  15

Val Ala Val Thr Val Pro His Lys Ala Val Gly Thr Gly Ile Pro Glu
                20                  25                  30

Gly Ser Leu Gln Phe Leu Ser Leu Arg Ala Ser Ala Pro Ile Gly Ser
            35                  40                  45

Ala Ile Ser Arg Asn Asn Trp Ala Val Thr Cys Asp Ser Ala Gln Ser
        50                  55                  60

Gly Asn Glu Cys Asn Lys Ala Ile Asp Gly Asn Lys Asp Thr Phe Trp
65                  70                  75                  80

His Thr Phe Tyr Gly Ala Asn Gly Asp Pro Lys Pro His Thr Tyr
                85                  90                  95

Thr Ile Asp Met Lys Thr Thr Gln Asn Val Asn Gly Leu Ser Met Leu
                100                 105                 110

Pro Arg Gln Asp Gly Asn Gln Asn Gly Trp Ile Gly Arg His Glu Val
            115                 120                 125

Tyr Leu Ser Ser Asp Gly Thr Asn Trp Gly Ser Pro Val Ala Ser Gly
        130                 135                 140

Ser Trp Phe Ala Asp Ser Thr Thr Lys Tyr Ser Asn Phe Glu Thr Arg
145                 150                 155                 160

Pro Ala Arg Tyr Val Arg Leu Val Ala Ile Thr Glu Ala Asn Gly Gln
                165                 170                 175

Pro Trp Thr Ser Ile Ala Glu Ile Asn Val Phe Gln Ala Ser Ser Tyr
            180                 185                 190

Thr Ala Pro Gln Pro Gly Leu Gly Arg Trp Gly Pro Thr Ile Asp Leu
        195                 200                 205

Pro Ile Val Pro Ala Ala Ala Ile Glu Pro Thr Ser Gly Arg Val
    210                 215                 220

Leu Met Trp Ser Ser Tyr Arg Asn Asp Ala Phe Gly Gly Ser Pro Gly
225                 230                 235                 240
```

```
Gly Ile Thr Leu Thr Ser Ser Trp Asp Pro Ser Thr Gly Ile Val Ser
                245                 250                 255

Asp Arg Thr Val Thr Val Lys His Asp Met Phe Cys Pro Gly Ile
                260                 265                 270

Ser Met Asp Gly Asn Gly Gln Ile Val Val Thr Gly Gly Asn Asp Ala
            275                 280                 285

Lys Lys Thr Ser Leu Tyr Asp Ser Ser Ser Asp Ser Trp Ile Pro Gly
        290                 295                 300

Pro Asp Met Gln Val Ala Arg Gly Tyr Gln Ser Ser Ala Thr Met Ser
305                 310                 315                 320

Asp Gly Arg Val Phe Thr Ile Gly Gly Ser Trp Ser Gly Val Phe
                325                 330                 335

Glu Lys Asn Gly Glu Val Tyr Ser Pro Ser Ser Lys Thr Trp Thr Ser
            340                 345                 350

Leu Pro Asn Ala Lys Val Asn Pro Met Leu Thr Ala Asp Lys Gln Gly
        355                 360                 365

Leu Tyr Arg Ser Asp Asn His Ala Trp Leu Phe Gly Trp Lys Lys Gly
        370                 375                 380

Ser Val Phe Gln Ala Gly Pro Ser Thr Ala Met Asn Trp Tyr Tyr Thr
385                 390                 395                 400

Ser Gly Ser Gly Asp Val Lys Ser Ala Gly Lys Arg Gln Ser Asn Arg
                405                 410                 415

Gly Val Ala Pro Asp Ala Met Cys Gly Asn Ala Val Met Tyr Asp Ala
                420                 425                 430

Val Lys Gly Lys Ile Leu Thr Phe Gly Gly Ser Pro Asp Tyr Gln Asp
            435                 440                 445

Ser Asp Ala Thr Thr Asn Ala His Ile Ile Thr Leu Gly Glu Pro Gly
        450                 455                 460

Thr Ser Pro Asn Thr Val Phe Ala Ser Asn Gly Leu Tyr Phe Ala Arg
465                 470                 475                 480

Thr Phe His Thr Ser Val Val Leu Pro Asp Gly Ser Thr Phe Ile Thr
                485                 490                 495

Gly Gly Gln Arg Arg Gly Ile Pro Phe Glu Asp Ser Thr Pro Val Phe
                500                 505                 510

Thr Pro Glu Ile Tyr Val Pro Glu Gln Asp Thr Phe Tyr Lys Gln Asn
            515                 520                 525

Pro Asn Ser Ile Val Arg Val Tyr His Ser Ile Ser Leu Leu Leu Pro
        530                 535                 540

Asp Gly Arg Val Phe Asn Gly Gly Gly Leu Cys Gly Asp Cys Thr
545                 550                 555                 560

Thr Asn His Phe Asp Ala Gln Ile Phe Thr Pro Asn Tyr Leu Tyr Asn
                565                 570                 575

Ser Asn Gly Asn Leu Ala Thr Arg Pro Lys Ile Thr Arg Thr Ser Thr
            580                 585                 590

Gln Ser Val Lys Val Gly Gly Arg Ile Thr Ile Ser Thr Asp Ser Ser
        595                 600                 605

Ile Ser Lys Ala Ser Leu Ile Arg Tyr Gly Thr Ala Thr His Thr Val
        610                 615                 620

Asn Thr Asp Gln Arg Arg Ile Pro Leu Thr Leu Thr Asn Asn Gly Gly
625                 630                 635                 640

Asn Ser Tyr Ser Phe Gln Val Pro Ser Asp Ser Gly Val Ala Leu Pro
                645                 650                 655
```

Gly Tyr Trp Met Leu Phe Val Met Asn Ser Ala Gly Val Pro Ser Val
              660                 665                 670

Ala Ser Thr Ile Arg Val Thr Gln
        675                 680

<210> SEQ ID NO 14
<211> LENGTH: 318
<212> TYPE: PRT
<213> ORGANISM: Echerichia coli

<400> SEQUENCE: 14

Met Lys Ala Phe Thr Tyr Glu Arg Val Asn Thr Pro Ala Glu Ala Ala
1               5                   10                  15

Leu Ser Ala Gln Arg Val Pro Gly Ala Lys Phe Ile Ala Gly Gly Thr
            20                  25                  30

Asn Leu Leu Asp Leu Met Lys Leu Glu Ile Glu Thr Pro Thr His Leu
        35                  40                  45

Ile Asp Val Asn Gly Leu Gly Leu Asp Lys Ile Glu Val Thr Asp Ala
    50                  55                  60

Gly Gly Leu Arg Ile Gly Ala Leu Val Arg Asn Thr Asp Leu Val Ala
65                  70                  75                  80

His Glu Arg Val Arg Arg Asp Tyr Ala Val Leu Ser Arg Ala Leu Leu
                85                  90                  95

Ala Gly Ala Ser Gly Gln Leu Arg Asn Gln Ala Thr Thr Ala Gly Asn
            100                 105                 110

Leu Leu Gln Arg Thr Arg Cys Pro Tyr Phe Tyr Asp Thr Asn Gln Pro
        115                 120                 125

Cys Asn Lys Arg Leu Pro Gly Ser Gly Cys Ala Ala Leu Glu Gly Phe
    130                 135                 140

Ser Arg Gln His Ala Val Val Gly Val Ser Glu Ala Cys Ile Ala Thr
145                 150                 155                 160

His Pro Ser Asp Met Ala Val Ala Met Arg Leu Leu Asp Ala Val Val
                165                 170                 175

Glu Thr Ile Thr Pro Glu Gly Lys Thr Arg Ser Ile Thr Leu Ala Asp
            180                 185                 190

Phe Tyr His Pro Pro Gly Lys Thr Pro His Ile Glu Thr Ala Leu Leu
        195                 200                 205

Pro Gly Glu Leu Ile Val Ala Val Thr Leu Pro Pro Pro Leu Gly Gly
    210                 215                 220

Lys His Ile Tyr Arg Lys Val Arg Asp Arg Ala Ser Tyr Thr Phe Ala
225                 230                 235                 240

Leu Val Ser Val Ala Ala Ile Ile Gln Pro Asp Gly Ser Gly Arg Val
                245                 250                 255

Ala Leu Gly Gly Val Ala His Lys Pro Trp Arg Ile Glu Ala Ala Asp
            260                 265                 270

Ala Gln Leu Ser Gln Gly Ala Gln Ala Val Tyr Asp Ala Leu Phe Ala
        275                 280                 285

Ser Ala His Pro Thr Ala Glu Asn Thr Phe Lys Leu Leu Leu Ala Lys
    290                 295                 300

Arg Thr Leu Ala Ser Val Leu Ala Glu Ala Arg Ala Gln Ala
305                 310                 315

<210> SEQ ID NO 15
<211> LENGTH: 371
<212> TYPE: PRT
<213> ORGANISM: Agrocybe aegerita

<400> SEQUENCE: 15

```
Met Lys Tyr Phe Pro Leu Phe Pro Thr Leu Val Phe Ala Ala Arg Val
1               5                   10                  15

Val Ala Phe Pro Ala Tyr Ala Ser Leu Ala Gly Leu Ser Gln Gln Glu
            20                  25                  30

Leu Asp Ala Ile Ile Pro Thr Leu Glu Ala Arg Glu Pro Gly Leu Pro
        35                  40                  45

Pro Gly Pro Leu Glu Asn Ser Ser Ala Lys Leu Val Asn Asp Glu Ala
    50                  55                  60

His Pro Trp Lys Pro Leu Arg Pro Gly Asp Ile Arg Gly Pro Cys Pro
65                  70                  75                  80

Gly Leu Asn Thr Leu Ala Ser His Gly Tyr Leu Pro Arg Asn Gly Val
                85                  90                  95

Ala Thr Pro Val Gln Ile Ile Asn Ala Val Gln Glu Gly Leu Asn Phe
            100                 105                 110

Asp Asn Gln Ala Ala Val Phe Ala Thr Tyr Ala Ala His Leu Val Asp
            115                 120                 125

Gly Asn Leu Ile Thr Asp Leu Leu Ser Ile Gly Arg Lys Thr Arg Leu
130                 135                 140

Thr Gly Pro Asp Pro Pro Pro Ala Ser Val Gly Gly Leu Asn Glu
145                 150                 155                 160

His Gly Thr Phe Glu Gly Asp Ala Ser Met Thr Arg Gly Asp Ala Phe
                165                 170                 175

Phe Gly Asn Asn His Asp Phe Asn Glu Thr Leu Phe Glu Gln Leu Val
            180                 185                 190

Asp Tyr Ser Asn Arg Phe Gly Gly Lys Tyr Asn Leu Thr Val Ala
        195                 200                 205

Gly Glu Leu Arg Phe Lys Arg Ile Gln Asp Ser Ile Ala Thr Asn Pro
210                 215                 220

Asn Phe Ser Phe Val Asp Phe Arg Phe Thr Ala Tyr Gly Glu Thr
225                 230                 235                 240

Thr Phe Pro Ala Asn Leu Phe Val Asp Gly Arg Arg Asp Asp Gly Gln
            245                 250                 255

Leu Asp Met Asp Ala Ala Arg Ser Phe Phe Gln Phe Ser Arg Met Pro
        260                 265                 270

Asp Asp Phe Phe Arg Ala Pro Ser Pro Arg Ser Gly Thr Gly Val Glu
    275                 280                 285

Val Val Ile Gln Ala His Pro Met Gln Pro Gly Arg Asn Val Gly Lys
    290                 295                 300

Ile Asn Ser Tyr Thr Val Asp Pro Thr Ser Ser Asp Phe Ser Thr Pro
305                 310                 315                 320

Cys Leu Met Tyr Glu Lys Phe Val Asn Ile Thr Val Lys Ser Leu Tyr
                325                 330                 335

Pro Asn Pro Thr Val Gln Leu Lys Ala Leu Asn Thr Asn Leu Asp
            340                 345                 350

Phe Phe Phe Gln Gly Val Ala Ala Gly Cys Thr Gln Val Phe Pro Tyr
        355                 360                 365

Gly Arg Asp
    370
```

<210> SEQ ID NO 16
<211> LENGTH: 373
<212> TYPE: PRT

<213> ORGANISM: Culduriomyces fumago

<400> SEQUENCE: 16

```
Met Phe Ser Lys Val Leu Pro Phe Val Gly Ala Val Ala Ala Leu Pro
1               5                   10                  15
His Ser Val Arg Gln Glu Pro Gly Ser Gly Ile Gly Tyr Pro Tyr Asp
            20                  25                  30
Asn Asn Thr Leu Pro Tyr Val Ala Pro Gly Pro Thr Asp Ser Arg Ala
        35                  40                  45
Pro Cys Pro Ala Leu Asn Ala Leu Ala Asn His Gly Tyr Ile Pro His
    50                  55                  60
Asp Gly Arg Ala Ile Ser Arg Glu Thr Leu Gln Asn Ala Phe Leu Asn
65                  70                  75                  80
His Met Gly Ile Ala Asn Ser Val Ile Glu Leu Ala Leu Thr Asn Ala
                85                  90                  95
Phe Val Val Cys Glu Tyr Val Thr Gly Ser Asp Cys Gly Asp Ser Leu
            100                 105                 110
Val Asn Leu Thr Leu Leu Ala Glu Pro His Ala Phe Glu His Asp His
        115                 120                 125
Ser Phe Ser Arg Lys Asp Tyr Lys Gln Gly Val Ala Asn Ser Asn Asp
    130                 135                 140
Phe Ile Asp Asn Arg Asn Phe Asp Ala Glu Thr Phe Gln Thr Ser Leu
145                 150                 155                 160
Asp Val Val Ala Gly Lys Thr His Phe Asp Tyr Ala Asp Met Asn Glu
                165                 170                 175
Ile Arg Leu Gln Arg Glu Ser Leu Ser Asn Glu Leu Asp Phe Pro Gly
            180                 185                 190
Trp Phe Thr Glu Ser Lys Pro Ile Gln Asn Val Glu Ser Gly Phe Ile
        195                 200                 205
Phe Ala Leu Val Ser Asp Phe Asn Leu Pro Asp Asn Asp Glu Asn Pro
210                 215                 220
Leu Val Arg Ile Asp Trp Trp Lys Tyr Trp Phe Thr Asn Glu Ser Phe
225                 230                 235                 240
Pro Tyr His Leu Gly Trp His Pro Pro Ser Pro Ala Arg Glu Ile Glu
                245                 250                 255
Phe Val Thr Ser Ala Ser Ser Ala Val Leu Ala Ala Ser Val Thr Ser
            260                 265                 270
Thr Pro Ser Ser Leu Pro Ser Gly Ala Ile Gly Pro Gly Ala Glu Ala
        275                 280                 285
Val Pro Leu Ser Phe Ala Ser Thr Met Thr Pro Phe Leu Leu Ala Thr
    290                 295                 300
Asn Ala Pro Tyr Tyr Ala Gln Asp Pro Thr Leu Gly Pro Asn Asp Lys
305                 310                 315                 320
Arg Glu Ala Ala Pro Ala Ala Thr Thr Ser Met Ala Val Phe Lys Asn
                325                 330                 335
Pro Tyr Leu Glu Ala Ile Gly Thr Gln Asp Ile Lys Asn Gln Gln Ala
            340                 345                 350
Tyr Val Ser Ser Lys Ala Ala Ala Met Ala Ser Ala Met Ala Ala Asn
        355                 360                 365
Lys Ala Arg Asn Leu
    370
```

<210> SEQ ID NO 17
<211> LENGTH: 342

```
<212> TYPE: PRT
<213> ORGANISM: Pseudozyma antarctica

<400> SEQUENCE: 17

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65              70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 18
<211> LENGTH: 519
<212> TYPE: PRT
<213> ORGANISM: Trametes versicolor

<400> SEQUENCE: 18
```

-continued

```
Met Gly Leu Gln Arg Phe Ser Phe Phe Val Thr Leu Ala Leu Val Ala
1               5                   10                  15

Arg Ser Leu Ala Ala Ile Gly Pro Val Ala Ser Leu Val Val Ala Asn
            20                  25                  30

Ala Pro Val Ser Pro Asp Asp Phe Leu Arg Asp Ala Ile Val Val Asn
        35                  40                  45

Gly Val Val Pro Ser Pro Leu Ile Thr Gly Lys Lys Gly Asp Arg Phe
    50                  55                  60

Gln Leu Asn Val Val Asp Thr Leu Thr Asn His Ser Met Leu Lys Ser
65                  70                  75                  80

Thr Ser Ile His Trp His Gly Phe Phe Gln Ala Gly Thr Asn Trp Ala
                85                  90                  95

Asp Gly Pro Ala Phe Val Asn Gln Cys Pro Ile Ala Ser Gly His Ser
            100                 105                 110

Phe Leu Tyr Asp Phe His Val Pro Asp Gln Ala Gly Thr Phe Trp Tyr
        115                 120                 125

His Ser Arg Leu Ser Thr Gln Tyr Cys Asp Gly Leu Arg Gly Pro Phe
    130                 135                 140

Val Val Tyr Asp Pro Lys Asp Pro His Ala Ser Arg Tyr Asp Val Asp
145                 150                 155                 160

Asn Glu Ser Thr Val Ile Thr Leu Thr Asp Trp Tyr His Thr Ala Ala
                165                 170                 175

Arg Leu Gly Pro Arg Phe Pro Leu Gly Ala Asp Ala Thr Leu Ile Asn
            180                 185                 190

Gly Leu Gly Arg Ser Ala Ser Thr Pro Thr Ala Ala Leu Ala Val Ile
        195                 200                 205

Asn Val Gln His Gly Lys Arg Tyr Arg Leu Arg Leu Val Ser Ile Ser
    210                 215                 220

Cys Asp Pro Asn Tyr Thr Phe Ser Ile Asp Gly His Asn Leu Thr Val
225                 230                 235                 240

Ile Glu Val Asp Gly Ile Asn Ser Gln Pro Leu Leu Val Asp Ser Ile
                245                 250                 255

Gln Ile Phe Ala Ala Gln Arg Tyr Ser Phe Val Leu Asn Ala Asn Gln
            260                 265                 270

Thr Val Gly Asn Tyr Trp Val Arg Ala Asn Pro Asn Phe Gly Thr Val
        275                 280                 285

Gly Phe Ala Gly Gly Ile Asn Ser Ala Ile Leu Arg Tyr Gln Gly Ala
    290                 295                 300

Pro Val Ala Glu Pro Thr Thr Thr Gln Thr Pro Ser Val Ile Pro Leu
305                 310                 315                 320

Ile Glu Thr Asn Leu His Pro Leu Ala Arg Met Pro Val Pro Gly Ser
                325                 330                 335

Pro Thr Pro Gly Gly Val Asp Lys Ala Leu Asn Leu Ala Phe Asn Phe
            340                 345                 350

Asn Gly Thr Asn Phe Phe Ile Asn Asn Ala Ser Phe Thr Pro Pro Thr
        355                 360                 365

Val Pro Val Leu Leu Gln Ile Leu Ser Gly Ala Gln Thr Ala Gln Glu
    370                 375                 380

Leu Leu Pro Ala Gly Ser Val Tyr Pro Leu Pro Ala His Ser Thr Ile
385                 390                 395                 400

Glu Ile Thr Leu Pro Ala Thr Ala Leu Ala Pro Gly Ala Pro His Pro
                405                 410                 415

Phe His Leu His Gly His Ala Phe Ala Val Val Arg Ser Ala Gly Ser
```

```
              420                 425                 430
Thr Thr Tyr Asn Tyr Asn Asp Pro Ile Phe Arg Asp Val Val Ser Thr
        435                 440                 445

Gly Thr Pro Ala Ala Gly Asp Asn Val Thr Ile Arg Phe Gln Thr Asp
    450                 455                 460

Asn Pro Gly Pro Trp Phe Leu His Cys His Ile Asp Phe His Leu Glu
465                 470                 475                 480

Ala Gly Phe Ala Ile Val Phe Ala Glu Asp Val Ala Asp Val Lys Ala
                485                 490                 495

Ala Asn Pro Val Pro Lys Ala Trp Ser Asp Leu Cys Pro Ile Tyr Asp
            500                 505                 510

Gly Leu Ser Glu Ala Asn Gln
        515

<210> SEQ ID NO 19
<211> LENGTH: 353
<212> TYPE: PRT
<213> ORGANISM: Armoracia rusticana

<400> SEQUENCE: 19

Met His Phe Ser Ser Ser Ser Thr Leu Phe Thr Cys Ile Thr Leu Ile
1               5                   10                  15

Pro Leu Val Cys Leu Ile Leu His Ala Ser Leu Ser Asp Ala Gln Leu
            20                  25                  30

Thr Pro Thr Phe Tyr Asp Asn Ser Cys Pro Asn Val Ser Asn Ile Val
        35                  40                  45

Arg Asp Thr Ile Val Asn Glu Leu Arg Ser Asp Pro Arg Ile Ala Ala
    50                  55                  60

Ser Ile Leu Arg Leu His Phe His Asp Cys Phe Val Asn Gly Cys Asp
65                  70                  75                  80

Ala Ser Ile Leu Leu Asp Asn Thr Thr Ser Phe Arg Thr Glu Lys Asp
                85                  90                  95

Ala Phe Gly Asn Ala Asn Ser Ala Arg Gly Phe Pro Val Ile Asp Arg
            100                 105                 110

Met Lys Ala Ala Val Glu Ser Ala Cys Pro Arg Thr Val Ser Cys Ala
        115                 120                 125

Asp Leu Leu Thr Ile Ala Ala Gln Gln Ser Val Thr Leu Ala Gly Gly
    130                 135                 140

Pro Ser Trp Arg Val Pro Leu Gly Arg Arg Asp Ser Leu Gln Ala Phe
145                 150                 155                 160

Leu Asp Leu Ala Asn Ala Asn Leu Pro Ala Pro Phe Phe Thr Leu Pro
                165                 170                 175

Gln Leu Lys Asp Ser Phe Arg Asn Val Gly Leu Asn Arg Ser Ser Asp
            180                 185                 190

Leu Val Ala Leu Ser Gly Gly His Thr Phe Gly Lys Asn Gln Cys Arg
        195                 200                 205

Phe Ile Met Asp Arg Leu Tyr Asn Phe Ser Asn Thr Gly Leu Pro Asp
    210                 215                 220

Pro Thr Leu Asn Thr Thr Tyr Leu Gln Thr Leu Arg Gly Leu Cys Pro
225                 230                 235                 240

Leu Asn Gly Asn Leu Ser Ala Leu Val Asp Phe Asp Leu Arg Thr Pro
                245                 250                 255

Thr Ile Phe Asp Asn Lys Tyr Tyr Val Asn Leu Glu Glu Gln Lys Gly
            260                 265                 270
```

```
Leu Ile Gln Ser Asp Gln Glu Leu Phe Ser Ser Pro Asn Ala Thr Asp
            275                 280                 285

Thr Ile Pro Leu Val Arg Ser Phe Ala Asn Ser Thr Gln Thr Phe Phe
290                 295                 300

Asn Ala Phe Val Glu Ala Met Asp Arg Met Gly Asn Ile Thr Pro Leu
305                 310                 315                 320

Thr Gly Thr Gln Gly Gln Ile Arg Leu Asn Cys Arg Val Val Asn Ser
                325                 330                 335

Asn Ser Leu Leu His Asp Met Val Glu Val Val Asp Phe Val Ser Ser
            340                 345                 350

Met
```

<210> SEQ ID NO 20
<211> LENGTH: 527
<212> TYPE: PRT
<213> ORGANISM: Bos taurus

<400> SEQUENCE: 20

```
Met Ala Asp Asn Arg Asp Pro Ala Ser Asp Gln Met Lys His Trp Lys
1               5                   10                  15

Glu Gln Arg Ala Ala Gln Lys Pro Asp Val Leu Thr Thr Gly Gly Gly
            20                  25                  30

Asn Pro Val Gly Asp Lys Leu Asn Ser Leu Thr Val Gly Pro Arg Gly
        35                  40                  45

Pro Leu Leu Val Gln Asp Val Val Phe Thr Asp Glu Met Ala His Phe
50                  55                  60

Asp Arg Glu Arg Ile Pro Glu Arg Val Val His Ala Lys Gly Ala Gly
65                  70                  75                  80

Ala Phe Gly Tyr Phe Glu Val Thr His Asp Ile Thr Arg Tyr Ser Lys
                85                  90                  95

Ala Lys Val Phe Glu His Ile Gly Lys Arg Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
    130                 135                 140

Leu Val Gly Asn Asn Thr Pro Ile Phe Phe Ile Arg Asp Ala Leu Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
    210                 215                 220

Ala Asn Gly Glu Ala Val Tyr Cys Lys Phe His Tyr Lys Thr Asp Gln
225                 230                 235                 240

Gly Ile Lys Asn Leu Ser Val Glu Asp Ala Ala Arg Leu Ala His Glu
                245                 250                 255

Asp Pro Asp Tyr Gly Leu Arg Asp Leu Phe Asn Ala Ile Ala Thr Gly
            260                 265                 270

Asn Tyr Pro Ser Trp Thr Leu Tyr Ile Gln Val Met Thr Phe Ser Glu
        275                 280                 285
```

```
Ala Glu Ile Phe Pro Phe Asn Pro Phe Asp Leu Thr Lys Val Trp Pro
    290                 295                 300

His Gly Asp Tyr Pro Leu Ile Pro Val Gly Lys Leu Val Leu Asn Arg
305                 310                 315                 320

Asn Pro Val Asn Tyr Phe Ala Glu Val Glu Gln Leu Ala Phe Asp Pro
                325                 330                 335

Ser Asn Met Pro Pro Gly Ile Glu Pro Ser Pro Asp Lys Met Leu Gln
            340                 345                 350

Gly Arg Leu Phe Ala Tyr Pro Asp Thr His Arg His Arg Leu Gly Pro
        355                 360                 365

Asn Tyr Leu Gln Ile Pro Val Asn Cys Pro Tyr Arg Ala Arg Val Ala
370                 375                 380

Asn Tyr Gln Arg Asp Gly Pro Met Cys Met Met Asp Asn Gln Gly Gly
385                 390                 395                 400

Ala Pro Asn Tyr Tyr Pro Asn Ser Phe Ser Ala Pro Glu His Gln Pro
                405                 410                 415

Ser Ala Leu Glu His Arg Thr His Phe Ser Gly Asp Val Gln Arg Phe
            420                 425                 430

Asn Ser Ala Asn Asp Asp Asn Val Thr Gln Val Arg Thr Phe Tyr Leu
        435                 440                 445

Lys Val Leu Asn Glu Glu Gln Arg Lys Arg Leu Cys Glu Asn Ile Ala
450                 455                 460

Gly His Leu Lys Asp Ala Gln Leu Phe Ile Gln Lys Lys Ala Val Lys
465                 470                 475                 480

Asn Phe Ser Asp Val His Pro Glu Tyr Gly Ser Arg Ile Gln Ala Leu
                485                 490                 495

Leu Asp Lys Tyr Asn Glu Glu Lys Pro Lys Asn Ala Val His Thr Tyr
            500                 505                 510

Val Gln His Gly Ser His Leu Ser Ala Arg Glu Lys Ala Asn Leu
        515                 520                 525

<210> SEQ ID NO 21
<211> LENGTH: 531
<212> TYPE: PRT
<213> ORGANISM: Methylovorus sp. MUT

<400> SEQUENCE: 21

Met Thr Asp Thr Ile Phe Asp Tyr Val Ile Val Gly Gly Gly Thr Ala
1               5                   10                  15

Gly Ser Val Leu Ala Asn Arg Leu Ser Ala Arg Pro Glu Asn Arg Val
            20                  25                  30

Leu Leu Ile Glu Ala Gly Ile Asp Thr Pro Glu Asn Asn Ile Pro Pro
        35                  40                  45

Glu Ile His Asp Gly Leu Arg Pro Trp Leu Pro Arg Leu Ser Gly Asp
    50                  55                  60

Lys Phe Phe Trp Pro Asn Leu Thr Val Tyr Arg Ala Ala Glu His Pro
65                  70                  75                  80

Gly Ile Thr Arg Glu Pro Gln Phe Tyr Glu Gln Gly Arg Leu Leu Gly
                85                  90                  95

Gly Gly Ser Ser Val Asn Met Val Ser Asn Arg Gly Leu Pro Arg
            100                 105                 110

Asp Tyr Asp Glu Trp Gln Ala Leu Gly Ala Asp Gly Trp Asp Trp Gln
        115                 120                 125

Gly Val Leu Pro Tyr Phe Ile Lys Thr Glu Arg Asp Ala Asp Tyr Gly
    130                 135                 140
```

```
Asp Asp Pro Leu His Gly Asn Ala Gly Pro Ile Pro Ile Gly Arg Val
145                 150                 155                 160

Asp Ser Arg His Trp Ser Asp Phe Thr Val Ala Ala Thr Gln Ala Leu
            165                 170                 175

Glu Ala Ala Gly Leu Pro Asn Ile His Asp Gln Asn Ala Arg Phe Asp
        180                 185                 190

Asp Gly Tyr Phe Pro Pro Ala Phe Thr Leu Lys Gly Glu Glu Arg Phe
    195                 200                 205

Ser Ala Ala Arg Gly Tyr Leu Asp Ala Ser Val Arg Val Arg Pro Asn
210                 215                 220

Leu Ser Leu Trp Thr Glu Ser Arg Val Leu Lys Leu Leu Thr Thr Gly
225                 230                 235                 240

Asn Ala Ile Thr Gly Val Ser Val Leu Arg Gly Arg Glu Thr Leu Gln
            245                 250                 255

Val Gln Ala Arg Glu Val Ile Leu Thr Ala Gly Ala Leu Gln Ser Pro
        260                 265                 270

Ala Ile Leu Leu Arg Thr Gly Ile Gly Pro Ala Ala Asp Leu His Ala
    275                 280                 285

Leu Gly Ile Pro Val Leu Ala Asp Arg Pro Gly Val Gly Arg Asn Leu
290                 295                 300

Trp Glu His Ser Ser Ile Gly Val Val Ala Pro Leu Thr Glu Gln Ala
305                 310                 315                 320

Arg Ala Asp Ala Ser Thr Gly Lys Ala Gly Ser Arg His Gln Leu Gly
            325                 330                 335

Ile Arg Ala Ser Ser Gly Val Asp Pro Ala Thr Pro Ser Asp Leu Phe
        340                 345                 350

Leu His Ile His Ala Asp Pro Val Ser Gly Leu Ala Ser Ala Arg Phe
    355                 360                 365

Trp Val Asn Lys Pro Ser Ser Thr Gly Trp Leu Lys Leu Lys Asp Ala
370                 375                 380

Asp Pro Phe Ser Tyr Pro Asp Val Asp Phe Asn Leu Leu Ser Asp Pro
385                 390                 395                 400

Arg Asp Leu Gly Arg Leu Lys Ala Gly Leu Arg Leu Ile Lys His Tyr
            405                 410                 415

Phe Ala Tyr Pro Ser Leu Ala Lys Tyr Gly Leu Ala Leu Ala Leu Ser
        420                 425                 430

Arg Phe Glu Ala Pro Gln Pro Gly Gly Pro Leu Leu Asn Asp Leu Leu
    435                 440                 445

Gln Asp Glu Ala Ala Leu Glu Arg Tyr Leu Arg Thr Asn Val Gly Gly
450                 455                 460

Val Phe His Ala Ser Gly Thr Ala Arg Ile Gly Arg Ala Asp Asp Ser
465                 470                 475                 480

Gln Ala Val Val Asp Lys Ala Gly Arg Val Tyr Gly Val Thr Gly Leu
            485                 490                 495

Arg Val Ala Asp Ala Ser Ile Met Pro Thr Val Pro Thr Ala Asn Thr
        500                 505                 510

Asn Leu Pro Thr Leu Met Leu Ala Glu Lys Ile Ala Asp Ala Ile Leu
    515                 520                 525

Thr Gln Ala
530
```

ANAEROBIC FERMENTATIVE PRODUCTION OF FURANDIMETHANOL AND ENZYMATIC PRODUCTION OF FURANDICARBOXYLIC ACID

CROSS-REFERENCE TO RELATED APPLICATIONS

This application claims priority to U.S. Provisional Application No. 63/073,271 filed Sep. 1, 2020, entitled "ANAEROBIC FERMENTATIVE PRODUCTION OF FURANDIMETHANOL AND ENZYMATIC PRODUCTION OF FURANDICARBOXYLIC ACID," the disclosure of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 127125_5018_US_Sequence_Listing.txt. The text file is about 97 KB, was created on Sep. 1, 2021, and is being submitted electronically via EFS-Web.

BACKGROUND 2,5-Furandicarboxylic acid (2,5-FDCA) has gained much attention due to its potential of substituting terephthalic acid in the synthesis of polyesters, specially polyethylene terephthalate (PET) (Sousa, Andreia F., et al. "Biobased polyesters and other polymers from 2, 5-furandicarboxylic acid: a tribute to furan excellency." Polymer chemistry 6.33 (2015): 5961-5983). Substituting terephthalic acid to its furan analogue 2,5-FDCA in PET can lead to 2,5-furandicarboxylate (2,5-PEF) and this polymer has several advantages when compared to PET. In one aspect, 2,5-PEF has better thermal, barrier and mechanical properties when compared to its counterpart (PEP Report 294). Furthermore, as it is known that ethylene glycol could be produced from renewable resources, then 2,5-PEF could be 100% renewable as opposed to the semi-renewable PET.

Despite all the aforementioned advantages of 2,5-FDCA in comparison to terephthalic acid, 2,5-FDCA production cost is still a current limitation in expanding monomer usage. Existing technologies are not cost-competitive when compared to terephthalic acid. One of the possible reasons for this is related to the several sequential industrial steps required. One issue that could help reduce 2,5-FDCA production costs is finding a direct fermentation route from sugar to the desired molecule, but such a route has never been reported.

2,4-FDCA, an isomer of 2,5-FDCA, possesses unique properties compared to the well-studied 2,5-FDCA. Catalytically polymerizing 2,4-FDCA with a diol yields a polymer composed of 2,4-FDCA with valuable properties. In one study, Thiyagarajan and collaborators (2014) compare polyesters made of 2,4-FDCA, 3,4-FDCA, 2,5-FDCA and terephthalic acid and concluded that 2,4-FDCA and 3,4-FDCA polyesters can be made in sufficient molecular weights by industrially applicable methods (Thiyagarajan, Shanmugam, et al. "Biobased furandicarboxylic acids (FDCAs): effects of isomeric substitution on polyester synthesis and properties." Green Chemistry 16.4 (2014): 1957-1966). In another study, Thiyagarajan and colleagues concluded that structural analysis of 2,4-FDCA and 2,5-FDCA reveal that 2,4-FDCA possesses more linear characteristics resembling terephthalic acid than does 2,5-FDCA. These features make 2,4-FDCA an interesting monomer for synthetic polyesters (Thiyagarajan et al. "Concurrent formation of furan-2,5- and furan-2,4-dicarboxylic acid: unexpected aspects of the Henkel reaction" RSC Advances 3 (2013): 15678-15686). Further, these materials have properties unlike 2,5-FDCA polyesters (Bourdet et al. "Molecular Mobility in Amorphous Biobased Poly (ethylene 2, 5-furandicarboxylate) and Poly (ethylene 2, 4-furandicarboxylate)." Macromolecules 51.5 (2018): 1937-1945).

In certain cases, 2,4-FDCA polymers have been reported to have superior properties to those possessed by 2,5-FDCA polymers. Cui and collaborators (2016) report that the bond-angle between the double carboxyl groups linking with the central ring is a key factor that influences the stability of nematic liquid crystal molecules such as those utilized in LCD TVs, notebook computers, and other display elements (Cui, Min-Shu, et al. "Production of 4-hydroxymethylfurfural from derivatives of biomass-derived glycerol for chemicals and polymers." ACS Sustainable Chemistry & Engineering 4.3 (2016): 1707-1714). The first discovered liquid crystal, terephthalic acid diester molecules has a bond-angle between two carboxyl groups of 180°. In comparison, 2,5-furan dicarboxylic acid has a bond-angle between two carboxyl groups of 137°. Significantly, 2,4-furan dicarboxylic acid has a bond-angle between two carboxyl groups of 160° making it more suitable for synthesis of nematic liquid crystal molecules.

Despite these potential applications of 2,4-FDCA polymers, the production cost of 2,4-FDCA is a current bottleneck in expanding this monomer to the applications as described by Cui and collaborators (2016). Previous syntheses of 2,4-substituted furans, including 2,4-FDCA, required multiple synthetic steps and therefore 2,4-FDCA-derived polymers are cost-prohibitive by currently available methodologies and industrial techniques.

Another valuable furan-based industrial product is 2,4-furandimethanol (2,4-FDME). There is a need for more efficient and cost-effective production of both 2,4-FDME and 2,4-FDCA.

SUMMARY

The present disclosure provides direct and anaerobic fermentation pathways for 2,4-FDME production in a recombinant microorganism such as an ethanol-producing yeast. The pathways advantageously have a redox-cofactor balance and yield positive ATP by coupling FDME production with electron donating and ATP-positive pathways, thereby providing more efficient and cost-effective pathways for anaerobic 2,4-FDME production. Further, the present disclosure provides an enzymatic process for converting the 2,4-FDME produced according to the present disclosure into 2,4-FDCA, thereby providing more efficient and cost-effective pathways for 2,4-FDCA production.

The present disclosure provides a recombinant microorganism such as an ethanol-producing yeast comprising: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; and (d) at least one deletion of an enzyme in a glycerol-production pathway or at least one genetic modification that leads to a down-regulation of an enzyme in a glycerol-production pathway.

The present disclosure provides a recombinant microorganism that is an ethanol-producing yeast capable of producing 2,4-furandimethanol (2,4-FDME) and ethanol from a carbon source, wherein the recombinant microorganism expresses the following: (a) at least one exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; and wherein the recombinant microorganism has at least one genetic modification that leads to a deletion or a down-regulation of an enzyme in a glycerol-production pathway in the microorganism and wherein 2,4-FDME production totally or partially replaces glycerol as co-product.

In some embodiments, the polypeptide that catalyzes the production of 2,4-FDME from 4-HMF is a dehydrogenase. In some embodiments, the polypeptide that catalyzes the production of 2,4-FDME from 4-HMF is a NADH-consuming dehydrogenase. In some embodiments, the dehydrogenase is classified as EC number 1.1.1. In some embodiments, the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*. In some embodiments, the mutated alcohol dehydrogenase comprises one to six non-conservative amino acid substitution(s) at one or more of residues 59, 110, 117, 148, 152, or 295. In some embodiments, the mutated alcohol dehydrogenase comprises mutations S110P, L117S, and/or Y295C.

In some embodiments, the enzyme in the glycerol-production pathway is a glycerol-3-phosphate dehydrogenase. In some embodiments, the glycerol-3-phosphate dehydrogenase is classified as EC number 1.1.1.8 or EC number 1.1.5.3. In some embodiments, a GPD1 gene, a GPD2 gene, or both are deleted from the microorganism or down-regulated in the microorganism.

In some embodiments, the enzyme in the glycerol-production pathway is a glycerol-3-phosphate phosphatase. In some embodiments, the glycerol-3-phosphate phosphatase is classified as EC number 3.1.3.21.

In some embodiments, the enzyme in the glycerol-production pathway is GPD1, GPD2, glycerol-3-phosphate phosphatase, or a combination thereof.

In some embodiments, a GPD1 gene, a GPD2 gene, and a gene encoding a glycerol-3-phosphate phosphatase are deleted from the microorganism. In some embodiments, a GPD1 gene, a GPD2 gene, and a gene encoding a glycerol-3-phosphate phosphatase are down-regulated in the microorganism.

In some embodiments, the microorganism produces ethanol.

In some embodiments, the microorganism further contains at least one endogenous and/or exogenous nucleic acid molecule encoding one or more polypeptides that catalyze the production of NADH and $CO_2$ from externally added formate.

In some embodiments, the polypeptide that catalyzes the production of NADH and $CO_2$ from formate is a NAD$^+$-dependent formate dehydrogenase. In some embodiments, the NAD$^+$-dependent formate dehydrogenase is classified as EC number 1.2.1.2. In some embodiments, the microorganism converts externally provided formate to NADH and $CO_2$.

In some embodiments, the microorganism further contains: (i) at least one endogenous and/or exogenous nucleic acid molecule encoding one or more polypeptides that catalyze the production of 6-phospho-D-gluconate and NADPH from D-glucose-6-phosphate; and (ii) at least one endogenous and/or exogenous nucleic acid molecule encoding one or more polypeptides that catalyze the production of D-ribulose-5-phosphate, $CO_2$, and NADPH from 6-phospho-D-gluconate; and optionally further contains at least one endogenous and/or exogenous nucleic acid molecule encoding one or more polypeptides that catalyze NADPH-driven reduction of NAD(+).

In some embodiments, the polypeptide that catalyzes the NADPH-driven reduction of NAD(+) is a NAD(P)+ transhydrogenase. In some embodiments, the NAD(P)+ transhydrogenase is classified as EC number EC 1.6.1. In some embodiments, the transhydrogenase is selected from NAD(P)+ transhydrogenases (Si-specific) classified as EC number 1.6.1.1, NAD(P)+ transhydrogenase (Re/Si-specific) classified as EC number 1.6.1.2, NAD(P)+ transhydrogenases classified as EC number 1.6.1.3 and/or NAD(P)+ transhydrogenases (ferredoxin) classified as EC number 1.6.1.4.

In some embodiments, the recombinant microorganism further comprises at least one deletion of an enzyme in a pathway for converting fructose-6-phosphate and ATP to fructose-1,6-biphosphate. In some embodiments, the recombinant microorganism further comprises at least one genetic modification that leads to a down-regulation of an enzyme in a pathway for converting fructose-6-phosphate and ATP to fructose-1,6-biphosphate. In some embodiments, the enzyme in the pathway for converting fructose-6-phosphate and ATP to fructose-1,6-biphosphate is a phosphofructokinase.

The present disclosure provides a recombinant microorganism comprising: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; and (d) at least one endogenous and/or exogenous nucleic acid molecule encoding one or more polypeptides that catalyze the production of NADH and $CO_2$ from formate.

In some embodiments, the polypeptide that catalyzes the production of 2,4-FDME from 4-HMF is a dehydrogenase, preferably wherein the dehydrogenase is classified as EC number 1.1.1. In some embodiments, the polypeptide that catalyzes the production of 2,4-FDME from 4-HMF is a NADH-consuming dehydrogenase. In some embodiments, the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*. In some embodiments, the mutated alcohol dehydrogenase comprises one to six non-conservative amino acid substitution(s) at one or more of residues 59, 110, 117, 148, 152, or 295. In some embodiments, the mutated alcohol dehydrogenase comprises mutations S110P, L117S, and/or Y295C.

In some embodiments, the polypeptide that catalyzes the production of NADH and $CO_2$ from formate is a NAD$^+$-dependent formate dehydrogenase. In some embodiments, the NAD$^+$-dependent formate dehydrogenase is classified as EC number 1.2.1.2. In some embodiments, the microorganism converts externally provided formate to NADH and $CO_2$.

In some embodiments, the recombinant microorganism further comprises at least one deletion of an enzyme in a glycerol-production pathway. In some embodiments, the recombinant microorganism further comprises least one genetic modification that leads to a down-regulation of an enzyme in a glycerol-production pathway.

In some embodiments, the enzyme in the glycerol-production pathway is a glycerol-3-phosphate dehydrogenase. In some embodiments, the glycerol-3-phosphate dehydrogenase is classified as EC number 1.1.1.8 or EC number 1.1.5.3.

In some embodiments, a GPD1 gene, a GPD2 gene, or both are deleted from the microorganism. In some embodiments, a GPD1 gene, a GPD2 gene, or both are down-regulated in the microorganism.

In some embodiments, the enzyme in the glycerol-production pathway is a glycerol-3-phosphate phosphatase. In some embodiments, the glycerol-3-phosphate phosphatase is classified as EC number 3.1.3.21.

In some embodiments, the enzyme in the glycerol-production pathway is GPD1, GPD2, glycerol-3-phosphate phosphatase, or a combination thereof.

In some embodiments, a GPD1 gene, a GPD2 gene, and a gene encoding a glycerol-3-phosphate phosphatase are deleted from the microorganism. In some embodiments, a GPD1 gene, a GPD2 gene, and a gene encoding a glycerol-3-phosphate phosphatase are down-regulated in the microorganism.

In some embodiments, the microorganism produces ethanol.

The present disclosure provides a recombinant microorganism comprising: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; (d) at least one endogenous and/or exogenous nucleic acid molecule encoding a polypeptide that catalyzes the production of oxaloacetate from phosphoenol pyruvate (PEP); (e) at least one endogenous and/or exogenous nucleic acid molecule encoding one or more polypeptides that catalyze: (1) the production of malonate semialdehyde from oxaloacetate; and/or (2) the production of aspartate from oxaloacetate, the production of β-alanine from aspartate, and the production of malonate semialdehyde from β-alanine; and/or (3) the production of malonyl-CoA from malonate semialdehyde; and/or (4) the production of malonyl-CoA from oxaloacetate; and/or (f) at least one endogenous and/or exogenous nucleic acid molecule encoding one or more polypeptides that catalyze: (1) the production of acetyl-CoA from malonate semialdehyde, and the production of acetoacetyl-CoA from acetyl-CoA; and/or (2) the production of acetyl-CoA from malonyl-CoA, and the production of acetoacetyl-CoA from acetyl-CoA; and/or (3) the production of acetoacetyl-CoA from malonyl-CoA; and/or (g) at least one endogenous and/or exogenous nucleic acid molecule encoding one or more polypeptides that catalyze: (1) the production of acetoacetate from acetoacetyl-CoA; and/or (2) the production of HMG-CoA from acetoacetyl-CoA, and the production of acetoacetate from HMG-CoA; and (h) at least one endogenous and/or exogenous nucleic acid molecule encoding a polypeptide that catalyzes the production of acetone from acetoacetate.

In some embodiments, the polypeptide that catalyzes the production of 2,4-FDME from 4-HMF is a dehydrogenase. In some embodiments, the polypeptide that catalyzes the production of 2,4-FDME from 4-HMF is a NADH-consuming dehydrogenase. In some embodiments, the dehydrogenase is classified as EC number 1.1.1. In some embodiments, the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*. In some embodiments, the mutated alcohol dehydrogenase comprises one to six non-conservative amino acid substitution(s) at one or more of residues 59, 110, 117, 148, 152, or 295. In some embodiments, the mutated alcohol dehydrogenase comprises mutations S110P, L117S, and/or Y295C.

In some embodiments, the polypeptide that catalyzes the production of malonate semialdehyde from oxaloacetate is an oxaloacetate 1-decarboxylase (MSA forming).

In some embodiments, wherein the polypeptide that catalyzes the production of aspartate from oxaloacetate is an aspartate amino transferase. In some embodiments, the polypeptide that catalyzes the production of β-alanine from aspartate is an aspartate decarboxylase. In some embodiments, the polypeptide that catalyzes the production of malonate semialdehyde from β-alanine is a β-alanine pyruvate amino transferase and/or a β-alanine transaminase.

In some embodiments, the polypeptide that catalyzes the production of malonyl-CoA from malonate semialdehyde is a malonyl-CoA reductase and/or 2-keto acid decarboxylase.

In some embodiments, the polypeptide that catalyzes the production of malonyl-CoA from oxaloacetate is a malonyl-CoA synthetase.

In some embodiments, the polypeptide that catalyzes the production of acetyl-CoA from malonate semialdehyde is a malonate semialdehyde dehydrogenase.

In some embodiments, the polypeptide that catalyzes the production of acetoacetyl-CoA from acetyl-CoA is a thiolase and/or an acetyl-CoA acetyltransferase.

In some embodiments, the polypeptide that catalyzes the production of acetyl-CoA from malonyl-CoA is a malonyl-CoA decarboxylase.

In some embodiments, the polypeptide that catalyzes the production of acetoacetyl-CoA from malonyl-CoA is an acetoacetyl-CoA synthase.

In some embodiments, the polypeptide that catalyzes the production of acetoacetate from acetoacetyl-CoA is an acetoacetyl-CoA thioesterase and/or an acetoacetyl-CoA transferase.

In some embodiments, the polypeptide that catalyzes the production of HMG-CoA from acetoacetyl-CoA is a hydroxymethylglutaryl-CoA synthase.

In some embodiments, the polypeptide that catalyzes the production of acetoacetate from HMG-CoA is a hydroxymethylglutaryl-CoA lyase.

In some embodiments, the polypeptide that catalyzes the production of acetone from acetoacetate is an acetoacetate decarboxylase.

In some embodiments, the recombinant microorganism further comprises at least one endogenous and/or exogenous nucleic acid molecule encoding one or more polypeptides that catalyze the production of isopropanol from acetone.

In some embodiments, the polypeptide that catalyzes the production of isopropanol from acetone is an alcohol dehydrogenase.

In some embodiments, the microorganism produces ethanol.

The present disclosure provides a recombinant microorganism comprising: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; (d) at least one endogenous and/or exogenous nucleic acid molecule encoding one or more polypeptides that catalyze the production of 6-phospho-D-gluconate and NADPH from D-glucose-6-phosphate; and (e) at least one endogenous and/or exogenous nucleic acid molecule encoding one or more polypeptides that catalyze the production of D-ribulose-5-phosphate, $CO_2$, and NADPH from 6-phospho-D-gluconate.

In some embodiments, wherein the polypeptide that catalyzes the production of 2,4-FDME from 4-HMF is a dehydrogenase. In some embodiments, the polypeptide that catalyzes the production of 2,4-FDME from 4-HMF is a NADH-consuming dehydrogenase. In some embodiments, the dehydrogenase is classified as EC number 1.1.1. In some embodiments, the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*. In some embodiments, the mutated alcohol dehydrogenase comprises one to six non-conservative amino acid substitution(s) at one or more of residues 59, 110, 117, 148, 152, or 295. In some embodiments, the mutated alcohol dehydrogenase comprises mutations S110P, L117S, and/or Y295C.

In some embodiments, the polypeptides that catalyze the production of 6-phospho-D-gluconate and NADPH from D-glucose-6-phosphate are a glucose-6-phosphate dehydrogenase and a gluconolactonase.

In some embodiments, the polypeptide that catalyzes the production of D-ribulose-5-phosphate, $CO_2$, and NADPH from 6-phospho-D-gluconate is a 6-phosphogluconate dehydrogenase.

In some embodiments, the microorganism further comprises at least one endogenous and/or exogenous nucleic acid molecule encoding one or more polypeptides that catalyze NADPH-driven reduction of NAD(+).

In some embodiments, the polypeptide that catalyzes the NADPH-driven reduction of NAD(+) is a NAD(P)+ transhydrogenase. In some embodiments, the NAD(P)+ transhydrogenase is classified as EC number EC 1.6.1. In some embodiments, the transhydrogenase is selected from NAD(P)+ transhydrogenases (Si-specific) classified as EC number 1.6.1.1, NAD(P)+ transhydrogenases (Re/Si-specific) classified as EC number 1.6.1.2, NAD(P)+ transhydrogenases classified as EC number 1.6.1.3 and/or NAD(P)+ transhydrogenases (ferredoxin) classified as EC number 1.6.1.4.

In some embodiments, the recombinant microorganism further comprises at least one deletion of an enzyme in a pathway for converting fructose-6-phosphate and ATP to fructose-1,6-biphosphate. In some embodiments, the recombinant microorganism further comprises at least one genetic modification that leads to a down-regulation of an enzyme in a pathway for converting fructose-6-phosphate and ATP to fructose-1,6-biphosphate. In some embodiments, the enzyme in the pathway for converting fructose-6-phosphate and ATP to fructose-1,6-biphosphate is a phosphofructokinase.

In some embodiments, the microorganism produces ethanol.

In some embodiments, the microorganism is selected from a bacterium, a fungus, or a yeast. In some embodiments, the microorganism is a yeast. In some embodiments, the microorganism is *Saccharomyces cerevisiae*. In some embodiments, the microorganism is selected from *Saccharomyces* spp., *Saccharomyces cerevisiae*, *Candida krusei*, *Issatchenkia* spp., *Issatchenkia orientalis*, *Hansenula* spp., *Debaryomyces* spp., *Rhodotula* spp., *Pachysolen* spp., *Cryptococcus* spp., *Trichosporon* spp., *Myxozyma* spp., *Candida* spp., *Kluyveromyces* spp., *Pichia* spp., *Pichia* kudriavzevii, *Schizosaccharomyces* spp., *Torulaspora* spp., *Zygosaccharomyces* spp., *Yarrowia* spp., *Yarrowia lipolytica*, *Scheffersomyces* spp., or *Scheffersomyces stipitis*.

The present disclosure provides a method of co-producing 2,4-FDME and ethanol comprising: contacting the recombinant microorganism as disclosed herein, such as the recombinant ethanol-producing yeast as disclosed herein, with a fermentable carbon source under conditions sufficient to produce 2,4-FDME and ethanol. In some embodiments, the fermentable carbon source comprises a hexose, a pentose, glycerol, $CO_2$, sucroses or combinations thereof. In some embodiments, the fermentable carbon source further comprises formate as a co-substrate. In some embodiments, the method further produces acetone. In some embodiments, the method microorganism further produces isopropanol. In some embodiments, the conditions comprise anaerobic conditions. In some embodiments, the 2,4-FDME and ethanol are coproduced under anaerobic or microaerobic conditions.

The present disclosure provides a method of producing 2,4-furandicarboxylic acid (2,4-FDCA), the method comprising: (i) contacting the recombinant microorganism as disclosed herein, such as the recombinant ethanol-producing yeast as disclosed herein, with a fermentable carbon source under conditions sufficient to produce 2,4-FDME and ethanol; and (ii) converting the 2,4-FDME to 2,4-FDCA. In some embodiments, the converting step (ii) comprises enzymatically converting the 2,4-FDME to 2,4-FDCA with one or more oxidases or oxidative enzymes. In some embodiments, the converting step (ii) comprises converting the 2,4-FDME to 2,4-FDCA by the same ethanol-producing yeast or by another microorganism in a vessel in the presence of a sufficient amount of oxygen to convert the 2,4-FDME to 2,4-FDCA, wherein the microorganism expresses necessary amounts of the oxidative enzymes needed for 2,4-FDME oxidation into 2,4-FDCA. In some embodiments, enzymatically converting the 2,4-FDME to 2,4-FDCA is performed in a vessel substantially free of microorganisms and in the presence of a sufficient amount of oxygen to enzymatically convert the 2,4-FDME to 2,4-FDCA.

The present disclosure provides a method of producing 2,4-furandicarboxylic acid (2,4-FDCA), the method comprising: enzymatically converting 2,4-FDME to 2,4-FDCA with one or more oxidases, one or more laccases, one or more lipases, and/or one or more dehydrogenases, including combinations of oxidases, laccases, lipases, and/or dehydrogenases, either directly or through production of one or more intermediates selected from 5-(hydroxymethyl)-3-furaldehyde, 4-(hydroxymethyl)furfural, 5-(hydroxymethyl)furan-3-carboxylic acid, 2,4-furandicarbaldehyde, 4-(hydroxymethyl)-2-furancarboxylic acid, 5-formyl-3-furoic acid, or 4-formyl-2-furoic acid. In some embodiments, the oxidase is classified as EC number 1.1.3.-. In some embodiments, the oxidase is classified as EC number 1.1.3.47, EC number 1.1.3.7, EC number 1.1.3.9, and/or EC number 1.1.3.22 (i.e., EC number 1.17.3.2). In some embodiments, the laccase is classified as EC number 1.10.3.-. In some embodiments, the lipase is classified as EC number 3.1.1.-. In some embodiments, the dehydrogenase is classified as EC number 1.1.1.-. In some embodiments, the dehydrogenase is classified as EC number 1.1.1.1. In some embodiments, enzymatically converting 2,4-FDME to 2,4-FDCA is performed in a vessel substantially free of microorganisms. In some embodiments, enzymatically converting 2,4-FDME to 2,4-FDCA is performed by a microorganism. In some embodiments, the method further comprises converting $H_2O_2$ to oxygen and water with a catalase, peroxidase, and/or peroxygenase. In some embodiments, the catalase or peroxidase is classified as EC number 1.11.1.-, and/or the peroxygenase is classified as EC number 1.11.2.-. In some embodiments, the 2,4-FDME for use in the production of 2,4-FDCA is produced by the recombinant microorganisms as disclosed herein. In some embodiments, the 2,4-FDME for use in the production of 2,4-FDCA is produced by the methods as disclosed herein.

The present disclosure provides a method of producing a polymer from 2,4-FDCA produced by the methods as disclosed herein, wherein the 2,4-FDCA and a diol are catalytically polymerized in a non-biological process. In some embodiments, the diol is selected from ethylene glycol, 1,3-propanediol, 1,2-propanediol, 1,4-butanediol, 1,3-butanediol, 2,3-butanediol, 1,5-pentanediol, or 1,6-hexanediol.

BRIEF DESCRIPTION OF THE DRAWINGS

FIG. 5A is a scheme depicting Construct 1. FIG. 5B is a scheme depicting Construct 2. FIG. 5C is a scheme depicting Construct 3. FIG. 5D is a scheme depicting Construct 5.

DETAILED DESCRIPTION

Figure 1A:
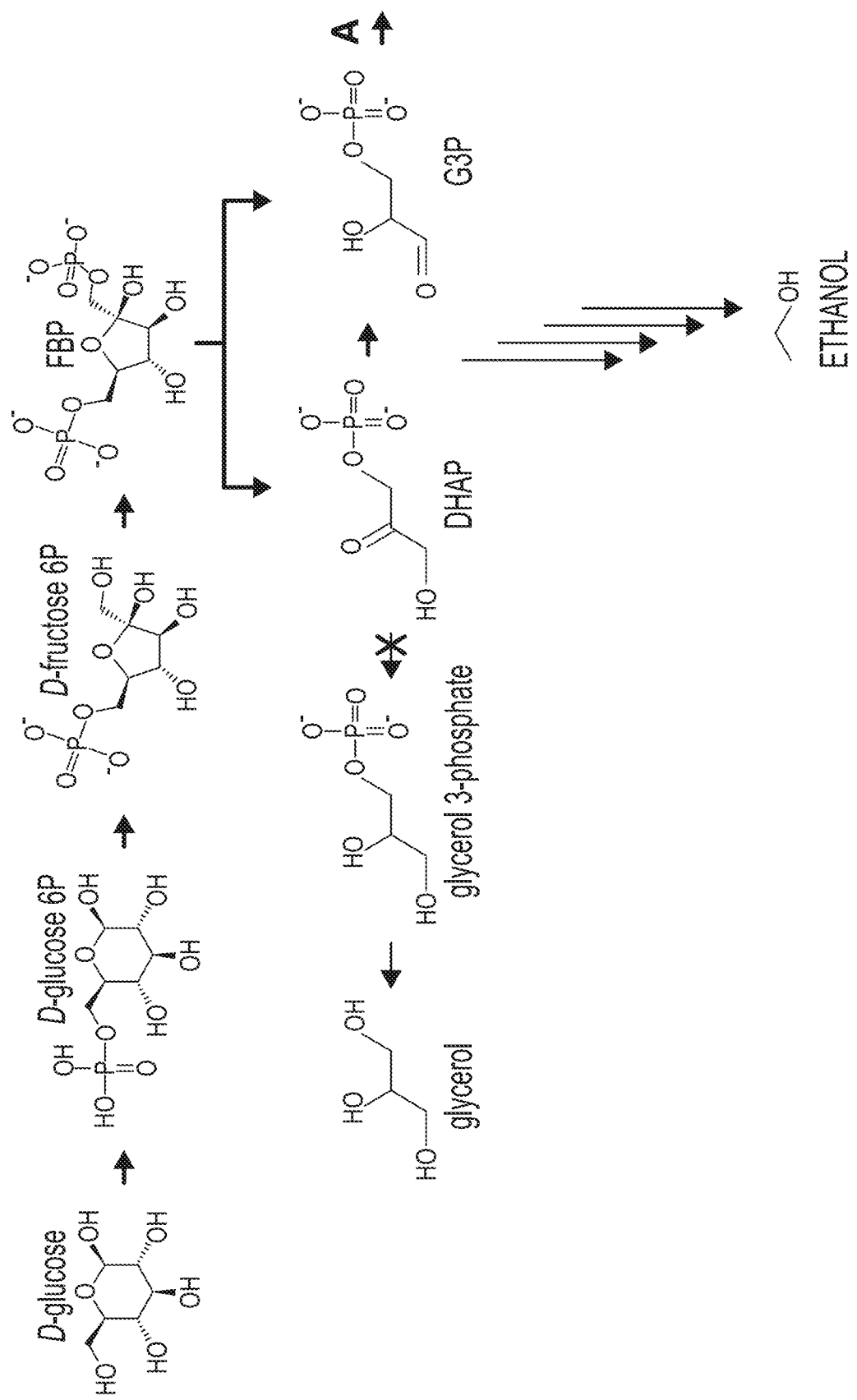
FIG. 1A-1B are schematic overviews of a biosynthetic pathway utilized by recombinant microorganisms of the disclosure for 2,4-FDME and ethanol production.

The present disclosure provides a direct and anaerobic fermentation route to 2,4-FDME in a recombinant microorganism. The direct and anaerobic fermentation of 2,4-FDME from a carbon feedstock enables the production of novel chemicals, solvents and polymers with commercial applicability on an industrial scale. By utilizing the anaerobic pathways disclosed herein, more efficient and cost-effective 2,4-FDME production can be achieved compared to an aerobic pathway.

Fermentative production of 2,4-FDME from a carbon feedstock can be achieved by a pathway involving conversion of glyceraldehyde-3-phosphate (G3P) into (5-formylfuran-3-yl)methyl phosphate, conversion of (5-formylfuran-3-yl)methyl phosphate into 4-hydroxymethylfurfural (4-HMF), and conversion of 4-HMF into 2,4-FDME by dehydrogenases. The foregoing pathway is net ATP negative (negative two molecules of ATP per one molecule of 2,4-FDME) and NADH negative according to Equation 1.

1 glucose+1 $NADH^+$ → 1 2,4-FDME−2 ATP+1 $NAD^+$     Equation 1:

Redox-cofactor balance and positive ATP yields are key requirements for viable anaerobic fermentation processes. Thus, microorganisms that are unable to provide redox-cofactor balance among different metabolic pathways and/or that lack positive ATP yields typically demonstrate poor or no ability to grow under anaerobic fermentation conditions.

As an example, glycerol is a well described required end-product of yeast ethanolic fermentation due to its redox imbalance in anaerobic fermentations. During anaerobic growth on carbohydrates, glycerol production functions as an electron sink to offset cell biomass formation so that overall redox neutrality is conserved (i.e., NAD+ is reduced to NADH at biomass formation and NADH is oxidized to NAD+ by glycerol production). While this is essential from a theoretical consideration of conservation of mass, in practice this has the effect that strains unable to produce glycerol (i.e., unable to use glycerol production as electron sink) are unable (or only very poorly able) to grow under the anaerobic conditions industrially used for ethanol production. Under anaerobic conditions, glycerol typically accounts for 4-10% of the total sugar consumption.

The present disclosure provides a recombinant ethanol-producing yeast capable of producing 2,4-furandimethanol (2,4-FDME) and ethanol from a carbon source, wherein the production of glycerol, a low value chemical, is partially or completely replaced by 2,4-FDME. Therefore, the present disclosure provides redox-cofactor balanced and positive ATP-yielding coupled pathways for anaerobic production of 2,4-FDME and high value chemicals such as ethanol. Thus, the present disclosure provides pathways and microorganisms where the 2,4-FDME pathway is coupled with electron donating pathways (for redox balance) and with the canonical ethanol production pathway in a glycerol-null yeast for ATP surplus (equation 2), enabling an anaerobic high yield production of 2,4-FDME and high value chemicals.

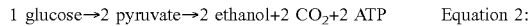

1 glucose→2 pyruvate→2 ethanol+2 $CO_2$+2 ATP    Equation 2:

The present disclosure also provides a method of enzymatically converting fermentatively produced 2,4-FDME to 2,4-FDCA.

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganism is a eukaryotic microorganism. In some embodiments, the eukaryotic microorganism is a yeast. In some embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Torulaspora, Rhodotorula, Scheffersomyces* and *Myxozyma*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. It is understood that the terms "recombinant microorganism" and "recombinant host cell" refer not only to the particular recombinant microorganism but to the progeny or potential progeny of such a microorganism.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "decreasing" or "reducing" the level of expression of a gene or an enzyme activity refers to the partial or complete suppression of the expression of a gene or enzyme activity. This suppression of expression or activity can be either an inhibition of the expression of the gene, a deletion of all or part of the promoter region necessary for the gene expression, a deletion in the coding region of the gene, or the replacement of the wild-type promoter by a weaker natural or synthetic promoter. For example, a gene may be completely deleted and may be replaced by a selection marker gene that facilitates the identification, isolation and purification of the strains according to the present disclosure. Alternatively, endogenous genes may be knocked out or deleted to favor the new metabolic pathway. In yet another embodiment, the expression of the gene may be decreased or reduced by using a weak promoter or by introducing certain mutations.

As used herein, the term "non-naturally occurring," when used in reference to a microorganism or enzyme activity of the disclosure, is intended to mean that the microorganism or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

The term "yield potential" or as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balance" refers to the overall amount of redox cofactors in a given set of reactions. When there is a shortage of redox cofactors, the redox balance is negative and the yield of such pathway would not be realistic since there is a need to burn feedstock to fulfill the cofactor demand. When there is a surplus of redox cofactors, the redox balance is said to be positive and the yield of such pathway is lower than the maximum yield (Dugar et al. "Relative potential of biosynthetic pathways for biofuels and bio-based products" Nature biotechnology 29.12 (2011): 1074). In addition, when the pathway produces the same amount of redox cofactors as it consumes, the redox balance is zero and one can refer to this pathway as "redox balanced." Designing metabolic pathways and engineering an organism such that the redox cofactors are balanced or close to being balanced usually results in a more efficient, higher yield production of the desired compounds when compared to an unbalanced pathway. Redox reactions occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. The term redox state is often used to describe the balance of NAD+/NADH and NADP+/NADPH of natural or non-natural metabolic pathways in a biological system such as a microbial cell. The redox state is reflected in the balance of several sets of metabolites (e.g., lactate and pyruvate, beta-hydroxybutyrate, and acetoacetate), whose interconversion is dependent on these ratios. In one embodiment, an external source of hydrogen or electrons, combined or not with the use of hydrogenase enzymes able to convert hydrogen to NAD(P)H, may be beneficial to increase product yield in metabolic pathways with negative redox balance, i.e., when there is a shortage in redox cofactors, such as NAD(P)H.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

The term "biologically pure culture" or "substantially pure culture" refers to a culture of a bacterial species described herein containing no other bacterial species in quantities sufficient to interfere with the replication of the culture or be detected by normal bacteriological techniques.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "catalytically polymerized" as used herein refers to polymerization process wherein monomers of the disclosure are polymerized in a non-biological or non-in vivo context.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, stored, or transferred, which does not detrimentally effect the microbe.

As used herein, the term "productivity" refers to the total amount of bioproduct, such as 2,4-FDME or 2,4-FDCA, produced per hour.

As used herein, "anaerobic" when used in reference to a culture or growth condition is intended to mean that the amount of oxygen is less than about 0% saturation of dissolved oxygen in liquid media. The term is also intended to include sealed chambers of liquid or solid media maintained with an atmosphere of less than about 0% oxygen. Anaerobic conditions also include conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of fermentation until oxygen is unavailable to the microorganism as a terminal electron acceptor.

As used herein, the term "aerobic" when used in reference to a culture or growth condition is intended to mean that the amount of oxygen is greater than about 10% of saturation for dissolved oxygen in liquid media. The term is also intended to include sealed chambers of liquid or solid media maintained with an atmosphere of about 10% oxygen to about 21% oxygen (as found in the atmosphere at sea level).

As used herein, the term "microaerobic" when used in reference to a culture or growth condition is intended to mean that the amount of oxygen is present in subsaturating amounts between anaerobic and aerobic conditions, wherein aerophilic microorganisms are capable of being sustained without an anoxic die off of the aerophilic microorganisms, the term "microaerobic" when used in reference to a culture or growth condition is intended to mean that the amount of oxygen is between 0% and 10% of saturation for dissolved oxygen in liquid media. The term is also intended to include sealed chambers of liquid or solid media maintained within a flow of oxygen that is utilized at about the same rate as it is provided without achieving aerobic conditions.

Recombinant Microorganisms

In some embodiments, the present disclosure provides a recombinant yeast capable of anaerobically co-producing 2,4-FDME and ethanol, by replacing glycerol formation as the predominant redox sink in anaerobic yeast metabolism with 2,4-FDME production. In some embodiments, the present disclosure provides a recombinant microorganism capable of anaerobically co-producing 2,4-FDME, ethanol, and acetone and/or isopropanol.

In some embodiments, the recombinant microorganism converts a carbon source to glyceraldehyde 3-phosphate (G3P). G3P is a common natural intermediary metabolite. In some embodiments, G3P can be produced from glucose via the glycolysis pathway or from xylose (e.g., from the pentose phosphate pathway) or from glycerol. In some embodiments, the recombinant microorganism capable of anaerobically producing 2,4-FDME utilizes a carbon source that comprises a monosaccharide (e.g., a hexose or a pentose), or glycerol. In some embodiments, the recombinant microorganism utilizes a further carbon source that is a one-carbon compound such as formate. In some embodiments, the recombinant microorganism comprises the capacity to anaerobically convert G3P to 2,4-FDME via several enzymatically-catalyzed successive steps.

In some embodiments, the recombinant microorganisms of the present disclosure are fungi.

In some embodiments, the recombinant microorganism is a eukaryotic microorganism. In some embodiments, the eukaryotic microorganism is a yeast. In some embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Torulaspora, Rhodotorula, Scheffersomyces* and *Myxozyma*. In some embodiments, the yeast is selected from *Saccharomyces* spp., *Saccharomyces cerevisiae, Candida krusei, Issatchenkia* spp., *Issatchenkia orientalis, Hansenula* spp., *Debaryomyces* spp., *Rhodotula* spp., *Pachysolen* spp., *Cryptococcus* spp., *Trichosporon* spp., *Myxozyma* spp., *Candida* spp., *Kluyveromyces* spp., *Pichia* spp., *Pichia kudriavzevii, Schizosaccharomyces* spp., *Torulaspora* spp., *Zygosaccharomyces* spp., *Yarrowia* spp., *Yarrowia lipolytica, Scheffersomyces* spp., or *Scheffersomyces stipitis*.

4-HMF

In some embodiments, the present disclosure comprises recombinant microorganisms and related methods for: (1) converting one or more carbon sources to glyceraldehyde 3-phosphate (G3P); (2) converting G3P to (5-formylfuran-3-yl)methyl phosphate (also known as 4-hydroxymethylfurfural phosphate); and (3) converting (5-formylfuran-3-yl) methyl phosphate to 4-hydroxymethylfurfural (4-HMF). In some embodiments, the one or more carbon sources are selected from glycerol, a monosaccharide, or a combination thereof.

In some embodiments, the recombinant microorganism of any one of the embodiments disclosed herein comprises at least one endogenous and/or exogenous nucleic acid molecule encoding one or more polypeptides capable of converting a carbon source to glyceraldehyde 3-phosphate (G3P). In some embodiments, glycerol is converted to glycerol-3-phosphate by at least one endogenous or exogenous glycerol kinase. In some embodiments, glycerol-3-phosphate is converted to dihydroxyacetone phosphate (DHAP) by at least one endogenous or exogenous glycerol-3-phosphate dehydrogenase. In some embodiments, glycerol is converted to dihydroxyacetone by at least one endogenous or exogenous glycerol dehydrogenase. In some embodiments, dihydroxyacetone is converted to dihydroxyacetone phosphate (DHAP) by at least one endogenous or exogenous dihydroxyacetone kinase. In some embodiments, DHAP is converted to G3P by at least one endogenous or exogenous triose phosphate isomerase. See Zhang et al. (2010. Applied and Environmental Microbiology, 76.8:2397-2401) for exemplary, but non-limiting, glycerol assimilation pathways contemplated herein.

In some embodiments, the recombinant microorganism of any one of the embodiments of disclosed herein comprises at least one endogenous or exogenous nucleic acid molecule encoding a (5-formylfuran-3-yl)methyl phosphate synthase that catalyzes the conversion of G3P to (5-formylfuran-3-yl)methyl phosphate. In some embodiments, the (5-formylfuran-3-yl)methyl phosphate synthase is classified as EC number 4.2.3.153. In some embodiments the EC 4.2.3.153 (5-formylfuran-3-yl)methyl phosphate synthase can be derived from the gene mfnB. In some embodiments, mfnB can be derived from *Methanocaldococcus jannaschii*. In some embodiments, EC 4.2.3.153 can be derived from homologs of mfnB.

In some embodiments, the recombinant microorganism of any one of the embodiments disclosed herein comprises at least one endogenous or exogenous nucleic acid molecule encoding a phosphatase or a kinase that catalyzes the conversion of (5-formylfuran-3-yl)methyl phosphate to (4-HMF). In some embodiments, the phosphatase is classified as EC number 3.1.3. In some embodiments, the phosphatase EC number 3.1.3 is selected from alkaline phosphatase (EC number 3.1.3.1), acid phosphatase (EC number 3.1.3.2), fructose-bisphosphatase (EC number 3.1.3.11), sugar-phosphatase (EC number 3.1.3.23), or sugar-terminal-phosphatase (EC number 3.1.3.58). In some embodiments, the kinase is classified as EC number 2.7.1. In some embodiments, the kinase EC number 2.7.1 is selected from fructokinase (EC number 2.7.1.4), ribokinase (EC number 2.7.1.15), ribulokinase (EC number 2.7.1.16), xylulokinase (EC number 2.7.1.17), or D-ribulokinase (EC number 2.7.1.47).

Thus, in some embodiments, the recombinant microorganism comprises at least one endogenous and/or exogenous nucleic acid molecule encoding polypeptides capable of converting a carbon source to glyceraldehyde 3-phosphate (G3P); at least one endogenous or exogenous nucleic acid molecule encoding a (5-formylfuran-3-yl)methyl phosphate synthase that catalyzes the conversion of G3P to (5-formylfuran-3-yl)methyl phosphate; and at least one endogenous or exogenous nucleic acid molecule encoding a phosphatase or a kinase that catalyzes the conversion of (5-formylfuran-3-yl)methyl phosphate to 4-HMF. Additional suitable enzymes for converting a carbon source to G3P, G3P to (5-formylfuran-3-yl)methyl phosphate, and (5-formylfuran-3-yl)methyl phosphate to 4-hydroxymethylfurfural (4-HMF) are disclosed in U.S. Patent Application Publication No. 2020/0277639.

2,4-FDME

In some embodiments, the present disclosure comprises recombinant microorganisms and related methods for converting one or more carbon sources to 2,4-furandimethanol (2,4-FDME).

In some embodiments, the recombinant microorganism of any one of the embodiments disclosed herein comprises at least one endogenous and/or exogenous nucleic acid molecule encoding one or more polypeptides capable of converting G3P to 2,4-FDME via several enzymatically-catalyzed successive steps as described herein. In some embodiments, the recombinant microorganism of any one of the embodiments disclosed herein comprises at least one endogenous and/or exogenous nucleic acid molecule encoding one or more polypeptides capable of converting 4-HMF to 2,4-FDME. In some embodiments, the polypeptide capable of converting 4-HMF to 2,4-FDME is a dehydrogenase. In some embodiments, the polypeptide that catalyzes the production of 2,4-FDME from 4-HMF is a NADH-consuming dehydrogenase. In some embodiments, the dehydrogenase is classified as EC number 1.1.1. In some embodiments, the dehydrogenase EC number 1.1.1 is selected from alcohol dehydrogenase (EC number 1.1.1.1), alcohol dehydrogenase (NADP+) (EC number 1.1.1.2), D-xylose reductase (EC number 1.1.1.307), aryl-alcohol dehydrogenase (EC number 1.1.1.90), aryl-alcohol dehydrogenase (EC number 1.1.1.91), and/or a mutated alcohol dehydrogenase 1 from *Saccharomyces cerevisiae*.

In some embodiments, the mutated alcohol dehydrogenase comprises one to six (e.g., one, two, three, four, five, or six) non-conservative amino acid substitution(s) at one or more of residues 59, 110, 117, 148, 152, or 295, based on the Adh1 sequence available as Uniprot number P00330. In some embodiments, the mutated alcohol dehydrogenase comprises mutations S110P, L117S, Y295C, or a combination thereof. See Laadan, Yeast, 25(3):191-198 (2008).

2,4-FDME Production With Modification of Glycerol Production

Glycerol is a low value chemical that is the main by-product of ethanol production by anaerobic fermentation by *Saccharomyces cerevisiae* and other ethanol producing yeasts. The diversion of sugar to glycerol production negatively impacts ethanol yield and process economy. In anaerobic, ethanol-producing cultures of *S. cerevisiae*, excess of NADH, generated from biosynthetic reactions, is reoxidized by reducing part of the sugar substrate to glycerol, according to equations 3 and 4:

1 glucose→2 DHAP            Equation 3:

1 DHAP+NADH→glycerol+NAD+            Equation 4:

In some embodiments, the present disclosure comprises recombinant microorganisms and related methods for anaerobically converting one or more carbon sources to 2,4-furandimethanol (2,4-FDME) and ethanol.

In some embodiments, the 2,4-FDME pathway disclosed herein is coupled to the ethanol production pathway (e.g., the canonical ethanol production pathway in yeast) to provide ATP surplus. In some embodiments, the coupled pathways disclosed herein provide anaerobic production of 2,4-FDME, more efficiently and more cost-effectively than aerobic pathways for 2,4-FDME production. Coupling 2,4-FDME and ethanol production further advantageously enables production of 2,4-FDME with an economically valuable chemical.

In some embodiments, a NADH consuming 2,4-FDME pathway disclosed herein is coupled to the deletion of an enzyme in a glycerol-production pathway and/or a genetic modification that leads to a down-regulation of an enzyme in a glycerol-production pathway. In some embodiments, coupling of the pathway with an ethanol production pathway (e.g., the canonical ethanol production pathway in yeast) provides ATP surplus.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDME via several enzymatically-catalyzed successive steps as described herein; and (2) at least one deletion of an enzyme in a glycerol-production pathway or at least one genetic modification that leads to a down-regulation of an enzyme in a glycerol-production pathway.

In some embodiments, the enzyme in the glycerol-production pathway is a glycerol-3-phosphate dehydrogenase. In some embodiments, the glycerol-3-phosphate dehydrogenase is classified as EC number 1.1.1.8 or EC number 1.1.5.3. In some embodiments, a GPD1 gene, a GPD2 gene, or both are deleted from the microorganism. In some embodiments, a GPD1 gene, a GPD2 gene, or both are down-regulated in the microorganism. In some embodiments, a GPD1 gene is deleted from the microorganism and a GPD2 gene is down-regulated in the microorganism. In some embodiments, a GPD1 gene is down-regulated in the microorganism and a GPD2 gene is deleted from the microorganism.

In some embodiments, the enzyme in the glycerol-production pathway is a glycerol-3-phosphate phosphatase. In some embodiments, the glycerol-3-phosphate phosphatase is classified as EC number 3.1.3.21.

In some embodiments, the enzyme in the glycerol-production pathway is GPD1, GPD2, glycerol-3-phosphate phosphatase, or a combination thereof.

In some embodiments, a GPD1 gene, a GPD2 gene, and a gene encoding a glycerol-3-phosphate phosphatase are deleted from the microorganism or down-regulated in the microorganism. In some embodiments, a GPD1 gene, a GPD2 gene, and a gene encoding a glycerol-3-phosphate phosphatase are deleted from the microorganism. In some embodiments, a GPD1 gene, a GPD2 gene, and a gene encoding a glycerol-3-phosphate phosphatase are down-regulated in the microorganism. In some embodiments, one of a GPD1 gene, a GPD2 gene, and a gene encoding a glycerol-3-phosphate phosphatase are deleted from the microorganism and the other two of the GPD1 gene, the GPD2 gene, and the gene encoding a glycerol-3-phosphate phosphatase are down-regulated in the microorganism. In some embodiments, one of a GPD1 gene, a GPD2 gene, and a gene encoding a glycerol-3-phosphate phosphatase are down-regulated in the microorganism and the other two of the GPD1 gene, the GPD2 gene, and the gene encoding a glycerol-3-phosphate phosphatase are deleted from the microorganism.

Figure 1B:
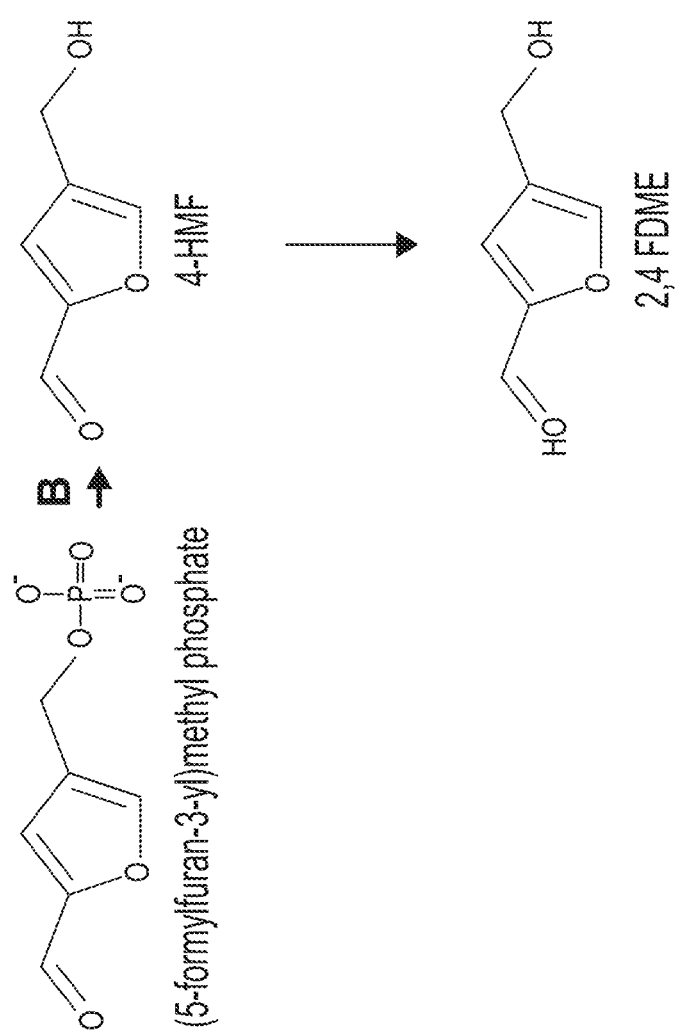

Some embodiments of the present disclosure are shown in FIG. 1, which schematically depicts the anaerobic biosynthetic conversion of a carbon feedstock (e.g., glucose) to 2,4-FDME and ethanol, wherein the GPD1 and GPD2 isoforms of yeast NAD-dependent glycerol-3-phosphate dehydrogenase are deleted.

The present disclosure is also directed to methods of co-producing 2,4-FDME and ethanol. In some embodiments, a method of co-producing 2,4-FDME and ethanol comprises: contacting a recombinant microorganism as described herein with a fermentable carbon source under conditions sufficient to produce 2,4-FDME and ethanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDME is produced in the absence of oxygen.

In some embodiments, the methods of co-producing 2,4-FDME and ethanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); and (c) converting 4-HMF to 2,4-furandimethanol (2,4-FDME); wherein the microorganism comprises at least one deletion of an enzyme in a glycerol-production pathway or at least one genetic modification that leads to a down-regulation of an enzyme in a glycerol-production pathway. In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-FDME with a dehydrogenase.

The present disclosure includes a method of producing a recombinant microorganism capable of producing 2,4-FDME, the method comprising introducing into and/or overexpressing in the recombinant microorganism the following: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; and (d) at least one deletion of an enzyme in a glycerol-production pathway or at least one genetic modification that leads to a down-regulation of an enzyme in a glycerol-production pathway.

Coupling 2,4-FDME Production with Formate Oxidation

In some embodiments, the present disclosure comprises recombinant microorganisms and related methods for anaerobically converting one or more carbon sources to 2,4-furandimethanol (2,4-FDME) and ethanol. In some embodiments, the carbon source further contains formate.

In some embodiments, the 2,4-FDME pathway disclosed herein is coupled to ethanol production pathway (e.g., the canonical ethanol production pathway in yeast) to provide ATP surplus. In some embodiments, the coupled pathways disclosed herein provide anaerobic production of 2,4-FDME, more efficiently and more cost-effectively than aerobic pathways for 2,4-FDME production. Coupling 2,4-FDME and ethanol production further advantageously enables production of 2,4-FDME with an economically valuable chemical.

In some embodiments, formate is utilized as a co-substrate in the carbon feedstock. In some embodiments, an endogenous NAD-dependent formate dehydrogenase (FDH) in *Saccharomyces cerevisiae* catalyzes the oxidation of formate to carbon dioxide, with donation of electrons to NADH according to equation 5:

$$\text{formate} + \text{NAD}^+ \rightarrow \text{CO}_2 + \text{NADH} + \text{H}^+ \qquad \text{Equation 5:}$$

In some embodiments, a NADH/NADPH-consuming 2,4-FDME pathway disclosed herein is coupled to formate oxidation to $CO_2$. In some embodiments, coupling of the pathway with an ethanol production pathway (e.g., the canonical ethanol production pathway in yeast) provides ATP surplus.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDME via several enzymatically-catalyzed successive steps as described herein; and (2) at least one endogenous and/or exogenous nucleic acid molecule encoding one or more polypeptides that catalyze the production of NADH and $CO_2$ from formate.

In some embodiments, the polypeptide that catalyzes the production of NADH and $CO_2$ from formate is a $NAD^+$-dependent formate dehydrogenase. In some embodiments, the $NAD^+$-dependent formate dehydrogenase is classified as EC number 1.2.1.2. In some embodiments, the microorganism converts externally provided formate to NADH and $CO_2$. In some embodiments, the formate is supplied in the fermentation medium.

In some embodiments, the recombinant microorganism comprises at least one deletion of an enzyme in a glycerol-production pathway or at least one genetic modification that leads to a down-regulation of an enzyme in a glycerol-production pathway.

In some embodiments, the enzyme in the glycerol-production pathway is a glycerol-3-phosphate dehydrogenase. In some embodiments, the glycerol-3-phosphate dehydrogenase is classified as EC number 1.1.1.8 or EC number 1.1.5.3. In some embodiments, a GPD1 gene, a GPD2 gene, or both are deleted from the microorganism. In some embodiments, a GPD1 gene, a GPD2 gene, or both are down-regulated in the microorganism. In some embodiments, a GPD1 gene is deleted from the microorganism and a GPD2 gene is down-regulated in the microorganism. In some embodiments, a GPD1 gene is down-regulated in the microorganism and a GPD2 gene is deleted from the microorganism.

In some embodiments, the enzyme in the glycerol-production pathway is a glycerol-3-phosphate phosphatase. In some embodiments, the glycerol-3-phosphate phosphatase is classified as EC number 3.1.3.21.

In some embodiments, the enzyme in the glycerol-production pathway is GPD1, GPD2, glycerol-3-phosphate phosphatase, or a combination thereof.

In some embodiments, a GPD1 gene, a GPD2 gene, and a gene encoding a glycerol-3-phosphate phosphatase are deleted from the microorganism or down-regulated in the microorganism. In some embodiments, a GPD1 gene, a GPD2 gene, and a gene encoding a glycerol-3-phosphate phosphatase are deleted from the microorganism. In some embodiments, a GPD1 gene, a GPD2 gene, and a gene encoding a glycerol-3-phosphate phosphatase are down-regulated in the microorganism. In some embodiments, one of a GPD1 gene, a GPD2 gene, and a gene encoding a glycerol-3-phosphate phosphatase are deleted from the microorganism and the other two of the GPD1 gene, the GPD2 gene, and the gene encoding a glycerol-3-phosphate phosphatase are down-regulated in the microorganism. In some embodiments, one of a GPD1 gene, a GPD2 gene, and a gene encoding a glycerol-3-phosphate phosphatase are down-regulated in the microorganism and the other two of the GPD1 gene, the GPD2 gene, and the gene encoding a glycerol-3-phosphate phosphatase are deleted from the microorganism.

Figure 2A:
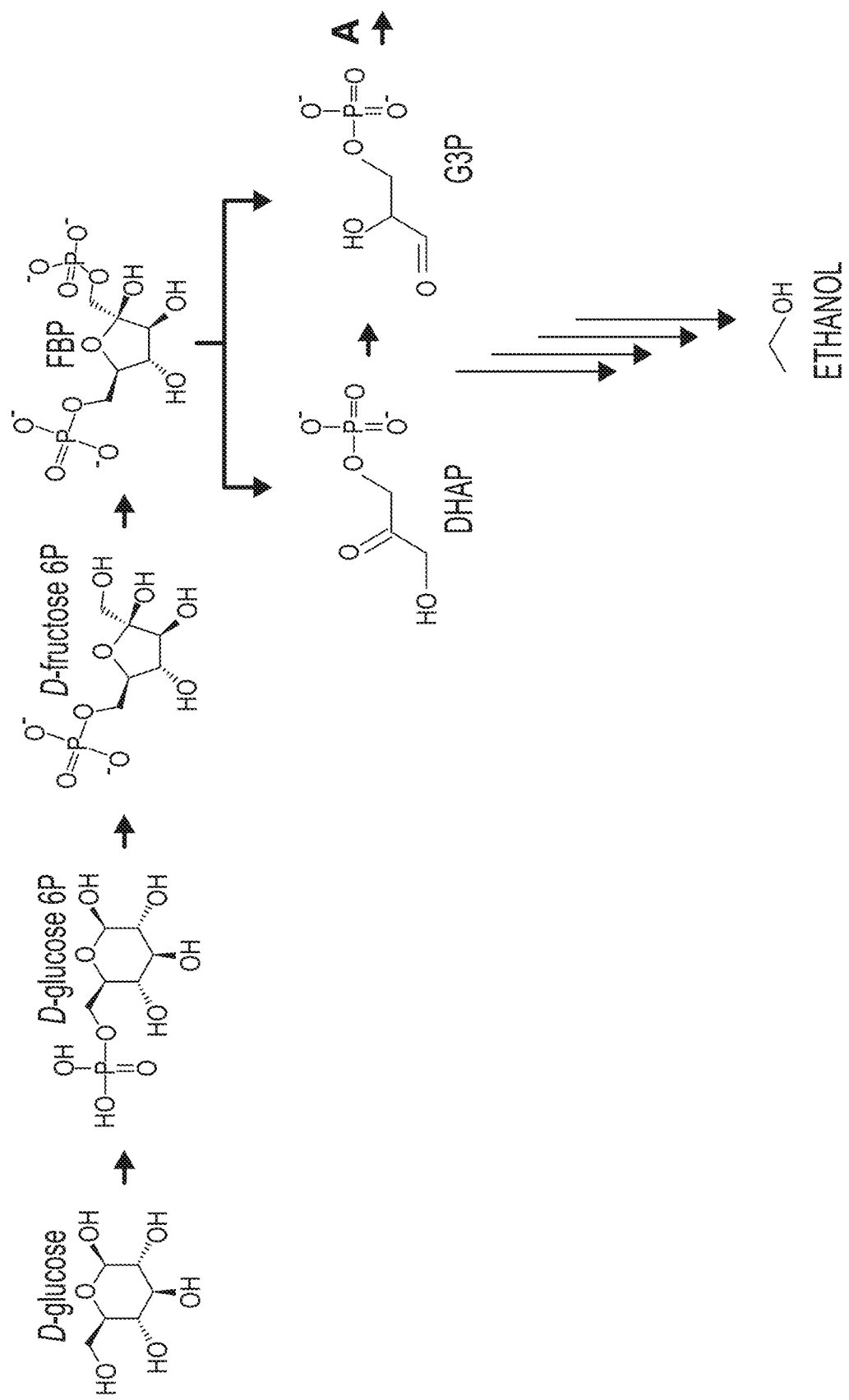
FIG. 2A-2B are schematic overviews of a biosynthetic pathway utilized by recombinant microorganisms of the disclosure for 2,4-FDME and ethanol production.
Figure 2B:
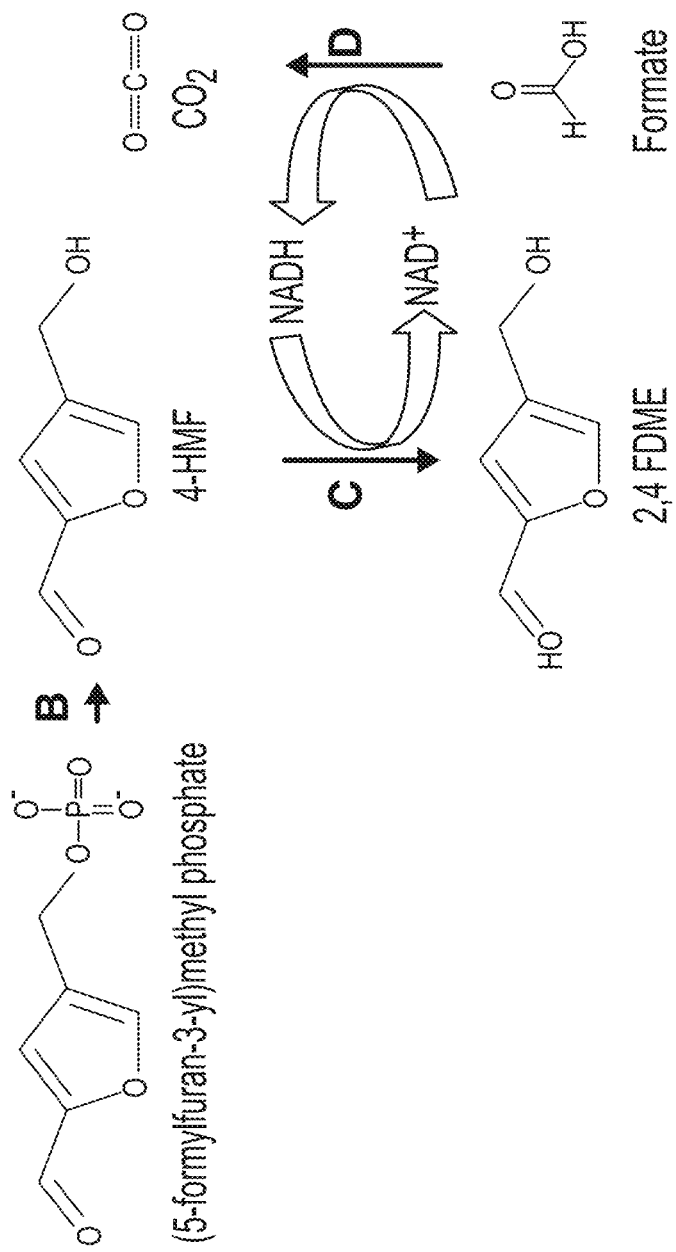

Some embodiments of the present disclosure are shown in FIG. 2, which schematically depicts the anaerobic biosynthetic conversion of a carbon feedstock (e.g., glucose) to 2,4-FDME and ethanol, wherein formate is provided as a co-carbon source in the feedstock.

The present disclosure is also directed to methods of co-producing 2,4-FDME and ethanol. In some embodiments, a method of co-producing 2,4-FDME and ethanol comprises: contacting a recombinant microorganism as described herein with a fermentable carbon source under conditions sufficient to produce 2,4-FDME and ethanol. In some embodiments, the carbon source comprises a hexose, a pentose, glycerol, and/or combinations thereof, and a further carbon source that is a one-carbon compound such as formate. In some embodiments, the conditions are anaerobic conditions. In some embodiments, the methods comprise cultivating the recombinant microorganism in a culture medium containing a feedstock providing a carbon source until 2,4-FDME is produced in the absence of oxygen.

In some embodiments, the methods of co-producing 2,4-FDME and ethanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandimethanol (2,4-FDME); and (d) converting formate to NADH and $CO_2$. In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-FDME with a dehydrogenase. In some embodiments, the methods comprise converting formate to NADH and $CO_2$ with a $NAD^+$-dependent formate dehydrogenase. In some embodiments, the microorganism comprises at least one deletion of an enzyme in a glycerol-production pathway or at least one genetic modification that leads to a down-regulation of an enzyme in a glycerol-production pathway.

The present disclosure includes a method of producing a recombinant microorganism capable of producing 2,4-FDME, the method comprising introducing into and/or overexpressing in the recombinant microorganism the following: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; and (d) at least one endogenous and/or exogenous nucleic acid molecule encoding one or more polypeptides that catalyze the production of NADH and $CO_2$ from formate.

Coupling 2,4-FDME Production with MSA-Based Acetone/2-Propanol Pathway

In some embodiments, the present disclosure comprises recombinant microorganisms and related methods for anaerobically converting one or more carbon sources to 2,4-furandimethanol (2,4-FDME), ethanol, and acetone and/or isopropanol. In some embodiments, the one or more carbon sources are selected from glycerol, a monosaccharide, or a combination thereof.

In some embodiments, the 2,4-FDME pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDME, more efficiently and more cost-effectively than aerobic pathways for 2,4-FDME production. Coupling 2,4-FDME and ethanol production further advantageously enables production of 2,4-FDME with an economically valuable chemical.

In some embodiments, a NADH/NADPH-consuming 2,4-FDME pathway disclosed herein is coupled to a NADH/NADPH-generating pathway to acetone and/or 2-propanol via an MSA intermediate. In some embodiments, coupling of the pathway with an ethanol production pathway (e.g., the canonical ethanol production pathway in yeast) provides ATP surplus.

In some embodiments, the present disclosure comprises recombinant microorganisms and related methods for converting one or more carbon sources to 2,4-FDME and for converting phosphoenol pyruvate to acetone and/or isopropanol via malonate semialdehyde.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDME via several enzymatically-catalyzed successive steps as described herein; (2) at least one endogenous and/or exogenous nucleic acid molecule encoding a polypeptide that catalyzes the production of oxaloacetate from phosphoenol pyruvate (PEP); (3) at least one endogenous and/or exogenous nucleic acid molecule encoding one or more polypeptides that catalyze: (a) the production of malonate semialdehyde from oxaloacetate; and/or (b) the production of aspartate from oxaloacetate, the production of β-alanine from aspartate, and the production of malonate semialdehyde from β-alanine; and/or (c) the production of malonyl-CoA from malonate semialdehyde; and/or (d) the production of malonyl-CoA from oxaloacetate; and/or (4) at least one endogenous and/or exogenous nucleic acid molecule encoding one or more polypeptides that catalyze: (a) the production of acetyl-CoA from malonate semialdehyde, and the production of acetoacetyl-CoA from acetyl-CoA; and/or (b) the production of acetyl-CoA from malonyl-CoA, and the production of acetoacetyl-CoA from acetyl-CoA; and/or (c) the production of acetoacetyl-CoA from malonyl-CoA; and/or (5) at least one endogenous and/or exogenous nucleic acid molecule encoding one or more polypeptides that catalyze: (a) the production of acetoacetate from acetoacetyl-CoA; and/or (b) the production of HMG-CoA from acetoacetyl-CoA, and the production of acetoacetate from HMG-CoA; and (6) at least one endogenous and/or exogenous nucleic acid molecule encoding a polypeptide that catalyzes the production of acetone from acetoacetate.

In some embodiments, the polypeptide that catalyzes the production of oxaloacetate from phosphoenol pyruvate (PEP) is a phosphoenol pyruvate carboxylase (ppc) and/or a phosphoenol pyruvate carboxykinase (pepck). In some aspects, the phosphoenol pyruvate carboxylase and/or phosphoenol pyruvate carboxykinase are selected from a fungi, yeast, bacterium, insect, animal, plant, or flagellate. In some aspects, the phosphoenol pyruvate carboxylase and/or phosphoenol pyruvate carboxykinase are from *E. coli*.

In some embodiments, the polypeptide that catalyzes the production of malonate semialdehyde from oxaloacetate comprise an oxaloacetate decarboxylase that catalyzes the direct decarboxylation of oxaloacetate. In some embodiments, the recombinant microorganism comprises one or more oxaloacetate decarboxylases including, but not limited to, enzymes with EC number 4.1.1.72, EC number 4.1.1.7, or EC number 4.1.1.71. In some embodiments, the oxaloacetate decarboxylase is selected from an α-ketoisovalerate decarboxylase, a benzoylformate decarboxylase, or a 2-oxoglutarate decarboxylase. In some embodiments, the alpha-ketoisovalerate decarboxylase (kdca) is from *Lactococcus lactis*. In some embodiments, the benzoylformate decarboxylase (Mdlc) is from *Pseudomonas putida*. In some embodiments, the 2-oxoglutarate decarboxylase (Oxdc) is from *Oenococcus oeni*. In some embodiments, the 2-oxoglutarate decarboxylase (oxdc) is from *Euglena gracilis*. In some aspects, the oxaloacetate decarboxylase is a genetically modified variant of the foregoing enzymes. Examples of genetically modified enzyme variants that are suitable for catalyzing the direct conversion of oxaloacetate to malonate semialdehyde are described, for example, in U.S. Patent Application Publication No. 2010/0021978, U.S. Pat. No. 8,809,027, International Application Publication No. WO 2018/213349, and U.S. patent application Ser. No. 16/719,833, which are hereby incorporated by reference.

In some embodiments, the polypeptide that catalyzes the production of aspartate from oxaloacetate is an aspartate amino transferase (aat2). In some embodiments, the aspartate amino transferase is from *S. cerevisiae*.

In some embodiments, the polypeptide that catalyzes the production of β-alanine from aspartate is an aspartate decarboxylase (pand). In some embodiments, the aspartate decarboxylase is from *Tribolium castaneum*. In some embodiments, the aspartate decarboxylase is from *Corynebacterium glutamicum*.

In some embodiments, the polypeptide that catalyzes the production of malonate semialdehyde from β-alanine is a β-alanine pyruvate amino transferase (baat) and/or a β-alanine transaminase (pyd4). In some embodiments, the β-alanine pyruvate amino transferase is from *Bacillus cereus*. In some embodiments, the β-alanine transaminase is from *Lachancea kluyveri*.

In some embodiments, the aspartate amino transferase, aspartate decarboxylase, β-alanine pyruvate amino transferase, and/or β-alanine transaminase are selected from a fungi, yeast, bacterium, insect, animal, plant, or flagellate.

In some embodiments, the polypeptide that catalyzes the production of malonyl-CoA from malonate semialdehyde is a malonyl-CoA reductase and/or 2-keto acid decarboxylase. In some embodiments, the malonyl-CoA reductase (mcr) is from *Chloroflexus aurantiacus*. In some embodiments, the 2-keto acid decarboxylase (kivD) is from *Lactococcus lac-*

*tis*. In some embodiments, the 2-keto acid decarboxylase (kdcA) is from *Lactococcus lactis*. In some embodiments, the 2-keto acid decarboxylase (ARO10) is from *Saccharomyces cerevisiae*.

In some embodiments, the polypeptide that catalyzes the production of malonyl-CoA from oxaloacetate is a malonyl-CoA synthetase. In some embodiments, the malonyl-CoA synthetase is classified as EC number 6.2.1.-. In some embodiments, the malonyl-CoA synthetase (matB) is from *Rhizobium trifolii*. In some embodiments, the malonyl-CoA synthetase (AAE13) is from *Arabidopsis thaliana*.

In some embodiments, the polypeptide that catalyzes the production of acetyl-CoA from malonate semialdehyde is a malonate semialdehyde dehydrogenase. In some embodiments, the malonate semialdehyde dehydrogenase is classified as EC number 1.2.1.18 or EC number 1.2.1.27. In some embodiments, the malonate semialdehyde dehydrogenase (bauC) is from *Pseudomonas aeruginosa*. In some embodiments, the malonate semialdehyde dehydrogenase (Ald6) is from *Candida albicans*. In some embodiments, the malonate semialdehyde dehydrogenase (iolA) is from *Lysteria monocytogenes*. In some embodiments, the malonate semialdehyde dehydrogenase (dddC) is from *Halomonas* sp. HTNK1.

In some embodiments, the polypeptide that catalyzes the production of acetoacetyl-CoA from acetyl-CoA is a thiolase and/or an acetyl-CoA acetyltransferase. In some embodiments, the thiolase or an acetyl-CoA acetyltransferase is classified as EC number 2.3.1.16 or EC number 2.3.1.9. In some embodiments, the thiolase is a β-ketothiolase. In some embodiments, the J3-ketothiolase (phaA) is from *Acinetobacter* sp. RA384. In some embodiments, the β-ketothiolase (BktB) is from *Cupriviadus necator*. In some embodiments, the β-ketothiolase (BktC) is from *Cupriviadus necator*. In some embodiments, the β-ketothiolase (BktB) is from *Cupriavidus taiwanensis*. In some embodiments, the β-ketothiolase (POT1) is from *Saccharomyces cerevisiae*. In some embodiments, the acetyl-CoA acetyltransferase (phaA) is from *Cupriavidus necator*. In some embodiments, the acetyl-CoA acetyltransferase (thlA) is from *Clostridium acetobutylicum*. In some embodiments, the acetyl-CoA acetyltransferase (thlB) is from *Clostridium acetobutylicum*. In some embodiments, the acetyl-CoA acetyltransferase (phaA) is from *Zoogloea ramigera*. In some embodiments, the acetyl-CoA acetyltransferase (atoB) is from *Escherichia coli*. In some embodiments, the acetyl-CoA acetyltransferase (ERG10) is from *Saccharomyces cerevisiae*.

In some embodiments, the polypeptide that catalyzes the production of acetyl-CoA from malonyl-CoA is a malonyl-CoA decarboxylase. In some embodiments, the malonyl-CoA decarboxylase is classified as EC number 4.1.1.9. In some embodiments, the malonyl-CoA decarboxylase (MatA) is from *Rhizobium trifolii*. In some embodiments, the malonyl-CoA decarboxylase (MLYCD) is from *Homo sapiens*.

In some embodiments, the polypeptide that catalyzes the production of acetoacetyl-CoA from malonyl-CoA is an acetoacetyl-CoA synthase. In some embodiments, the acetoacetyl-CoA synthase is classified as EC number 2.3.1.194. In some embodiments, the acetoacetyl-CoA synthase is nphT7 from *Streptomyces* sp.

In some embodiments, the polypeptide that catalyzes the production of acetoacetate from acetoacetyl-CoA is an acetoacetyl-CoA thioesterase and/or an acetoacetyl-CoA transferase, and/or acetoacetyl-CoA synthase. In some embodiments, the acetoacetyl-CoA thioesterase and/or acetoacetyl-CoA transferase, and/or acetoacetyl-CoA synthase is classified as EC number 2.8.3.8, EC number 2.8.3.9, EC number 2.3.3.10, EC number 4.1.3.4, or EC number 2.3.1.194. In some embodiments, the acetoacetyl-CoA transferase/synthase is atoA/atoD from *Escherichia coli*. In some embodiments, the acetoacetyl-CoA transferase/synthase is C7401_123119 from *Paraburkholderia unamae*. In some embodiments, the acetoacetyl-CoA transferase/synthase is YdiF from *Escherichia coli*. In some embodiments, the acetoacetyl-CoA transferase/synthase is ctfA/ctfB from *Clostridium acetobutylicum*. In some embodiments, the acetoacetyl-CoA transferase/synthase is ctfA/ctfB from *Clostridium saccharobutylicum*. In some embodiments, the acetoacetyl-CoA transferase/synthase is ctfA/ctfB from *Escherichia coli*.

In some embodiments, the polypeptide that catalyzes the production of HMG-CoA from acetoacetyl-CoA is a hydroxymethylglutaryl-CoA synthase. In some embodiments, the hydroxymethylglutaryl-CoA synthase is classified as EC number 2.3.3.10. In some embodiments the hydroxymethylglutaryl-CoA synthase is ERG13 from *Saccharomyces cerevisiae*. In some embodiments, the polypeptide that catalyzes the production of acetoacetate from HMG-CoA is a hydroxymethylglutaryl-CoA lyase. In some embodiments, the hydroxymethylglutaryl-CoA lyase is classified as EC number 4.1.3.4. In some embodiments the hydroxymethylglutaryl-CoA lyase is yngG from *Bacillus subtilis*.

In some embodiments, the polypeptide that catalyzes the production of acetone from acetoacetate is an acetoacetate decarboxylase. In some embodiments, the acetoacetate decarboxylase is classified as EC number 4.1.1.4. In some embodiments, the acetoacetate decarboxylase (adc) is from *Clostridium acetobutylicum*. In some embodiments, the acetoacetate decarboxylase (adc) is from *Clostridium saccharoperbutylacetonicum*. In some embodiments, the acetoacetate decarboxylase (adc) is from *Clostridium beijerinkii*. In some embodiments, the acetoacetate decarboxylase (adc) is from *Clostridium pasteuranum*. In some embodiments, the acetoacetate decarboxylase (adc) is from *Pseudomonas putida*.

In some embodiments, the recombinant microorganism further comprises at least one endogenous and/or exogenous nucleic acid molecule encoding one or more polypeptides that catalyze the production of isopropanol from acetone. In some embodiments, the polypeptide that catalyzes the production of isopropanol from acetone is an alcohol dehydrogenase. In some aspects, the alcohol dehydrogenase is classified as EC number 1.1.1.2 or EC number 1.2.1.87. In some embodiments, the alcohol dehydrogenase (alrA) is from *Acinetobacter* sp. In some embodiments, the alcohol dehydrogenase (bdhI) is from *Clostridium acetobutylicum*. In some embodiments, the alcohol dehydrogenase (bdhII) is from *Clostridium acetobutylicum*. In some embodiments, the alcohol dehydrogenase (adhA) is from *Clostridium glutamicum*. In some embodiments, the alcohol dehydrogenase (yqhD) is from *Escherichia coli*. In some embodiments, the alcohol dehydrogenase (adhP) is from *Escherichia coli*. In some embodiments, the alcohol dehydrogenase (PduQ) is from *Propionibacterium freudenreichii*. In some embodiments, the alcohol dehydrogenase (ADH1) is from *Saccharomyces cerevisiae*. In some embodiments, the alcohol dehydrogenase (ADH2) is from *Saccharomyces cerevisiae*. In some embodiments, the alcohol dehydrogenase (ADH4) is from *Saccharomyces cerevisiae*. In some embodiments, the alcohol dehydrogenase (ADH6) is from *Saccharomyces cerevisiae*. In some embodiments, the alcohol dehydrogenase (PduQ) is from *Salmonella enterica*. In some embodiments, the alcohol dehydrogenase (Adh) is from *Sulfolobus tokodaii*. In some embodiments, the alcohol dehydrogenase is a 2-propanol dehydrogenase. In some embodiments, the 2-propanol dehydrogenase is PRDH from *Devosia riboplavina*. In some embodiments, the 2-propanol dehydrogenase is PRDH from *Sporotrichum pulverulentum*.

Figure 3:
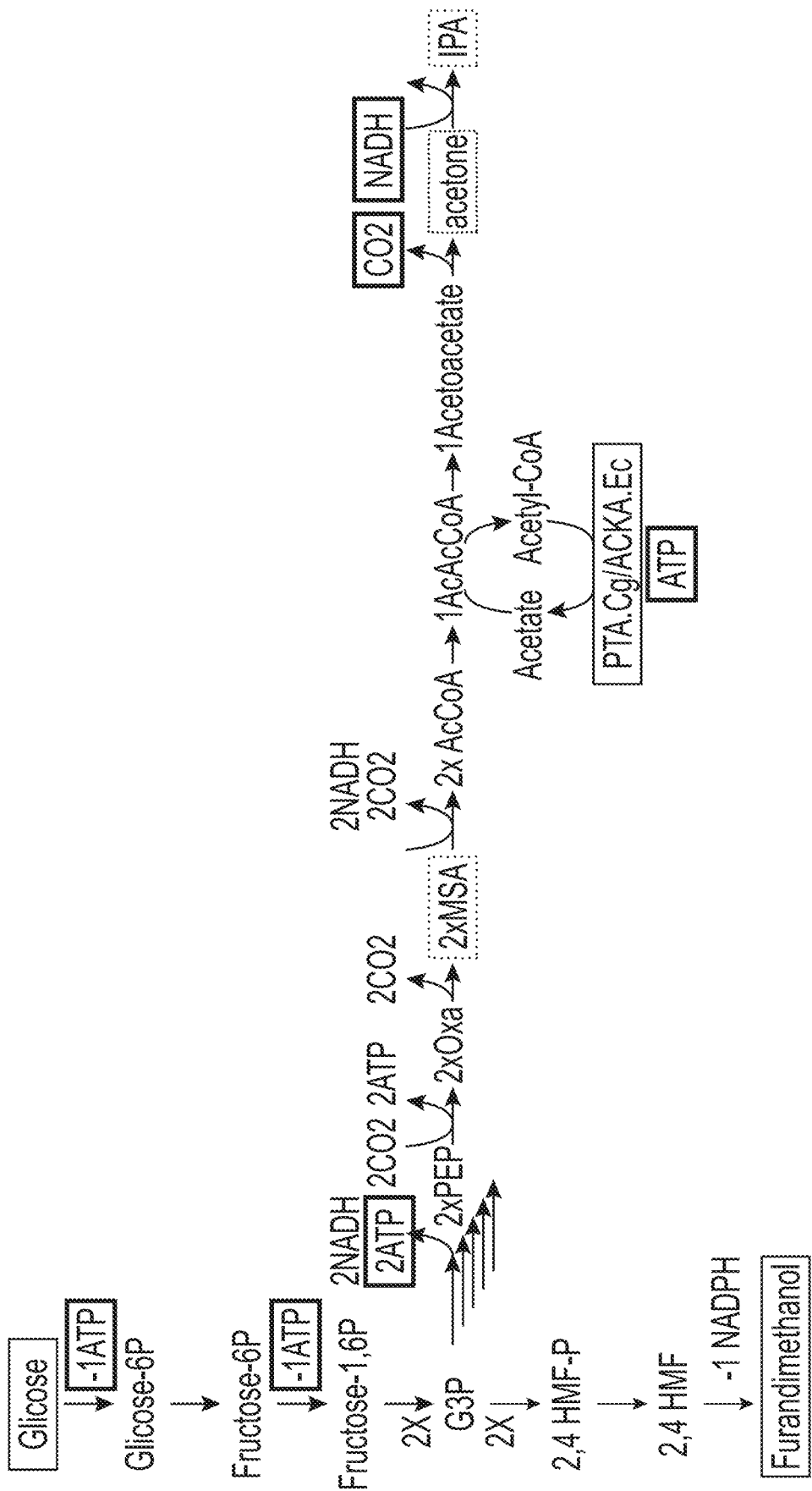
FIG. 3 is a schematic overview of a biosynthetic pathway utilized by recombinant microorganisms of the disclosure for 2,4-FDME, ethanol, and acetone and/or isopropanol production.

Some embodiments of the present disclosure are shown in FIG. 3, which schematically depicts the anaerobic biosynthetic conversion of a carbon feedstock (e.g., glucose) to 2,4-FDME, ethanol, and acetone and/or isopropanol.

The present disclosure is also directed to methods of co-producing 2,4-FDME, ethanol, and acetone and/or isopropanol. In some embodiments, a method of co-producing 2,4-FDME, ethanol, and acetone and/or isopropanol comprises: contacting a recombinant microorganism as described herein with a fermentable carbon source under conditions sufficient to produce 2,4-FDME, ethanol, and acetone and/or isopropanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDME is produced in the absence of oxygen.

In some embodiments, the methods of co-producing 2,4-FDME, ethanol, and acetone and/or isopropanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandimethanol (2,4-FDME); (d) converting PEP to oxaloacetate; (e) converting (i) oxaloacetate to malonate semialdehyde; and/or (ii) oxaloacetate to aspartate, aspartate to β-alanine, and β-alanine to malonate semialdehyde; and/or (iii) malonate semialdehyde to malonyl-CoA; and/or (iv) oxaloacetate to malonyl-CoA; (f) converting (i) malonate semialdehyde to acetyl-CoA, and acetyl-CoA to acetoacetyl-CoA; and/or (ii) malonyl-CoA to acetyl-CoA, and acetyl-CoA to acetoacetyl-CoA; and/or (iii) malonyl-CoA to acetoacetyl-CoA; (g) converting: (i) acetoacetyl-CoA to acetoacetate; and/or (ii) acetoacetyl-CoA to HMG-CoA, and HMG-CoA to acetoacetate; and (h) converting acetoacetate to acetone.

In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-FDME with a dehydrogenase. In some embodiments, the methods comprise converting PEP to oxaloacetate with a phosphoenol pyruvate carboxylase and/or a phosphoenol pyruvate carboxykinase. In some embodiments, the methods comprise converting oxaloacetate to malonate semialdehyde with a oxaloacetate 1-decarboxylase (MSA forming). In some embodiments, the methods comprise converting oxaloacetate to aspartate with an aspartate amino transferase. In some embodiments, the methods comprise converting aspartate to β-alanine with an aspartate decarboxylase. In some embodiments, the methods comprise converting β-alanine to malonate semialdehyde with a β-alanine pyruvate amino transferase and/or a β-alanine transaminase. In some embodiments, the methods comprise converting malonate semialdehyde to malonyl-CoA with a malonyl-CoA reductase and/or 2-keto acid decarboxylase. In some embodiments, the methods comprise converting oxaloacetate to malonyl-CoA with a malonyl-CoA synthetase. In some embodiments, the methods comprise converting malonate semialdehyde to acetyl-CoA with a malonate semialdehyde dehydrogenase. In some embodiments, the methods comprise converting acetyl-CoA to acetoacetyl-CoA with a thiolase and/or an acetyl-CoA acetyltransferase. In some embodiments, the methods comprise converting malonyl-CoA to acetyl-CoA with a malonyl-CoA decarboxylase. In some embodiments, the methods comprise converting malonyl-CoA to acetoacetyl-CoA with an acetoacetyl-CoA synthase. In some embodiments, the methods comprise converting acetoacetyl-CoA to acetoacetate with a an acetoacetyl-CoA thioesterase and/or an acetoacetyl-CoA transferase. In some embodiments, the methods comprise converting acetoacetyl-CoA to HMG-CoA with a hydroxymethylglutaryl-CoA synthase. In some embodiments, the methods comprise converting HMG-CoA to acetoacetate with a hydroxymethylglutaryl-CoA lyase. In some embodiments, the methods comprise converting acetoacetate to acetone with a acetoacetate decarboxylase.

In some embodiments, the methods further comprise converting acetone to isopropanol. In some embodiments, the methods further comprise converting acetone to isopropanol with an alcohol dehydrogenase.

The present disclosure includes a method of producing a recombinant microorganism capable of producing 2,4-FDME, the method comprising introducing into and/or overexpressing in the recombinant microorganism the following: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; (d) at least one endogenous and/or exogenous nucleic acid molecule encoding a polypeptide that catalyzes the production of oxaloacetate from phosphoenol pyruvate (PEP); (e) at least one endogenous and/or exogenous nucleic acid molecule encoding one or more polypeptides that catalyze: (1) the production of malonate semialdehyde from oxaloacetate; and/or (2) the production of aspartate from oxaloacetate, the production of β-alanine from aspartate, and the production of malonate semialdehyde from β-alanine; and/or (3) the production of malonyl-CoA from malonate semialdehyde; and/or (4) the production of malonyl-CoA from oxaloacetate; and/or (f) at least one endogenous and/or exogenous nucleic acid molecule encoding one or more polypeptides that catalyze: (1) the production of acetyl-CoA from malonate semialdehyde, and the production of acetoacetyl-CoA from acetyl-CoA; and/or (2) the production of acetyl-CoA from malonyl-CoA, and the production of acetoacetyl-CoA from acetyl-CoA; and/or (3) the production of acetoacetyl-CoA from malonyl-CoA; and/or (g) at least one endogenous and/or exogenous nucleic acid molecule encoding one or more polypeptides that catalyze: (1) the production of acetoacetate from acetoacetyl-CoA; and/or (2) the production of HMG-CoA from acetoacetyl-CoA, and the production of acetoacetate from HMG-CoA; and (h) at least one endogenous and/or exogenous nucleic acid molecule encoding a polypeptide that catalyzes the production of acetone from acetoacetate. In some embodiment, the method further comprises introducing into and/or overexpressing in the recombinant microorganism at least one endogenous and/or exogenous nucleic acid molecule encoding one or more polypeptides that catalyze the production of isopropanol from acetone.

2,4-FDME Production Coupled With Pentose Phosphate Pathway Overexpression

In some embodiments, the present disclosure comprises recombinant microorganisms and related methods for anaerobically converting one or more carbon sources to 2,4-furandimethanol (2,4-FDME) and ethanol. In some embodiments, the one or more carbon sources are selected from glycerol, a monosaccharide, or a combination thereof.

In some embodiments, the 2,4-FDME pathway disclosed herein is coupled to electron consuming pathways to provide redox balance and with an ethanol production pathway (e.g., the canonical ethanol production pathway in yeast) to provide ATP surplus. In some embodiments, the coupled pathways disclosed herein provide anaerobic production of 2,4-FDME, more efficiently and more cost-effectively than aerobic pathways for 2,4-FDME production. Coupling 2,4-FDME and ethanol production further advantageously enables production of 2,4-FDME with an economically valuable chemical.

In some embodiments, a NADH/NADPH-consuming 2,4-FDME pathway disclosed herein is coupled to the oxidative pentose phosphate pathway and the oxidative pentose phosphate pathway is overexpressed to increase NADPH production. In some embodiments, coupling of the pathway with an ethanol production pathway (e.g., the canonical ethanol production pathway in yeast) provides ATP surplus.

In some embodiments, the recombinant microorganism of any one of the embodiments disclosed herein comprises: (1) at least one endogenous and/or exogenous nucleic acid molecule encoding one or more polypeptides capable of converting a carbon source to 2,4-FDME via several enzymatically-catalyzed successive steps as described herein; (2) at least one endogenous and/or exogenous nucleic acid molecule encoding one or more polypeptides that catalyze the production of 6-phospho-D-gluconate and NADPH from D-glucose-6-phosphate; and (3) at least one endogenous and/or exogenous nucleic acid molecule encoding one or more polypeptides that catalyze the production of D-ribulose-5-phosphate, $CO_2$, and NADPH from 6-phospho-D-gluconate.

In some embodiments, the polypeptides that catalyze the production of 6-phospho-D-gluconate and NADPH from D-glucose-6-phosphate are a glucose-6-phosphate dehydrogenase and a gluconolactonase. In some embodiments, the glucose-6-phosphate dehydrogenase (G6PD) is classified as EC number 1.1.1.49.

In some embodiments, the polypeptide that catalyzes the production of D-ribulose-5-phosphate, $CO_2$, and NADPH from 6-phospho-D-gluconate is a 6-phosphogluconate dehydrogenase. In some embodiments, the 6-phosphogluconate dehydrogenase is classified as EC number 1.1.1.44. In some embodiments, increased flux toward the oxidative pentose phosphate pathway instead of glycolysis increases the [NADPH]/[NADP$^+$] ratio.

In some embodiments, the recombinant microorganism, further comprises at least one endogenous and/or exogenous nucleic acid molecule encoding one or more polypeptides that catalyze NADPH-driven reduction of NAD(+). In some embodiments, the polypeptide that catalyzes the NADPH-driven reduction of NAD(+) is a NAD(P)+ transhydrogenase. In some embodiments, the NAD(P)+ transhydrogenase is classified as EC number EC 1.6.1. In some embodiments, the transhydrogenase is selected from NAD(P)+ transhydrogenases (Si-specific) classified as EC number 1.6.1.1, NAD(P)+ transhydrogenases (Re/Si-specific) classified as EC number 1.6.1.2, NAD(P)+ transhydrogenases classified as EC number 1.6.1.3 and/or NAD(P)+ transhydrogenases (ferredoxin) classified as EC number 1.6.1.4.

In some embodiments, the recombinant microorganism, further comprises at least one deletion of an enzyme in a pathway for converting fructose-6-phosphate and ATP to fructose-1,6-biphosphate, or at least one genetic modification that leads to a down-regulation of an enzyme in a pathway for converting fructose-6-phosphate and ATP to fructose-1,6-biphosphate. In some embodiments, the enzyme in the pathway for converting fructose-6-phosphate and ATP to fructose-1,6-biphosphate is a phosphofructokinase.

In some embodiments, overexpression of glucose-6-phosphate dehydrogenase (e.g., ZWF1) and mutation of phosphofructokinase (e.g., isozymes PFK1 and PFK2) synergistically increases the [NADPH]/[NADP$^+$] ratio.

The present disclosure is also directed to methods of co-producing 2,4-FDME and ethanol. In some embodiments, a method of co-producing 2,4-FDME and ethanol comprises: contacting a recombinant microorganism as described herein with a fermentable carbon source under conditions sufficient to produce 2,4-FDME and ethanol. In some embodiments, the carbon source comprises a hexose, a pentose, glycerol, and/or combinations thereof. In some embodiments, the conditions are anaerobic conditions. In some embodiments, the methods comprise cultivating the recombinant microorganism in a culture medium containing a feedstock providing a carbon source until 2,4-FDME is produced in the absence of oxygen.

In some embodiments, the methods of co-producing 2,4-FDME and ethanol in a recombinant microorganism comprise: (a) converting glyceraldehyde 3-phosphate (G3P) to 4-hydroxymethylfurfural phosphate; (b) converting 4-hydroxymethylfurfural phosphate to 4-hydroxymethylfurfural (4-HMF); (c) converting 4-HMF to 2,4-furandimethanol (2,4-FDME); (d) converting D-glucose-6-phosphate to 6-phospho-D-gluconate and NADPH; and (e) converting 6-phospho-D-gluconate to D-ribulose-5-phosphate, $CO_2$, and NADPH. In some embodiments, the methods comprise converting glyceraldehyde 3-phosphate (G3P) to 4-hydroxymethylfurfural phosphate with a methyl phosphate synthase. In some embodiments, the methods comprise converting 4-hydroxymethylfurfural phosphate to 4-hydroxymethylfurfural (4-HMF) with a phosphatase or a kinase. In some embodiments, the methods comprise converting 4-HMF to 2,4-FDME with a dehydrogenase. In some embodiments, the methods comprise converting D-glucose-6-phosphate to 6-phospho-D-gluconate and NADPH with a glucose-6-phosphate dehydrogenase and a gluconolactonase. In some embodiments, the methods comprise converting 6-phospho-D-gluconate to D-ribulose-5-phosphate, $CO_2$, and NADPH with a 6-phosphogluconate dehydrogenase. In some embodiments, the recombinant microorganism, further comprises at least one deletion of an enzyme in a pathway for converting fructose-6-phosphate and ATP to fructose-1,6-biphosphate, or at least one genetic modification that leads to a down-regulation of an enzyme in a pathway for converting fructose-6-phosphate and ATP to fructose-1,6-biphosphate.

The present disclosure includes a method of producing a recombinant microorganism capable of producing 2,4-FDME, the method comprising introducing into and/or overexpressing in the recombinant microorganism the following: (a) at least one endogenous and/or exogenous nucleic acid molecule encoding a polypeptide that catalyzes the production of 4-hydroxymethylfurfural phosphate from glyceraldehyde 3-phosphate (G3P); (b) at least one endogenous and/or exogenous nucleic acid molecule encoding a polypeptide that catalyzes the production of 4-hydroxymethylfurfural (4-HMF) from 4-hydroxymethylfurfural phosphate; (c) at least one endogenous and/or exogenous nucleic acid molecule encoding one or more polypeptides that catalyze the production of 2,4-furandimethanol (2,4-FDME) from 4-HMF; (d) at least one endogenous and/or exogenous nucleic acid molecule encoding one or more polypeptides that catalyze the production of 6-phospho-D-gluconate and NADPH from D-glucose-6-phosphate; and (e) at least one endogenous and/or exogenous nucleic acid molecule encoding one or more polypeptides that catalyze the production of D-ribulose-5-phosphate, $CO_2$, and NADPH from 6-phospho-D-gluconate.

Culturing and Feedstock

Culturing of the microorganisms used in the methods of the disclosure may be conducted using any number of processes known in the art for culturing and fermenting substrates using the microorganisms of the present disclosure.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioreactor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. In some aspects, the bioreactor comprises a first, growth reactor in which the microorganisms are cultured, and a second, fermentation reactor, to which fermentation broth from the growth reactor is fed and in which most of the fermentation product is produced. In some aspects, the bioreactor simultaneously accomplishes the culturing of microorganism and the producing the fermentation product from carbon sources such substrates and/or feedstocks provided.

During fermentation, anaerobic conditions can be maintained by, for example, sparging nitrogen through the culture medium. A suitable temperature for fermentation (e.g., about 30° C.) can be maintained using any method known in the art. A near physiological pH (e.g., about 6.5) can be maintained by, for example, automatic addition of sodium hydroxide. The bioreactor can be agitated at, for example, about 50 rpm until fermentation has run to completion.

In some embodiments, the methods of the present disclosure further comprise recovering, collecting, and/or isolating 2,4-FDME and/or a 2,4-FDCA monomer. The recovery/collection/isolation can be by methods known in the art, such as distillation, solid-liquid separation, crystalization, precipitation, membrane-based separation, gas stripping, solvent extraction, and expanded bed adsorption.

In some embodiments, the feedstock comprises a carbon source. In some embodiments, the carbon source may be selected from sugars, glycerol, alcohols, organic acids, alkanes, fatty acids, lignocellulose, proteins, carbon dioxide, and carbon monoxide. In some embodiments, the carbon source is a sugar. In some embodiments, the sugar is a monosaccharide. In some embodiments, the sugar is a polysaccharide. In some embodiments, the sugar is glucose or oligomers of glucose thereof. In some embodiments, the oligomers of glucose are selected from fructose, sucrose, starch, cellobiose, maltose, lactose and cellulose. In some embodiments, the sugar is a five carbon sugar. In some embodiments, the sugar is a six carbon sugar. In some embodiments, the feedstock comprises one or more five carbon sugars and/or one or more six carbon sugars. In some embodiments, the feedstock comprises one or more of xylose, glucose, arabinose, galactose, maltose, fructose, mannose, sucrose, and/or combinations thereof. In some embodiments, the feedstock comprises one or more of xylose and/or glucose. In some embodiments, the feedstock comprises one or more of arabinose, galactose, maltose, fructose, mannose, sucrose, and/or combinations thereof.

In some embodiments, the microbes utilize one or more five carbon sugars (pentoses) and/or one or more six carbon sugars (hexoses). In some embodiments, the microbes utilize one or more of xylose and/or glucose. In some embodiments, the microbes utilize one or more of arabinose, galactose, maltose, fructose, mannose, sucrose, and/or combinations thereof. In some embodiments, the microbes utilize one or more of xylose, glucose, arabinose, galactose, maltose, fructose, mannose, sucrose, and/or combinations thereof.

In some embodiments, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some embodiments, pentoses may be selected from D-xylose, D-ribose, D-arabinose, D-lyxose, D-xylulose, D-ribulose, and other pentoses known in the art. In some embodiments, the hexoses and pentoses may be selected from the levorotary or dextrorotary enantiomer of any of the hexoses and pentoses disclosed herein.

In some embodiments, the feedstock comprises any of the carbon sources disclosed herein and further comprises a one-carbon compound such as formate.

2,4-FDCA Production

The present disclosure provides a method of producing 2,4-furandicarboxylic acid (2,4-FDCA). In some embodiments, the method comprises: (i) contacting the recombinant ethanol-producing yeast as disclosed herein with a fermentable carbon source under conditions sufficient to produce 2,4-FDME and ethanol; and (ii) converting the 2,4-FDME to 2,4-FDCA.

Additionally, the present disclosure provides a method of enzymatically converting 2,4-FDME to 2,4-FDCA. In some embodiments, the methods comprise contacting 2,4-FDME with one or more enzymes under conditions sufficient to convert 2,4-FDME to 2,4-FDCA.

In some embodiments, the 2,4-FDME is produced by the recombinant microorganisms as disclosed herein. In some embodiments, the 2,4-FDME is produced according to the fermentative methods disclosed herein. In some embodiments, the 2,4-FDME has not been substantially purified from the fermentation process, and/or co-products and/or solids have not been removed from the fermentation process.

In some embodiments, 2,4-FDME is converted to 2,4-FDCA using enzymatic oxidation under conditions sufficient to convert 2,4-FDME to 2,4-FDCA. In some embodiments, the method comprises enzymatically converting 2,4-FDME to 2,4-FDCA with one or more oxidases, one or more laccases, one or more lipases, and/or one or more dehydrogenases, including combinations of oxidases, laccases, lipases, and/or dehydrogenases, either directly or through production of one or more intermediates. In some embodiments, the intermediates are selected from 5-(hydroxymethyl)-3-furaldehyde, 4-(hydroxymethyl)furfural, 5-(hydroxymethyl)furan-3-carboxylic acid, 2,4-furandicarbaldehyde, 4-(hydroxymethyl)-2-furancarboxylic acid, 5-formyl-3-furoic acid, or 4-formyl-2-furoic acid.

Figure 4:
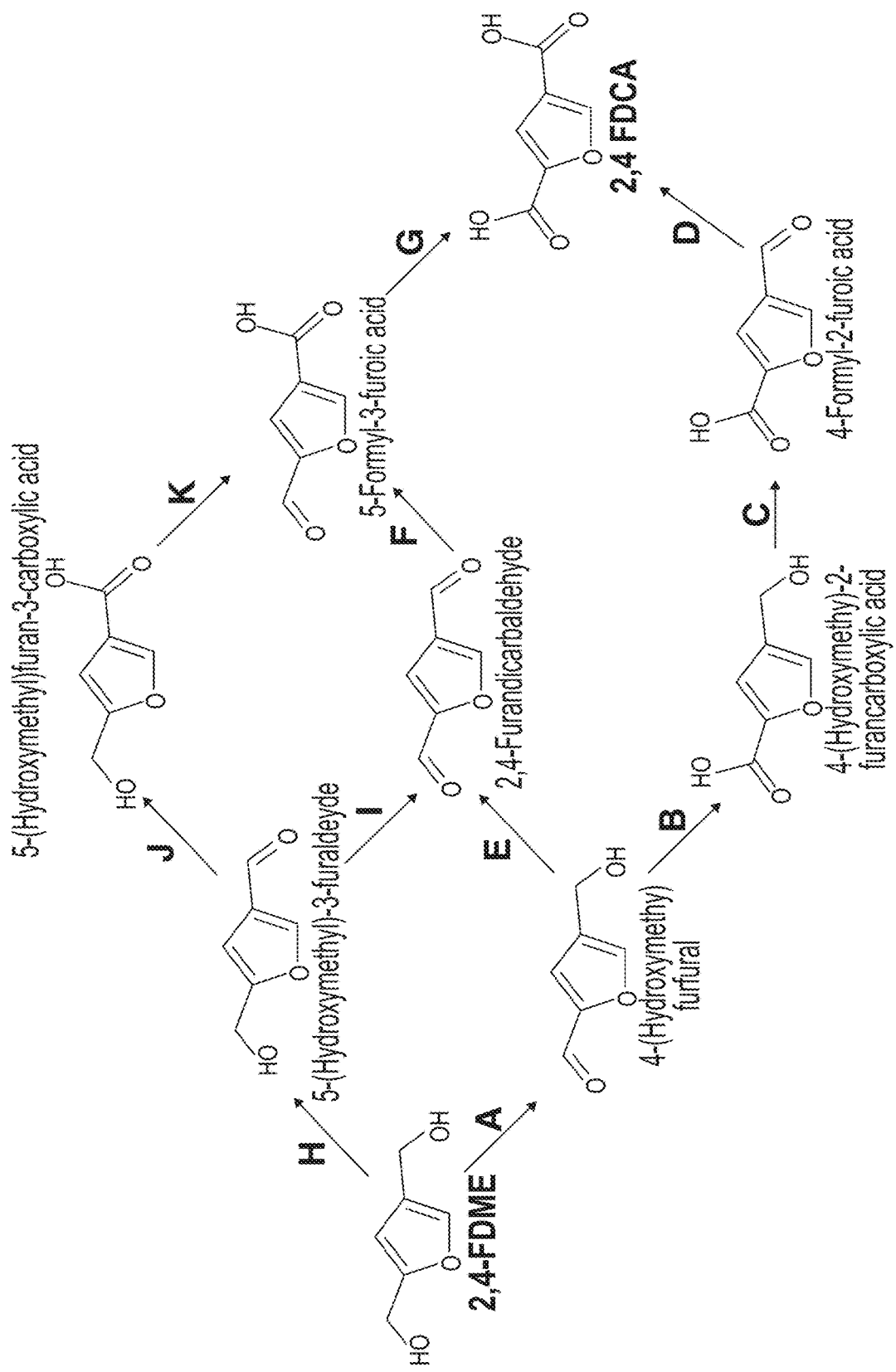
FIG. 4 is a schematic overview of intermediates in the enzymatic oxidation of 2,4-FDME to 2,4-FDCA.

Some embodiments of the present disclosure are shown in FIG. 4, which schematically depicts the intermediates in the oxidation of 2,4-FDME to 2,4-FDCA. In some embodiments, 2,4-FDME is converted to 5-(hydroxymethyl)-3-furaldehyde and/or 4-(hydroxymethyl)furfural. In some embodiments, 5-(hydroxymethyl)-3-furaldehyde is converted to 5-(hydroxymethyl)furan-3-carboxylic acid and/or 2,4-furandicarbaldehyde. In some embodiments, 4-(hydroxymethyl)furfural is converted to 2,4-furandicarbaldehyde and/or 4-(hydroxymethyl)-2-furancarboxylic acid. In some embodiments, 5-(hydroxymethyl)furan-3-carboxylic acid is converted to 5-formyl-3-furoic acid. In some embodiments, 2,4-furandicarbaldehyde is converted to 5-formyl-3-furoic acid. In some embodiments, 4-(hydroxymethyl)-2-furancarboxylic acid is converted to 4-formyl-2-furoic acid. In some embodiments, 5-formyl-3-furoic acid is converted to 2,4-FDCA. In some embodiments, 4-formyl-2-furoic acid is converted to 2,4-FDCA.

In some embodiments, the method comprises contacting 2,4-FDME with only one oxidase, laccase, lipase, or dehydrogenase. In some embodiments, the method comprises contacting 2,4-FDME with more than one oxidase, and/or more than one laccase, and/or more than one lipase, and/or more than one dehydrogenase, and/or a combination of one or more oxidases, laccases, lipases, and/or dehydrogenases.

In some embodiments, the oxidase is an oxidoreductase classified as EC number 1.1.3.-. In some embodiments, the oxidase is classified as EC number 1.1.3.15, EC number 1.1.3.47, EC number 1.1.3.7, EC number 1.1.3.9, and/or EC number 1.1.3.22 (i.e., EC number 1.17.3.2). In some embodiments, the oxidase is a flavoprotein oxidase. In some embodiments, the oxidase is HMF oxidase (HMFO) from *Methylovorus* sp. In some embodiments, the oxidase is a monofunctional alcohol oxidase. In some embodiments, the oxidase is an aryl-alcohol oxidase (EC number 1.1.3.7) comprising an amino acid sequence as set forth in SEQ ID NO: 8, 9, 10, or 11. In some embodiments, the oxidase is a monofunctional aldehyde oxidase. In some embodiments, the oxidase is a bifunctional alcohol/aldehyde oxidase. In some embodiments an aldehyde intermediate is converted into its hydrated form (gem-diol form) and then oxidized by the enzyme.

In some embodiments, the oxidase is a GMC (glucose-methanol-choline) oxidoreductase. In some embodiments, the oxidase is a copper-containing oxidase. In some embodiments, the oxidase is a galactose oxidase (EC number 1.1.3.9) comprising an amino acid sequence as set forth in SEQ ID NO: 13 or a glyoxal oxidase (EC number 1.1.3.15) comprising an amino acid sequence as set forth in SEQ ID NO: 12.

In some embodiments, the laccase is classified as EC number 1.10.3.-.

In some embodiments, the lipase is classified as EC number 3.1.1.-.

In some embodiments, the dehydrogenase is classified as EC number 1.1.1.-. In some embodiments, the dehydrogenase is classified as EC number 1.1.1.1.

In some embodiments, the oxidase is 5-hydroxymethylfurfural oxidase.

In some embodiments, the oxidase is a 4-HMF oxidase.

In some embodiments, the HMF oxidase can be derived from an enzyme listed in Table 1. In some embodiments, the HMF oxidase is homologous or similar to the enzymes listed in Table 1. In some embodiments the 4-HMF oxidase enzyme has an amino acid sequence listed in Table 1. In some embodiments, the HMF oxidase enzyme is evolved or engineered to improve its catalytic efficiency (see, e.g., Martin et al. Biotechnology for Biofuels. (2018) 11, Article number: 56).

In some embodiments, the 4-HMF oxidase is selected from HmfH6 and HmfH7. In some embodiments, the 4-HMF oxidase comprises an amino acid sequence comprising SEQ ID NO: 6 or SEQ ID NO: 7.

In one embodiment, the oxidase is classified as EC number 1.1.3. In one embodiment, the oxidase EC number 1.1.3 is 5-(hydroxymethylfurfural oxidase (EC number 1.1.3.47). In some embodiments, the HMF oxidase can be derived from the gene hmfH. In some embodiments, the HMF oxidase can be derived from *Methylovorus* sp. MP688 or *Cupriavidus basilensis* (see, e.g., Dijkman and Fraaije (2014) Applied Environmental Microbiology, 80.3:1082-1090 and Koopman et al. (2010) PNAS, 107(11):4919-4924). In one embodiment, the HMF oxidase EC number 1.1.3 is an aryl-alcohol oxidase (EC number 1.1.3.7) (see, e.g., Carro et al., FEBS Journal (2014) 282:3218-3229). In one embodiment, the peroxygenase is classified as EC number 1.11.2. In one embodiment, the peroxygenase EC number 1.11.2 is unspecific peroxygenase (EC number 1.11.2.1) (see, e.g., Carro et al., FEBS Journal (2014) 282:3218-3229).

TABLE 1

4-HMF oxidases enzymes

| Name | Organism | Sequence |
| --- | --- | --- |
| HmfH1 | *Methylovorus* sp | MTDTIFDYVIVGGGTAGSVLANRLSARPENRVLLIEAGIDT PENNIPPEIHDGLRPWLPRLSGDKFFWPNLTIHRAAEHPGIT REPQFYEQGRLLGGGSSVNMVVSNRGLPRDYDEWQALGA DGWDWQGVLPYFIKTERDADYGDDPLHGNAGPIPIGRVDS RHWSDFTVAATQALEAAGLPNIHDQNARFDDGYFPPAFTL KGEERFSAARGYLDASVRVRPNLSLWTESRVLKLLTTGNA ITGVSVLRGRETLQVQAREVILTAGALQSPAILLRTGIGPAA DLHALGIPVLADRPGVGRNLWEHSSIGVVAPLTEQARADA STGKAGSRHQLGIRASSGVDPATPSDLFLHIGADPVSGLAS AVFWVNKPSSTGWLKLKDADPFSYPDVDFNLLSDPRDLGR LKAGLRLITHYFAAPSLAKYGLALALSRFAAPQPGGPLLND LLQDEAALERYLRTNVGGVWHASGTARIGRADDSQAVVD KAGRVYGVTGLRVADASIMPTVPTANTNLPTLMLAEKIAD AILTQA (SEQ ID NO: 1) |
| HmfH2 | *Cupriavidus basilensis* | MDTPRERFDYVIVGGGSAGCVLANRLSQDPAIRVALIEAG VDTPPDAVPAEILDSYPMPLFFGDRYIWPSLQARAVAGGRS KVYEQGRVMGGGSSINVQAANRGLPRDYDEWAASGASG WSWQDVLPYFRHLERDVDYGNSPLHGSHGPVPIRRILPQA |

TABLE 1-continued

4-HMF oxidases enzymes

| Name | Organism | Sequence |
|------|----------|----------|
| | | WPPFCTEFAHAMGRSGLSALADQNAEFGDGWFPAAFSNL<br>DDKRVSTAIAYLDADTRRRANLRIYAETTVRKLVVSGREA<br>RGVIAMRADGSRLALDAGEVIVSAGALQSPAILMRAGIGD<br>AGALQALGIEVVADRPGVGRNLQDHPALTFCQFLAPQYR<br>MPLSRRRASMTAARFSSGVPGGEASDMYLSSSTRAGWHA<br>LGNRLGLFFLWCNRPFSRGQVSLAGAQPDVPPMVELNLLD<br>DERDLRRMVAGVRKLVQIVGASALHQHPGDFFPATFSPRV<br>KALSRVSRGNVLLTELLGAVLDVSGPLRRSLIARFVTGGAN<br>LASLLTDESALEGFVRQSVFGVWHASGTCRMGAHADRSA<br>VTDAAGRVHDVGRLRVIDASLMPRLPTANTNIPTIMLAEKI<br>ADTMQAERRAVRPASSEVAHPS (SEQ ID NO: 2) |
| HmfH3 | *Cupriavidus necator* | MDTPRERFDYVIVGGGSAGCVLANRLSQDPAIRVALIEGG<br>VDTPPDAVPVEILDSYPMPLFFGDRYIWPSLQARAVAGGRS<br>KVYEQGRVMGGGSSINVQAANRGLPRDYDEWAASGAPG<br>WSWQDVLPYFRNLERDVDYGNSPLHGSHGPVPIRRILPQA<br>WPPFCTEFAHAMGLSGLSALADQNAEFGDGWFPAAFSNL<br>DDKRVSTAIAYLDADTRRRANLRIYAETTVRKLVVSGREA<br>RGVIAIRADGSRLALDAGEVIVSAGALQSPAILMRAGIGDA<br>GALQALGIEVVADRPGVGRNLQDHPALTFCQFLAPQYRMP<br>LSRRRASMTAARFSSGVPGGEASDMYLSSSTRAGWHALG<br>NRLGLFFLWCNRPFSRGQVSLAGAQPDVPPMVELNLLDDE<br>RDLRRMVAGVRKLVQIVGASALHQHPGDFFPATFSPRVKA<br>LSRLSRGNALLTELLGALLDVSGPLRRSLIARFVTGGANLA<br>SLLVEESALEGFVRQSVFGVWHASGTCRMGAHADRSAVT<br>DAAGRVHDVGRLRVVDASLMPRLPTANTNIPTIMLAEKIA<br>DTMQAERRAVRLASSEVAHQS (SEQ ID NO: 3) |
| HmfH4 | *Cupriavidus pinatubonensis* | MGTPRDRFDYVIVGGGSAGCVLANRLSRDPGIRVALIEGG<br>VDTPPGAVPAEILDSYPMPLFFGDRYLWPSLQARAVAGGR<br>ARLYEQGRVMGGGSSINVQAANRGLPRDYDEWAASGAPG<br>WSWQEVLPYFRKLERDVDFASSPMHGSDGPVPIRRILPPA<br>WPPFCTAFAQAMGRSGLSALDDQNAEFGDGWFPAAFSNL<br>DGKRVSTAIAYLDANTRKRTNLRIFAETTVKELVVSGREA<br>RGVIAVRADGARLALEAAEVIVSAGALQSPAILMRAGIGD<br>AAALQALGIEVVADRPGVGRNLQDHPALTFCQFLAPEYRM<br>PLARRRSSMTAARFSSEVPGGEASDMYLSSSTRAGWHALG<br>NRLGLFFLWCNRPFSRGQVSLAGAQPEVSPLVELNLLDDE<br>RDLRRMVAGVRRLVRIVGASALHQHPDDFFPAIFSPRVKA<br>MSRVSPGNALLTALLGALLDVSGPLRRSLIARFVTGGANL<br>ASLLADESALEGFVRQSVFGVWHASGTCRMGAHADRSAV<br>TDTTGRVHDVGRLRVVDASLMPRLPTANTNIPTIMLAEKIA<br>DAMLAERRATRRALSEVADPG (SEQ ID NO: 4) |
| HmfH5 | *Pandoraea* sp. B-6 | MPRGHAHRRIRRHSVQNVRERFDYVIIGGGSAGCVLAHRL<br>SANRELRVALIEAGSDTPPGAIPAEILDSYPMPVFCGDRYIW<br>PELKAKATAASPLKVYEQGKVMGGGSINVQAANRGLPR<br>DYDDWAEQGASGWAWKDVLPYFRKLERDADYGGSALH<br>GADGPVAIRRIKPDAWPRFCHAFAEGLQRNGLPMLEDQNA<br>EFGDGMFPAAFSNLDDKRVSTAVAYLDAATRARTNLRIYS<br>NTTVERLIVTGQRAHGVVAMSAGGERLQIDAAEVIVSAGA<br>LQSPALLLRAGIGAGSELQALGIPVVADRPGVGRNLQDHPS<br>LTFCHFLDPEFRMPLSRRRASMTAARFSSGLDGCDNADMY<br>LSSATRAAWHALGNRLGLFFLWCNRPFSRGRVQLTSADPF<br>TPPRVDLNLLDDERDARRMAIGVRRVAQIVQQTALHRHPD<br>DFFPAAFSPRVKALSRFSAGNAALTKVLGLALDTPAPLRR<br>WIIDTFVTGGIRMSALLADDKELDAFIRKYVFGVWHASGT<br>CRMGPASDRMAVTNQEGLVHDVANLRVVDASLMPKLPS<br>ANTNIPTIMMAEKIADAILARRKAPPGVLVSSEA (SEQ ID NO: 5) |
| HmfH6 | *Methylovorus* sp | MTDTIFDYVIVGGGTAGSVLANRLSARPENRVLLIEAGIDT<br>PENNIPPEIHDGLRPWLPRLSGDKFFWPNLTIHRAAEHPGIT<br>REPQFYEQGRLLGGGSSVNMVVSNRGLPRDYDEWQALGA<br>DGWDWQGVLPYFIKTERDADYGDDPLHGNAGPIPIGRVDS<br>RHWSDFTVAATQALEAAGLPNIHDQNARFDDGYFPPAFTL<br>KGEERFSAARGYLDASVRVRPNLSLWTESRVLKLLTTGNA<br>ITGVSVLRGRETLQVQAREVILTAGALQSPAILLRTGIGPAA<br>DLHALGIPVLADRPGVGRNLWEHSSIGVVAPLTEQARADA<br>STGKAGSRHQLGIRASSGVDPATPSDLFLHIGADPVSGLAS<br>ARFWVNKPSSTGWLKLKDADPFSYPDVDFNLLSDPRDLGR<br>LKAGLRLITHYFAAPSLAKYGLALALSRFAAPQPGGPLLND<br>LLQDEAALERYLRTNVGGVFPHASGTARIGRADDSQAVVD<br>KAGRVYGVTGLRVADASIMPTVPTANTNLPTLMLAEKIAD<br>AILTQA (SEQ ID NO: 6) |

TABLE 1-continued

4-HMF oxidases enzymes

| Name | Organism | Sequence |
|---|---|---|
| HmfH7 | *Methylovorus* sp MUT | MTDTIFDYVIVGGGTAGSVLANRLSARPENRVLLIEAGIDT PENNIPPEIHDGLRPWLPRLSGDKFFWPNLTVYRAAEHPGI TREPQFYEQGRLLGGGSSVNMVVSNRGLPRDYDEWQALG ADGWDWQGVLPYFIKTERDADYGDDPLHGNAGPIPIGRV DSRHWSDFTVAATQALEAAGLPNIHDQNARFDDGYFPPAF TLKGEERFSAARGYLDASVRVRPNLSLWTESRVLKLL'TTG NAITGVSVLRGRETLQVQAREVILTAGALQSPAILLRTGIGP AADLHALGIPVLADRPGVGRNLWEHSSIGVVAPLTEQARA DASTGKAGSRHQLGIRASSGVDPATPSDLFLHIHADPVSGL ASARFWVNKPSSTGWLKLKDADPFSYPDVDFNLLSDPRDL GRLKAGLRLIKHYFAYPSLAKYGLALALSRFEAPQPGGPLL NDLLQDEAALERYLRTNVGGVFHASGTARIGRADDSQAV VDKAGRVYGVTGLRVADASIMPTVPTANTNLPTMLAEKI ADAILTQA (SEQ ID NO: 7) |
| PeAAo | *Pleurotus eryngii* | MSFGALRQLLLIACLALPSLAATNLPTADFDYVVVGAGNA GNVVAARLTEDPDVSVLVLEAGVSDENVLGAEAPLLAPGL VPNSIFDWNYTTTAQAGYNGRSIAYPRGRMLGGSSSVHYM VMMRGSTEDFDRYAAVTGDEGWNWDNIQQFVRKNEMV VPPADNHNTSGEFIPAVHGTNGSVSISLPGFPTPLDDRVLAT TQEQSEEFFFNPDMGTGHPLGISWSIASVGNGQRSSSSTAY LRPAQSRPNLSVLINAQVTKLVNSGTTNGLPAFRCVEYAEQ EGAPTT'TVCAKKEVVLSAGSVGTPILLQLSGIGDENDLSSV GIDTIVNNPSVGRNLSDHLLLPAAFFVNSNQTFDNIFRDSSE FNVDLDQWTNTRTGPLTALIANHLAWLRLPSNSSIFQTFPD PAAGPNSAHWETIFSNQWFHPAIPRPDTGSFMSVTNALISP VARGDIKLATSNPFDKPLINPQYLSTEFDIFTMIQAVKSNLR FLSGQAWADFVIRPFDPRLRDPTDDAAIESYIRDNANTIFHP VGTASMSPRGASWGVVDPDLKVKGVDGLRIVDGSILPFAP NAHTQGPIYLVGKQGADLIKADQ (SEQ ID NO: 8) |
| PeAAOMUT 1 | *Pleurotus eryngii* MUT1 | MSFGALRQLLLIACLALPSLAATNLPTADFDYVVVGAGNA GNVVAARLTEDPDVSVLVLEAGVSDENVLGAEAPLLAPGL VPNSIFDWNYTTTAQAGYNGRSIAYPRGRMLGGSSSVHYM VMMRGSTEDFDRYAAVTGDEGWNWDNIQQFVRKNEMV VPPADNHNTSGEFIPAVHGTNGSVSISLPGFPTPLDDRVLAT TQEQSEEFFFNPDMGTGHPLGISWSIASVGNGQRSSSSTAY LRPAQSRPNLSVLINAQVTKLVNSGTTNGLPAFRCVEYAEQ EGAPTTTVCAKKEVVLSAGSVGTPILLQLSGIGDENDLSSV GIDTIVNNPSVGRNLSDHLLLPAAFFVNSNQTFDNIFRDSSE FNVDLDQWTNTRTGPLTALIANHLAWLRLPSNSSIFQTFPD PAAGPNSAHWETIFSNQWYHPAIPRPDTGSFMSVTNALISP VARGDIKLATSNPFDKPLINPQYLSTEFDIFTMIQAVKSNLR FLSGQAWADFVIRPFDPRLRDPTDDAAIESYIRDNANTIFHP VGTASMSPRGASWGVVDPDLKVKGVDGLRIVDGSILPFAP NAHTQGPIYLVGKQGADLIKADQ (SEQ ID NO: 9) |
| PeAAOMUT 2 | *Pleurotus eryngii* MUT2 | MSFGALRQLLLIACLALPSLAATNLPTADFDYVVVGAGNA GNVVAARLTEDPDVSVLVLEAGVSDENVLGAEAPLLAPGL VPNSIFDWNYTTTAQAGYNGRSIAYPRGRMLGGSSSVHYM VMMRGSTEDFDRYAAVTGDEGWNWDNIQQFVRKNEMV VPPADNHNTSGEFIPAVHGTNGSVSISLPGFPTPLDDRVLAT TQEQSEEFFFNPDMGTGHPLGISWSIASVGNGQRSSSSTAY LRPAQSRPNLSVLINAQVTKLVNSGTTNGLPAFRCVEYAEQ EGAPTTTVCAKKEVVLSAGSVGTPILLQLSGIGDENDLSSV GIDTIVNNPSVGRNLSDHLLLPAAFFVNSNQTFDNIFRDSSE FNVDLDQWTNTRTGPLTALIANHLAWLRLPSNSSIFQTFPD PAAGPNSAHWETIFSNQWFHPAIPRPDTGSFMSVTNALISP VARGDIKLATSNPFDKPLINPQYLSTEFDIFTMIQAVKSNLR FLSGQAWADFVIRPFDPRLRDPTDDAAIESYIRDNANTMW HPVGTASMSPRGASWGVVDPDLKVKGVDGLRIVDGSILPF APNAHTQGPIYLVGKQGADLIKADQ (SEQ ID NO: 10) |
| MtAAOx | *Thermothelomyces thermophilus* | MGFLAATLVSCAALASAASIPRPHAKRQVSQLRDDYDFVI VGGGTSGLTVADRLTEAFPAKNVLVIEYGDVHYAPGTFDP PTDWITPQPDAPPSWSFNSLPNPDMANTTAFVLAGQVVGG SSAVNGMFFDRASRHDYDAWTAVGGSGFEQSSHKWDWE GLFPFFQKSVTFTEPPADIVQKYHYTWDLSAYGNGSTPIYS SYPVFQWADQPLLNQAWQEMGINPVTECAGGDKEGVCW VPASQHPVTARRSHAGLGHYADVLPRANYDLLVQHQVVR VVFPNGPSHGPPLVEARSLADNHLFNVTVKGEVIISAGALH TPTVLQRSGIGPASFLDDAGIPVTLDLPGVGANLQDHCGPP VTWNYTEPYTGFFPLPSEMVNNATFKAEAITGFDEVPARG PYTLAGGNNAIFVSLPHLTADYGAITAKIRAMVADGTAAS YLAADVRTIPGMVAGYEAQLLVLADLLDNPEAPSLETPWA TSEAPQTSSVLAFLLHPLSRGSVRLNLSDPLAQPVLDYRSG |

TABLE 1-continued

4-HMF oxidases enzymes

| Name | Organism | Sequence |
|---|---|---|
| | | SNPVDIDLHLAHVRFLRGLLDTPTMQARGALETAPGSAVA DSDEALGEYVRSHSTLSFMHPCCTAAMLPEDRGGVVGPDL KVHGAEGLRVVDMSVMPLLPGAHLSATAYAVGEKAADIII QEWMDKEQ (SEQ ID NO: 11) |
| MtGLOx | Thermothelomyces thermophilus | MRASPSSRTLLASLALSSLPLSFGQLSIPTDLPDSWEYQGCY TDVPGRTINSASYADGTNMTNAACLSYCASKGFPYAGTEY SVECFCGTTLASSSAKVADSECNMPCSGAPSEPCGAGSRLS LFHSSAVTGPAANPGVNDFTHLGCYAEGKTGRALTYNPGL PGADMTVAKCTAACRAANYILAGVEYGGECYCGNTIANG GAPADSGCSMVCNGNSTEFCGGPDRLNVYSYKNQYEPTA TSTTGAGSTSSSSVPSATGLPEGWSYQGCWIDGKQGRILPY QLPDSQTNSRAACANACAEAGYTVSGTEYAVQCFCGDAIH NGGVETDEADCSTPCPGAPGEKCGAGDRLSIVSRGPPKIYA PPAPIEKIGDWEYQGCAEDNINDKRTFFWQIFFNDIMTPEM CLDRCAEFGYHAAGLEYGQECYCGDPANMATHGATFRPE SECNVVCAGNSTAICGGLARLTTYFWIGTPFYSWDFPQDW RAGKYEFLVDGVNIPLITHETITGKVSFISKGATGPGNETGA YEFDPATLEFRELHIKTDVFCAASVTLPDKAGRQLNVGGW AGEATYGTRLYWPDGAPGVPGTHDWQENVNVLHLQAGR WYPSVLVLTNGSVMVVGGLIGSNDAATPSIEILPYTGTPPL YMDWLDRTHPNNLYPFLCILPGGGIFVQYWNEARILDPVT FDTVKTLPDAPGAPNDPKGGRTYPLEGTAVLLPQKYPYTD PLGVLICGGSTEGPGNALDNCVSIYPEADEPEWQIERMPSF RVMTCMAPLPDGTYLIANGALHGVAGFGLGVGPNLNALL YDPSKPLGSRITVAANTTIARMYHSEAITLLDGRVLISGSNP EDGVNPEEYRVEVFLPPYLLAGKPRPTFTLENRDWAHGQT GIPFTLGSPARNGDITATLLGSVASTHGNSMGARTLMPRVS CRGTSCTVDAPPTANICPPGWYQFFVLDGGIPAVGVYVRIG GDAGQIGNWPQAPDFSVPGV (SEQ ID NO: 12) |
| GAO | Fusarium graminearum | MKHLLTLALCFSSINAVAVTVPHKAVGTGIPEGSLQFLSLR ASAPIGSAISRNNWAVTCDSAQSGNECNKAIDGNKDTFWH TFYGANGDPKPPHTYTIDMKTTQNVNGLSMLPRQDGNQN GWIGRHEVYLSSDGTNWGSPVASGSWFADSTTKYSNFETR PARYVRLVAITEANGQPWTSIAEINVFQASSYTAPQPGLGR WGPTIDLPIVPAAAAIEPTSGRVLMWSSYRNDAFGGSPGGI TLTSSWDPSTGIVSDRTVTVTKHDMFCPGISMDGNGQIVVT GGNDAKKTSLYDSSSDSWIPGPDMQVARGYQSSATMSDG RVFTIGGSWSGGVFEKNGEVYSPSSKTWTSLPNAKVNPML TADKQGLYRSDNHAWLFGWKKGSVFQAGPSTAMNWYYT SGSGDVKSAGKRQSNRGVAPDAMCGNAVMYDAVKGKIL TFGGSPDYQDSDATTNAHIITLGEPGTSPNTVFASNGLYFA RTFHTSVVLPDGSTFITGGQRRGIPFEDSTPVFTPEIYVPEQD TFYKQNPNSIVRVYHSISLLLPDGRVFNGGGGLCGDCTTNH FDAQIFTPNYLYNSNGNLATRPKITRTSTQSVKVGGRITIST DSSISKASLIRYGTATHTVNTDQRRIPLTLTNNGGNSYSFQV PSDSGVALPGYWMLFVMNSAGVPSVASTIRVTQ (SEQ ID NO: 13) |
| PaoABC | Echerichia coli | MKAFTYERVNTPAEAALSAQRVPGAKFIAGGTNLLDLMK LEIETPTHLIDVNGLGLDKIEVTDAGGLRIGALVRNTDLVA HERVRRDYAVLSRALLAGASGQLRNQATTAGNLLQRTRC PYFYDTNQPCNKRLPGSGCAALEGFSRQHAVVGVSEACIA THPSDMAVAMRLLDAVVETITPEGKTRSITLADFYHPPGKT PHIETALLPGELIVAVTLPPPLGGKHIYRKVRDRASYTFALV SVAAIIQPDGSGRVALGGVAHKPWRIEAADAQLSQGAQAV YDALFASAHPTAENTFKLLLAKRTLASVLAEARAQA (SEQ ID NO: 14) |
| AaeUPO | Agrocybe aegerita | MKYFPLFPTLVFAARVVAFPAYASLAGLSQQELDAIIPTLE AREPGLPPGPLENSSAKLVNDEAHPWKPLRPGDIRGPCPGL NTLASHGYLPRNGVATPVQIINAVQEGLNFDNQAAVFATY AAHLVDGNLITDLLSIGRKTRLTGPDPPPPASVGGLNEHGT FEGDASMTRGDAFFGNNHDFNETLFEQLVDYSNRFGGGK YNLTVAGELRFKRIQDSIATNPNFSFVDFRFFTAYGETTFPA NLFVDGRRDDGQLDMDAARSFFQFSRMPDDFFRAPSPRSG TGVEVVIQAHPMQPGRNVGKINSYTVDPTSSDFSTPCLMY EKFVNITVKSLYPNPTVQLRKALNTNLDFFFQGVAAGCTQ VFPYGRD (SEQ ID NO: 15) |
| CPO | Culduriomyces fumago | MFSKVLPFVGAVAALPHSVRQEPGSGIGYPYDNNTLPYVA PGPTDSRAPCPALNALANHGYIPHDGRAISRETLQNAFLNH MGIANSVIELALTNAFVVCEYVTGSDCGDSLVNLTLLAEPH AFEHDHSFSRKDYKQGVANSNDFIDNRNFDAETFQTSLDV VAGKTHFDYADMNEIRLQRESLSNELDFPGWFTESKPIQN |

TABLE 1-continued

4-HMF oxidases enzymes

| Name | Organism | Sequence |
|------|----------|----------|
| | | VESGFIFALVSDFNLPDNDENPLVRIDWWKYWFTNESFPY<br>HLGWHPPSPAREIEFVTSASSAVLAASVTSTPSSLPSGAIGP<br>GAEAVPLSFASTMTPFLLATNAPYYAQDPTLGPNDKREAA<br>PAATTSMAVFKNPYLEAIGTQDIKNQQAYVSSKAAAMASA<br>MAANKARNL (SEQ ID NO: 16) |
| CalB | Pseudozyma antarctica | MKLLSLTGVAGVLATCVAATPLVKRLPSGSDPAFSQPKSV<br>LDAGLTCQGASPSSVSKPILLVPGTGTTGPQSFDSNWIPLST<br>QLGYTPCWISPPPFMLNDTQVNTEYMVNAITALYAG SGNN<br>KLPVLTWSQGGLVAQWGLTFFPSIRSKVDRLMAFAPDYKG<br>TVLAGPLDALAVSAPSVWQQTTGSALTTALRNAGGLTQIV<br>PTTNLYSATDEIVQPQVSNSPLDSSYLFNGKNVQAQAVCGP<br>LFVIDHAGSLTSQFSYVVGRSALRSTTGQARSADYGITDCN<br>PLPANDLTPEQKVAAAALLAPAAAAIVAGPKQNCEPDLMP<br>YARPFAVGKRTCSGIVTP (SEQ ID NO: 17) |
| Laccase | Trametes versicolor | MGLQRFSFFVTLALVARSLAAIGPVASLVVANAPVSPDDFL<br>RDAIVVNGVVPSPLITGKKGDRFQLNVVDTLTNHSMLKST<br>SIHWHGFFQAGTNWADGPAFVNQCPIASGHSFLYDFHVPD<br>QAGTFWYHSRLSTQYCDGLRGPFVVYDPKDPHASRYDVD<br>NESTVITLTDWYHTAARLGPRFPLGADATLINGLGRSASTP<br>TAALAVINVQHGKRYRLRLVSISCDPNYTFSIDGHNLTVIE<br>VDGINSQPLLVDSIQIFAAQRYSFVLNANQTVGNYWVRAN<br>PNFGTVGFAGGINSAILRYQGAPVAEPTTTQTPSVIPLIETNL<br>HPLARMPVPGSPTPGGVDKALNLAFNFNGTNFFINNASFTP<br>PTVPVLLQILSGAQTAQELLPAGSVYPLPAHSTIEITLPATAL<br>APGAPHPFHLHGHAFAVVRSAGSTTYNYNDPIFRDVVSTG<br>TPAAGDNVTIRFQTDNPGPWFLHCHIDFHLEAGFAIVFAED<br>VADVKAANPVPKAWSDLCPIYDGLSEANQ (SEQ ID NO: 18) |
| HRP | Armoracia rusticana | MHFSSSSTLFTCITLIPLVCLILHASLSDAQLTPTFYDNSCPN<br>VSNIVRDTIVNELRSDPRIAASILRLHFHDCFVNGCDASILL<br>DNTTSFRTEKDAFGNANSARGFPVIDRMKAAVESACPRTV<br>SCADLLTIAAQQSVTLAGGPSWRVPLGRRDSLQAFLDLAN<br>ANLPAPFFTLPQLKDSFRNVGLNRSSDLVALSGGHTFGKN<br>QCRFIMDRLYNFSNTGLPDPTLNTTYLQTLRGLCPLNGNLS<br>ALVDFDLRTPTIFDNKYYVNLEEQKGLIQSDQELFSSPNAT<br>DTIPLVRSFANSTQTFFNAFVEAMDRMGNITPLTGTQGQIR<br>LNCRVVNSNSLLHDMVEVVDFVSSM (SEQ ID NO: 19) |
| CATALASE | Bos taurus | MADNRDPASDQMKHWKEQRAAQKPDVLTTGGGNPVGD<br>KLNSLTVGPRGPLLVQDVVFTDEMAHFDRERIPERVVHAK<br>GAGAFGYFEVTHDITRYSKAKVFEHIGKRTPIAVRFSTVAG<br>ESGSADTVRDPRGFAVKFYTEDGNWDLVGNNTPIFFIRDA<br>LLFPSFIHSQKRNPQTHLKDPDMVWDFWSLRPESLHQVSFL<br>FSDRGIPDGHRHMNGYGSHTFKLVNANGEAVYCKFHYKT<br>DQGIKNLSVEDAARLAHEDPDYGLRDLFNAIATGNYPSWT<br>LYIQVMTFSEAEIFPFNPFDLTKVWPHGDYPLIPVGKLVLN<br>RNPVNYFAEVEQLAFDPSNMPPGIEPSPDKMLQGRLFAYP<br>DTHRHRLGPNYLQIPVNCPYRARVANYQRDGPMCMMDN<br>QGGAPNYYPNSFSAPEHQPSALEHRTHFSGDVQRFNSAND<br>DNVTQVRTFYLKVLNEEQRKRLCENIAGHLKDAQLFIQKK<br>AVKNFSDVHPEYGSRIQALLDKYNEEKPKNAVHTYVQHG<br>SHLSAREKANL (SEQ ID NO: 20) |

In some embodiments, the conditions sufficient to convert 2,4-FDME to 2,4-FDCA comprise a reaction temperature of about 15° C. to about 25° C., about 25° C. to about 35° C., about 35° C. to about 45° C., about 45° C. to about 55° C., about 55° C. to about 65° C., about 65° C. to about 75° C., about 75° C. to about 85° C., about 85° C. to about 95° C., about 95° C. to about 105° C., about 105° C. to about 115° C., about 115° C. to about 125° C., about 125° C. to about 135° C., about 135° C. to about 145° C., about 145° C. to about 155° C., about 155° C. to about 165° C., about 165° C. to about 175° C., about 175° C. to about 185° C., about 185° C. to about 195° C., and/or about 195° C. to about 205° C.

In some embodiments, the conditions sufficient to convert 2,4-FDME to 2,4-FDCA comprise a reaction pH of about 3.5 to about 4, about 4 to about 4.5, about 4.5 to about 5, about 5 to about 5.5, about 5.5 to about 6, about 6 to about 6.5, about 6.5 to about 7, about 7 to about 7.5, about 7.5 to about 8, about 8 to about 8.5, and/or about 8.5 to about 9.

In some embodiments, the conditions sufficient to convert 2,4-FDME to 2,4-FDCA comprise a reaction pressure of about 101.3 kPa, about 90 kPa to about 110 kPa, about 110 kPa to about 130 kPa, about 130 kPa to about 150 kPa, and/or about 150 kPa to about 250 kPa.

In some embodiments, the conditions sufficient to convert 2,4-FDME to 2,4-FDCA comprise cell-free enzymatic oxidation. In some embodiments, the conditions sufficient to convert 2,4-FDME to 2,4-FDCA comprise whole-cell enzymatic oxidation. In some embodiments, the enzymes are isolated enzymes, whole broth enzymes, and/or immobilized enzymes.

In some embodiments, the conditions sufficient to convert 2,4-FDME to 2,4-FDCA comprise a suitable level of oxygen. In some embodiments, the conditions sufficient to convert 2,4-FDME to 2,4-FDCA comprise a level of oxygen of about 5 to 150 mmol 02 per liter per hour (mmol/L-h), such as about 20 mmol/L-h to about 60 mmol/L-h, about 5 mmol/L-h to about 10 mmol/L-h, about 10 mmol/L-h to about 20 mmol/L-h, about 20 mmol/L-h to about 30 mmol/L-h, about 30 mmol/L-h to about 40 mmol/L-h, about 40 mmol/L-h to about 50 mmol/L-h, about 50 mmol/L-h to about 60 mmol/L-h, about 60 mmol/L-h to about 70 mmol/L-h, about 70 mmol/L-h to about 80 mmol/L-h, about 80 mmol/L-h to about 90 mmol/L-h, about 90 mmol/L-h to about 100 mmol/L-h, about 100 mmol/L-h to about 110 mmol/L-h, about 110 mmol/L-h to about 120 mmol/L-h, about 120 mmol/L-h to about 130 mmol/L-h, about 130 mmol/L-h to about 140 mmol/L-h, and/or about 140 mmol/L-h to about 150 mmol/L-h.

In some embodiments, enzymatically converting 2,4-FDME to 2,4-FDCA is performed in a vessel substantially free of microorganisms. In some embodiments, enzymatically converting 2,4-FDME to 2,4-FDCA is performed by a microorganism. In some embodiments, the method is carried out in a stirred tank reactor, a packed bed reactor, or a tank with an external recirculation loop.

In some embodiments, the method of converting 2,4-FDME to 2,4-FDCA further comprises converting $H_2O_2$ to oxygen and water with a catalase, peroxidase, and/or peroxygenase. In some embodiments, the catalase or peroxidase is classified as EC number 1.11.1.-, and/or the peroxygenase is classified as EC number 1.11.2.-.

In some embodiments, the produced 2,4-FDCA is recovered from the conversion process in a substantially pure form by acid precipitation, solvent extraction, and/or cooling crystallization. In some embodiments, the produced 2,4-FDCA is recovered from the conversion process in an acid or salt form by acid precipitation, solvent extraction, and/or cooling crystallization.

EXAMPLES

Example 1: 2,4-FDME Pathway Expression in Glycerol-Null Yeast Strain

This example demonstrates the construction of a glycerol-null yeast strain and a glycerol-null yeast strain expressing a 2,4-FDME pathway. The strains were constructed using FY23 (haploid and isogenic to *Saccharomyces cerevisiae* S288C) as the host strain and their detailed information is listed in Table 2. Strains representing the step-wise creation of both strains are also listed in Table 2.

Strain 1d was obtained by deleting the GPD1 gene from strain FY23 by homologous recombination using construct 1 (FIG. 5A). Construct 1 was synthesized by GenScript and cloned in EcoRI and SphI restriction sites of a pUC57 commercial vector. Linear construct 1 was obtained from the pUC57 vector using the MssI restriction enzyme and used in yeast transformation.

Strain 1d2d was obtained by deleting the GPD2 gene from strain 1 d by homologous recombination using construct 2 (FIG. 5B). Construct 2 was synthesized by GenScript and cloned in EcoRI and SphI restriction sites of a pUC57 commercial vector. Linear construct 2 was obtained from the pUC57 vector using the MssI restriction enzyme and used in yeast transformation. The deletion of both GPD1 and GPD2 genes causes significantly decreased amounts of glycerol from sugar and strain 1d2d is considered a glycerol-null strain. As the glycerol-producing pathway allows cells to oxidize NADH, the glycerol-null strain 1d2d is not able to grow under anaerobic conditions (Bjorkqvist, S., et al. "Physiological response to anaerobicity of glycerol-3-phosphate dehydrogenase mutants of *Saccharomyces cerevisiae*", Applied and Environmental Microbiology 63.1 (1997): 128-32.).

Strain 1 is was obtained by replacing the GPD1 gene of the strain FY23 for the transcriptional unit containing MfnB1 gene through homologous recombination, using construct 3 (FIG. 5C). Construct 3 was synthesized by GenScript and cloned in EcoRI and SphI restriction sites of a pUC57 commercial vector. Linear construct 3 was obtained from the pUC57 vector using the MssI restriction enzyme and used in yeast transformation.

Strain 1 is 3 was obtained by replacing GPD2 gene of the strain 1 is for the transcriptional units containing MfnB1 and ADH1 mut genes through homologous recombination, using construct 5 (FIG. 5D). Construct 5 was synthesized by GenScript and cloned in EcoRI and SphI restriction sites of a pUC57 commercial vector. Linear construct 5 was released from the pUC57 vector using the MssI restriction enzyme prior to yeast transformation. The replacement of both GPD1 and GPD2 genes causes significantly decreased amounts of glycerol from sugar and strain 1 is 3 is considered a glycerol-null strain.

All DNA-mediated transformation into *S. cerevisiae* was conducted using the Lithium Acetate procedure as described by Gietz and Woods (2002) and in all cases integration of the constructs was confirmed by PCR amplification and sequencing of genomic DNA (Gietz, R. D.; Woods, R. A. "Transformation of yeast by lithium acetate/single-stranded carrier DNA/polyethylene glycol method", Methods in Enzymology 350 (2002): 87-96).

TABLE 2

Strains of *Saccharomyces cerevisiae* used in this study and their relevant genotype.

| Strain | Genotype |
| --- | --- |
| FY23 | MATa ura3-52 trp1Δ63 leu2Δ1 GAL2+ |
| 1d | MATa ura3-52 trp1Δ63 leu2Δ1 GAL2+ gpd1Δ::Construct 1 |
| 1d2d | MATa ura3-52 trp1Δ63 leu2Δ1 GAL2+ gpd1Δ::Construct 1 gpd2Δ::Construct 2 |
| 1is | MATa ura3-52 trp1Δ63 leu2Δ1 GAL2+ gpd1Δ::Construct 3 |
| 1is3 | MATa ura3-52 trp1Δ63 leu2Δ1 GAL2+ gpd1Δ::Construct 3 gpd2Δ::Construct 5 |

Example 2: Expression and Purification of 2,4-FDME Oxidase

The expression and purification of the enzyme used in enzymatic assays was carried out under the following conditions: Gene coding 2,4-FDME oxidase described in Table 3 was synthesized by GenScript and cloned in expression vector pET28a in NdeI and BamHI restriction sites. The expression vector was transformed into *E. coli* BL21 (DE3) and the transformant was stored in 15% glycerol until use for enzyme expression.

The stored transformant was inoculated in 30 mL of TB broth containing kanamycin at 37° C. with agitation for 16h to prepare a seed culture. The seed culture was added to 300 mL of TB broth containing kanamycin with initial OD (600 nm) of 0.2, the culture was then incubated at 37° C. with agitation until OD (600 nm) reached 0.8 at which point 1 mM IPTG was added to induce expression at 37° C. with agitation for 4 hours.

Figure 7:
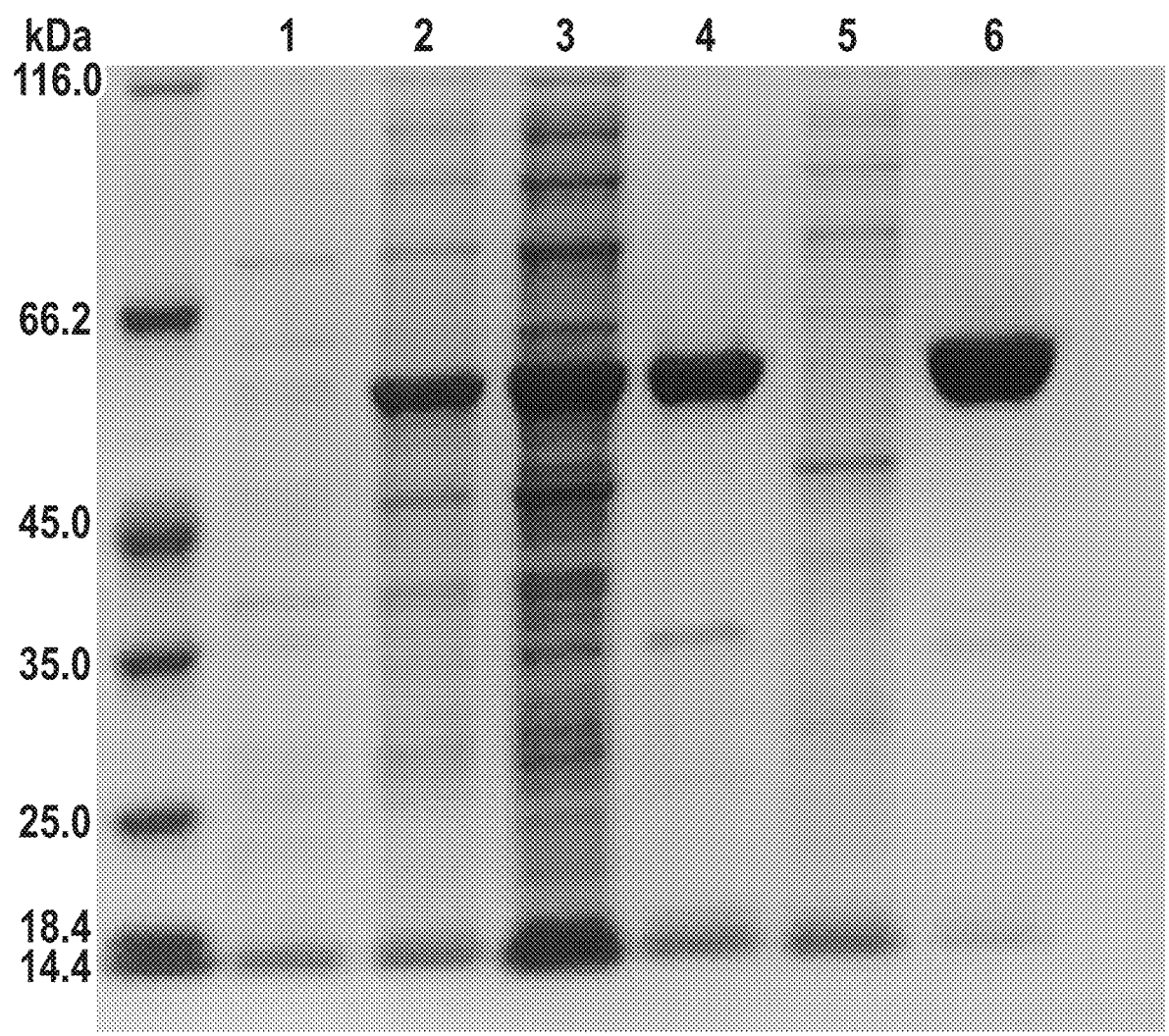
FIG. 7 is a representative SDS-PAGE image of the 2,4-FDME oxidase, HfmH1, in soluble phase after expression protocol (1), in insoluble phase (2), in soluble phase before purification (3), in buffer B after purification protocol (4), in flow through (5) and in potassium phosphate buffer after passage through PD10 column (6).

Following expression, the cells were centrifuged at 5000 rpm for 20 min and the pellet cell was suspended in cold lysis buffer (20 mM sodium phosphate buffer, 500 mM NaCl, 20 mM imidazole, 1 mM PMSF and beta-mercaptoethanol, pH 7) before ultrasonic disruption. The cell lysate was centrifuged at 6500 rpm for 20 min at 4° C. and filtered before purification with affinity chromatography. The column utilized was a HisTrap HP 5 mL (GE Healthcare) for his-tagged protein purification. The purified protein was bound and washed in the column with binding buffer A (20 mM sodium phosphate buffer, 20 mM imidazole, 500 mM NaCl, 1 mM PMSF and beta-mercaptoethanol, pH 7) and eluted in a gradient of elution buffer B (20 mM sodium phosphate buffer, 500 mM imidazole, 500 mM NaCl, 1 mM PMSF and beta-mercaptoethanol, pH 7). Then using a PD-10 column the buffer was changed to a 100 mM potassium phosphate buffer pH 7. Candidate expression and purification was analyzed on 12% polyacrylamide gel by electrophoresis (FIG. 7).

and zinc sulphate, 400 µg/L. Amino acids were supplemented as 1.62 g/L of Yeast Synthetic Drop-out Medium Supplements—without leucine (Part No. Y1376) and 76 mg/L of L-leucine. Ergosterol (0.01 g/L) and Tween 80 (0.42 g/L) were supplemented as anaerobic growth factors.

The fermentation systems containing 100 mL of culture media and 1% inoculum ratio were incubated at 30° C. and 210 rpm for 117 hours. The main fermentation metabolites, including glycerol and ethanol, were quantified by HPLC-IR (Thermo Ultimate 3000) using Bio-Rad Aminex HPX-87H column (50° C., $H_2SO_4$ 5 mM at 1 mL/min, isocratic gradient mode). 2,4-FDME was identified by HPLC-DAD (Thermo Ultimate 3000) using Waters XBrigde C18 column (30° C., 25 mM sodium acetate buffer: methanol (93:7) at 1.4 mL/min, λ 225 nm).

Figure 6:
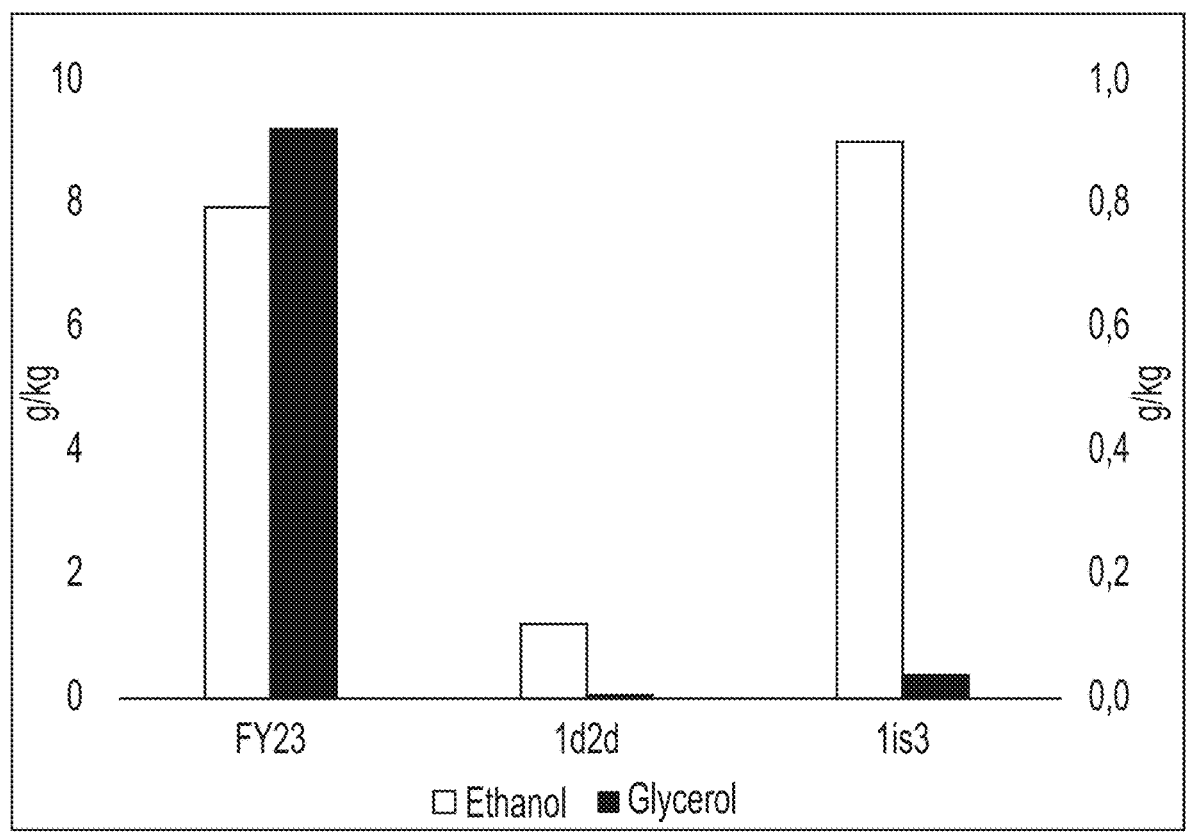
FIG. 6 is a graph showing average ethanol and glycerol production over a 117h fermentation under anaerobic conditions. Ethanol concentration is represented on the right x-axis and glycerol concentration is represented on left x-axis.

Results in FIG. 6 demonstrated that strain 1 is 3, expressing 2,4-FDME pathway, was able to exhaust the carbon source and produce ethanol at titers similar to FY23, the positive control strain. Moreover, strain 1 is 3 presented a significant reduction on glycerol production, analogous to the marginal glycerol production quantified for 1d2d, the negative control strain.

TABLE 3

2,4-FDME oxidase enzyme.

| Name | Organism | Sequence |
| --- | --- | --- |
| HmfH1 | Methylovorus sp. MUT | MTDTIFDYVIVGGGTAGSVLANRLSARPENRVLLIEAGI DTPENNIPPEIHDGLRPWLPRLSGDKFFWPNLTVYRAAE HPGITREPQFYEQGRLLGGGSSVNMVVSNRGLPRDYDE WQALGADGWDWQGVLPYFIKTERDADYGDDPLHGNA GPIPIGRVDSRHWSDFTVAATQALEAAGLPNIHDQNAR FDDGYFPPAFTLKGEERFSAARGYLDASVRVRPNLSLW TESRVLKLLTTGNAITGVSVLRGRETLQVQAREVILTAG ALQSPAILLRTGIGPAADLHALGIPVLADRPGVGRNLWE HSSIGVVAPLTEQARADASTGKAGSRHQLGIRASSGVD PATPSDLFLHIHADPVSGLASARFWVNKPSSTGWLKLK DADPFSYPDVDFNLLSDPRDLGRLKAGLRLIKHYFAYP SLAKYGLALALSRFEAPQPGGPLLNDLLQDEAALERYL RTNVGGVFHASGTARIGRADDSQAVVDKAGRVYGVT GLRVADASIMPTVPTANTNLPTLMLAEKIADAILTQA (SEQ ID NO: 21) |

Example 3: Anaerobic Co-Production of 2,4-FDME and Ethanol

Strains FY23, 1d2d and 1 is 3 described in Example 1 above were used to demonstrate the co-production of 2,4-FDME and ethanol under anaerobic conditions.

Precultures were prepared by inoculating a single colony of each strain in YP (Yeast Extract Peptone) medium with addition of 2% w/w glucose, at 30° C. and 210 rpm. After 18 hours of incubation, cells were harvested by centrifugation and washed with synthetic fermentation medium.

Anaerobic fermentation was carried out in 250 mL screw cap flasks equipped with ports for aseptic sampling and nitrogen injection. Oxygen permeation was mitigated by using norprene tubing and by injection of high purity nitrogen (<0.5 ppm oxygen) after inoculation and sampling. Synthetic fermentation medium comprised $(NH_4)_2SO_4$, 5.0 g/L, $CaCl_2$, 0.1 g/L, NaCl, 0.1 g/L, $MgSO_4$, 0.5 g/L, $KH_2PO_4$, 1.0 g/L, biotin, 2.0 µg/L, calcium pantothenate, 400 µg/L, folic acid, 2.0 µg/L, inositol, 2.0 mg/L, nicotinic acid, 400 µg/L, p-aminobenzoic acid, 200 µg/L, pyridoxine HCl, 400 µg/L, riboflavin, 200 µg/L, thiamine HCl, 400 µg/L, boric acid, 500 µg/L, copper sulphate, 40 mg/L, potassium iodide, 100 µg/L, ferric chloride, 200 µg/L, manganese sulphate, 400 µg/L, sodium molybdate, 200 µg/L, Importantly, as shown in Table 4, 2,4-FDME was not detected for both positive (FY23) and negative (1d2d) control strains. On the other hand, 2,4-FDME production was identified for strain 1 is 3, indicating that the strain was able to produce ethanol and 2,4-FDME under the anaerobic conditions described above.

This example thus demonstrated that a glycerol-null yeast strain expressing 2,4-FDME pathway was able to successfully co-produce 2,4-FDME and ethanol under the assayed anaerobic conditions.

TABLE 4

Average reported peak area for 2,4-FDME on fermentative samples over 117 h fermentation under anaerobic conditions.

| Strain | 2,4-FDME (mAU*min) |
| --- | --- |
| FY23 | n.d. |
| 1d2d | n.d. |
| 1is3 | 2.076 |

Peaks not detected at λ 225 nm were indicated as "n.d.".

Example 4: Production of 2,4-FDCA From 2,4-FDME by HMFH Oxidase

The 2,4-FDCA production from 2,4-FDME by the enzyme candidate described in Table 3 was demonstrated in vitro by incubating approximately 400 μg of purified 2,4-FDME oxidase candidate with a 1 mL solution containing 10 mM 2,4-FDME in 100 mM potassium phosphate buffer pH 7. 2,4-FDME samples were purchased from Olib Organic Libraries (Campinas-SP, Brazil). Reaction vessels without oxidase or 2,4-FDME were used as negative controls. The reactions were incubated at 30° C. for 24 hours and final samples analyzed by HPLC-DAD. All reactions were performed in triplicate.

The quantitative analysis of 2,4-FDME and the intermediate 2,4-HMF were performed using HPLC-DAD (Thermo Ultimate 3000) equipped with an XBridge C18 (Waters). The column was maintained at 30° C. The mobile phase used was a 25 mM sodium acetate: methanol (93:7 v/v) pH 6.0 solution with flow rate of 1.4 mL/min and isocratic gradient mode. 2,4-FDME was detected at 225 nm and 2,4-HMF was detected at 256 nm. 2,4-FDME and 2,4-HMF standard samples were purchased from Olib Organic Libraries (Campinas-SP, Brazil)

The quantitative analysis of 2,4-FDCA was performed using HPLC-DAD (Thermo Ultimate 3000) equipped with an Aminex HPX-87H (Bio-Rad). The column was maintained at 50° C. The mobile phase used was a 5 mM $H_2SO_4$ solution with flow rate of 0.75 mL/min and isocratic gradient mode. The molecule was detected at 245 nm. 2,4-FDCA standard samples was purchased from Uorsy (Kyiv, Ukraine).

Figure 8:
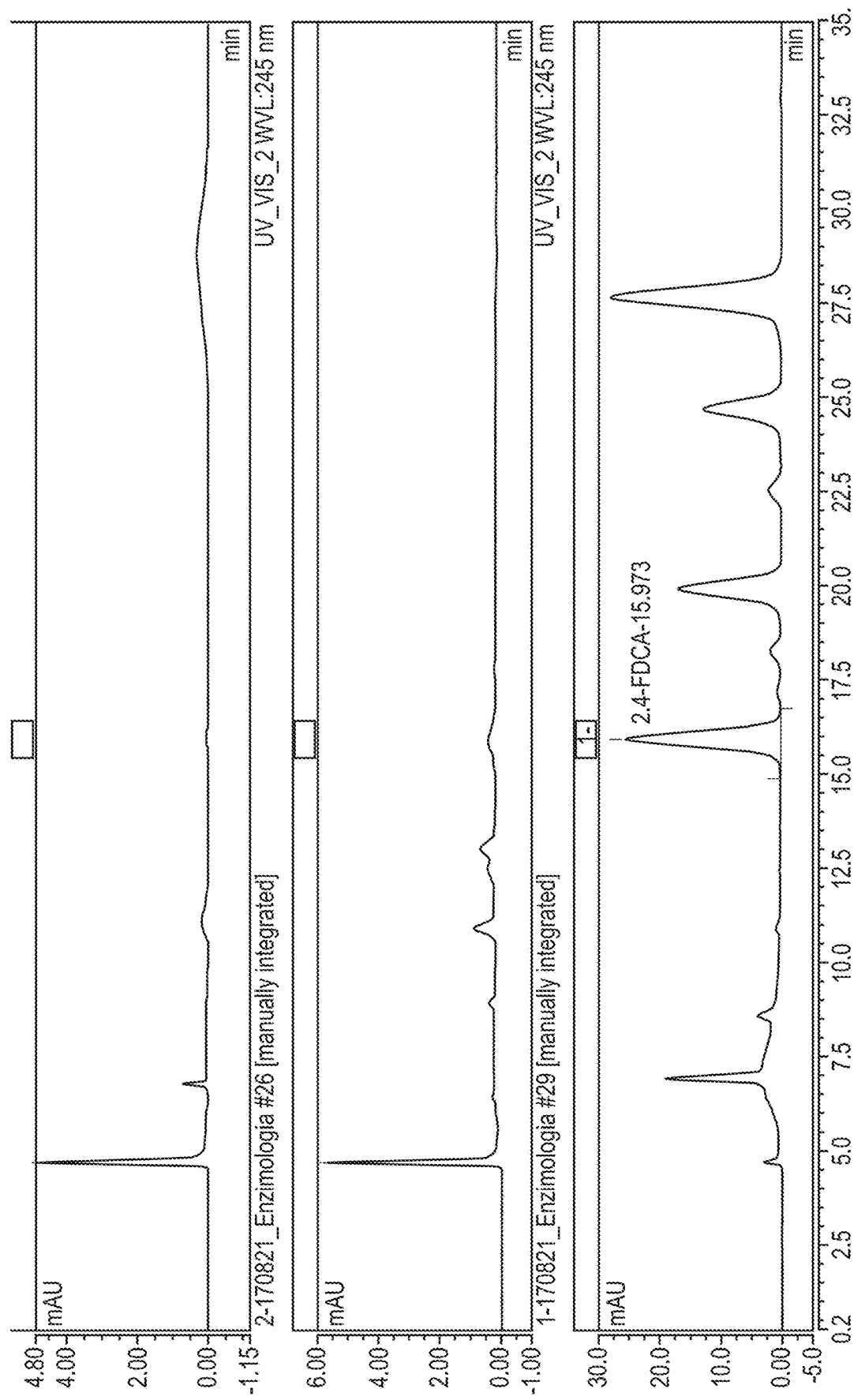
FIG. 8 is a representative UV spectra showing 2,4-FDCA production from 2,4-FDME by 2,4-FDME oxidase HfmH1 after 24 hours incubation (lower panel), negative control without HmfH1 (middle panel) and negative control without 2,4-FDME (upper panel). The chromatographic separation was performed using HPLC-DAD and 2,4-FDCA was detected at 245 nm.

As shown in Table 5 and FIG. 8, the conversion of 2,4-FDME into 2,4-FDCA was successfully demonstrated by 2,4-FDME oxidase HmfH1.

TABLE 5

| 2,4-FDCA production from 2,4-FDME with HmfH1 oxidase after 24 hours incubation. | | | |
|---|---|---|---|
| Reaction condition | 2,4-FDME (mM) | 2,4-HMF (mM) | 2,4-FDCA (mM) |
| HmfH1 | 2.94 ± 0.2 | 3.04 ± 0.14 | 0.42 ± 0.05 |
| Negative control without HmfH1 | 9.51 ± 0.02 | ND | ND |
| Negative control without 2,4-FDME | ND | ND | ND |

Numbered Embodiments

Embodiment 1. A recombinant microorganism comprising:
(a) at least one endogenous and/or exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandimethanol (2,4-FDME) from 4-HMF; and
(d) at least one deletion of an enzyme in a glycerol-production pathway or at least one genetic modification that leads to a down-regulation of an enzyme in a glycerol-production pathway.

Embodiment 2. The recombinant microorganism of embodiment 1, wherein the polypeptide that catalyzes the production of 2,4-FDME from 4-HMF is a dehydrogenase, preferably wherein the dehydrogenase is classified as EC number 1.1.1.

Embodiment 3. The recombinant microorganism of embodiment 2, wherein the dehydrogenase is selected from alcohol dehydrogenases classified as EC number 1.1.1.1, alcohol dehydrogenases ($NADP^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*, preferably wherein the mutated alcohol dehydrogenase comprises one to six non-conservative amino acid substitution(s) at one or more of residues 59, 110, 117, 148, 152, or 295, more preferably wherein the mutated alcohol dehydrogenase comprises mutations S110P, L117S, and/or Y295C.

Embodiment 4. The recombinant microorganism of any one of embodiments 1 to 3, wherein the enzyme in the glycerol-production pathway is a glycerol-3-phosphate dehydrogenase, preferably wherein the glycerol-3-phosphate dehydrogenase is classified as EC number 1.1.1.8 or EC number 1.1.5.3.

Embodiment 5. The recombinant microorganism of embodiment 4, wherein a GPD1 gene, a GPD2 gene, or both are deleted from the microorganism or down-regulated in the microorganism.

Embodiment 6. The recombinant microorganism of any one of embodiments 1 to 3, wherein the enzyme in the glycerol-production pathway is a glycerol-3-phosphate phosphatase, preferably wherein the glycerol-3-phosphate phosphatase is classified as EC number 3.1.3.21.

Embodiment 7. The recombinant microorganism of any one of embodiments 1 to 3, wherein a GPD1 gene, a GPD2 gene, and a gene encoding a glycerol-3-phosphate phosphatase are deleted from the microorganism or down-regulated in the microorganism.

Embodiment 8. The recombinant microorganism of any one of embodiments 1 to 7, wherein the microorganism produces ethanol.

Embodiment 9. A recombinant microorganism comprising:
(a) at least one endogenous and/or exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandimethanol (2,4-FDME) from 4-HMF; and
(d) at least one endogenous and/or exogenous nucleic acid molecule encoding one or more polypeptides that catalyze the production of NADH and $CO_2$ from formate.

Embodiment 10. The recombinant microorganism of embodiment 9, wherein the polypeptide that catalyzes the production of 2,4-FDME from 4-HMF is a dehydrogenase, preferably wherein the dehydrogenase is classified as EC number 1.1.1.

Embodiment 11. The recombinant microorganism of embodiment 10, wherein the dehydrogenase is selected from alcohol dehydrogenases classified as EC number 1.1.1.1, alcohol dehydrogenases (NADP⁺) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*, preferably wherein the mutated alcohol dehydrogenase comprises one to six non-conservative amino acid substitution(s) at one or more of residues 59, 110, 117, 148, 152, or 295, more preferably wherein the mutated alcohol dehydrogenase comprises mutations S110P, L117S, and/or Y295C.

Embodiment 12. The recombinant microorganism of any one of embodiments 9 to 11, wherein the polypeptide that catalyzes the production of NADH and $CO_2$ from formate is a $NAD^+$-dependent formate dehydrogenase, preferably wherein the $NAD^+$-dependent formate dehydrogenase is classified as EC number 1.2.1.2.

Embodiment 13. The recombinant microorganism of any one of embodiments 9 to 12, wherein the microorganism converts externally provided formate to NADH and $CO_2$.

Embodiment 14. The recombinant microorganism of any one of embodiments 9 to 13, further comprising at least one deletion of an enzyme in a glycerol-production pathway or at least one genetic modification that leads to a down-regulation of an enzyme in a glycerol-production pathway.

Embodiment 15. The recombinant microorganism of embodiment 14, wherein the enzyme in the glycerol-production pathway is a glycerol-3-phosphate dehydrogenase, preferably wherein the glycerol-3-phosphate dehydrogenase is classified as EC number 1.1.1.8 or EC number 1.1.5.3.

Embodiment 16. The recombinant microorganism of embodiment 15, wherein a GPD1 gene, a GPD2 gene, or both are deleted from the microorganism or down-regulated in the microorganism.

Embodiment 17. The recombinant microorganism of embodiment 14, wherein the enzyme in the glycerol-production pathway is a glycerol-3-phosphate phosphatase, preferably wherein the glycerol-3-phosphate phosphatase is classified as EC number 3.1.3.21.

Embodiment 18. The recombinant microorganism of any one of embodiments 9 to 14, wherein a GPD1 gene, a GPD2 gene, and a gene encoding a glycerol-3-phosphate phosphatase are deleted from the microorganism or down-regulated in the microorganism.

Embodiment 19. The recombinant microorganism of any one of embodiments 9 to 18 wherein the microorganism produces ethanol.

Embodiment 20. A recombinant microorganism comprising:
(a) at least one endogenous and/or exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandimethanol (2,4-FDME) from 4-HMF;
(d) at least one endogenous and/or exogenous nucleic acid molecule encoding a polypeptide that catalyzes the production of oxaloacetate from phosphoenol pyruvate (PEP);
(e) at least one endogenous and/or exogenous nucleic acid molecule encoding one or more polypeptides that catalyze:
  (1) the production of malonate semialdehyde from oxaloacetate; and/or
  (2) the production of aspartate from oxaloacetate, the production of β-alanine from aspartate, and the production of malonate semialdehyde from β-alanine; and/or
  (3) the production of malonyl-CoA from malonate semialdehyde; and/or
  (4) the production of malonyl-CoA from oxaloacetate; and/or
(f) at least one endogenous and/or exogenous nucleic acid molecule encoding one or more polypeptides that catalyze:
  (1) the production of acetyl-CoA from malonate semialdehyde, and the production of acetoacetyl-CoA from acetyl-CoA; and/or
  (2) the production of acetyl-CoA from malonyl-CoA, and the production of acetoacetyl-CoA from acetyl-CoA; and/or
  (3) the production of acetoacetyl-CoA from malonyl-CoA; and/or
(g) at least one endogenous and/or exogenous nucleic acid molecule encoding one or more polypeptides that catalyze:
  (1) the production of acetoacetate from acetoacetyl-CoA; and/or
  (2) the production of HMG-CoA from acetoacetyl-CoA, and the production of acetoacetate from HMG-CoA; and
(h) at least one endogenous and/or exogenous nucleic acid molecule encoding a polypeptide that catalyzes the production of acetone from acetoacetate.

Embodiment 21. The recombinant microorganism of embodiment 20, wherein the polypeptide that catalyzes the production of 2,4-FDME from 4-HMF is a dehydrogenase, preferably wherein the dehydrogenase is classified as EC number 1.1.1.

Embodiment 22. The recombinant microorganism of embodiment 21, wherein the dehydrogenase is selected from alcohol dehydrogenases classified as EC number 1.1.1.1, alcohol dehydrogenases (NADP⁺) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*, preferably wherein the mutated alcohol dehydrogenase comprises one to six non-conservative amino acid substitution(s) at one or more of residues 59, 110, 117, 148, 152, or 295, more preferably wherein the mutated alcohol dehydrogenase comprises mutations S110P, L117S, and/or Y295C.

Embodiment 23. The recombinant microorganism of any one of embodiments 20 to 22, wherein the polypeptide that catalyzes the production of malonate semialdehyde from oxaloacetate is an oxaloacetate 1-decarboxylase (MSA forming).

Embodiment 24. The recombinant microorganism of any one of embodiments 20 to 23, wherein the polypeptide that catalyzes the production of aspartate from oxaloacetate is an aspartate amino transferase.

Embodiment 25. The recombinant microorganism of any one of embodiments 20 to 24, wherein the polypeptide that catalyzes the production of β-alanine from aspartate is an aspartate decarboxylase.

Embodiment 26. The recombinant microorganism of any one of embodiments 20 to 25, wherein the polypeptide that catalyzes the production of malonate semialdehyde from β-alanine is a β-alanine pyruvate amino transferase and/or a β-alanine transaminase.

Embodiment 27. The recombinant microorganism of any one of embodiments 20 to 26, wherein the polypeptide that catalyzes the production of malonyl-CoA from malonate semialdehyde is a malonyl-CoA reductase and/or 2-keto acid decarboxylase.

Embodiment 28. The recombinant microorganism of any one of embodiments 20 to 27, wherein the polypeptide that catalyzes the production of malonyl-CoA from oxaloacetate is a malonyl-CoA synthetase.

Embodiment 29. The recombinant microorganism of any one of embodiments 20 to 28, wherein the polypeptide that catalyzes the production of acetyl-CoA from malonate semialdehyde is a malonate semialdehyde dehydrogenase.

Embodiment 30. The recombinant microorganism of any one of embodiments 20 to 29, wherein the polypeptide that catalyzes the production of acetoacetyl-CoA from acetyl-CoA is a thiolase and/or an acetyl-CoA acetyltransferase.

Embodiment 31. The recombinant microorganism of any one of embodiments 20 to 30, wherein the polypeptide that catalyzes the production of acetyl-CoA from malonyl-CoA is a malonyl-CoA decarboxylase.

Embodiment 32. The recombinant microorganism of any one of embodiments 20 to 31, wherein the polypeptide that catalyzes the production of acetoacetyl-CoA from malonyl-CoA is an acetoacetyl-CoA synthase.

Embodiment 33. The recombinant microorganism of any one of embodiments 20 to 32, wherein the polypeptide that catalyzes the production of acetoacetate from acetoacetyl-CoA is an acetoacetyl-CoA thioesterase and/or an acetoacetyl-CoA transferase.

Embodiment 34. The recombinant microorganism of any one of embodiments 20 to 33, wherein the polypeptide that catalyzes the production of HMG-CoA from acetoacetyl-CoA is a hydroxymethylglutaryl-CoA synthase.

Embodiment 35. The recombinant microorganism of any one of embodiments 20 to 34, wherein the polypeptide that catalyzes the production of acetoacetate from HMG-CoA is a hydroxymethylglutaryl-CoA lyase.

Embodiment 36. The recombinant microorganism of any one of embodiments 20 to 35, wherein the polypeptide that catalyzes the production of acetone from acetoacetate is an acetoacetate decarboxylase.

Embodiment 37. The recombinant microorganism of any one of embodiments 20 to 36, further comprising at least one endogenous and/or exogenous nucleic acid molecule encoding one or more polypeptides that catalyze the production of isopropanol from acetone.

Embodiment 38. The recombinant microorganism of embodiment 37, wherein the polypeptide that catalyzes the production of isopropanol from acetone is an alcohol dehydrogenase.

Embodiment 39. The recombinant microorganism of any one of embodiments 20 to 38 wherein the microorganism produces ethanol.

Embodiment 40. A recombinant microorganism comprising:
(a) at least one endogenous and/or exogenous nucleic acid molecule encoding a polypeptide that catalyzes the production of 4-hydroxymethylfurfural phosphate from glyceraldehyde 3-phosphate (G3P);
(b) at least one endogenous and/or exogenous nucleic acid molecule encoding a polypeptide that catalyzes the production of 4-hydroxymethylfurfural (4-HMF) from 4-hydroxymethylfurfural phosphate;
(c) at least one endogenous and/or exogenous nucleic acid molecule encoding one or more polypeptides that catalyze the production of 2,4-furandimethanol (2,4-FDME) from 4-HMF;
(d) at least one endogenous and/or exogenous nucleic acid molecule encoding one or more polypeptides that catalyze the production of 6-phospho-D-gluconate and NADPH from D-glucose-6-phosphate; and
(e) at least one endogenous and/or exogenous nucleic acid molecule encoding one or more polypeptides that catalyze the production of D-ribulose-5-phosphate, $CO_2$, and NADPH from 6-phospho-D-gluconate.

Embodiment 41. The recombinant microorganism of embodiment 40, wherein the polypeptide that catalyzes the production of 2,4-FDME from 4-HMF is a dehydrogenase, preferably wherein the dehydrogenase is classified as EC number 1.1.1.

Embodiment 42. The recombinant microorganism of embodiment 41, wherein the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*, preferably wherein the mutated alcohol dehydrogenase comprises one to six non-conservative amino acid substitution(s) at one or more of residues 59, 110, 117, 148, 152, or 295, more preferably wherein the mutated alcohol dehydrogenase comprises mutations S110P, L117S, and/or Y295C.

Embodiment 43. The recombinant microorganism of any one of embodiments 40 to 42, wherein the polypeptides that catalyze the production of 6-phospho-D-gluconate and NADPH from D-glucose-6-phosphate are a glucose-6-phosphate dehydrogenase and a gluconolactonase.

Embodiment 44. The recombinant microorganism of any one of embodiments 40 to 43, wherein the polypeptide that catalyzes the production of D-ribulose-5-phosphate, $CO_2$, and NADPH from 6-phospho-D-gluconate is a 6-phosphogluconate dehydrogenase.

Embodiment 45. The recombinant microorganism of any one of embodiments 40 to 44, further comprising at least one deletion of an enzyme in a pathway for converting fructose-6-phosphate and ATP to fructose-1,6-biphosphate, or at least one genetic modification that leads to a down-regulation of an enzyme in a pathway for converting fructose-6-phosphate and ATP to fructose-1,6-biphosphate.

Embodiment 46. The recombinant microorganism of embodiment 45, wherein the enzyme in the pathway for converting fructose-6-phosphate and ATP to fructose-1,6-biphosphate is a phosphofructokinase.

Embodiment 47. The recombinant microorganism of any one of embodiments 40 to 46, wherein the microorganism produces ethanol.

Embodiment 48. The recombinant microorganism of any one of the preceding embodiments, wherein the microorganism is selected from a bacterium, a fungus, or a yeast, preferably wherein the microorganism is a yeast, more preferably wherein the microorganism is *Saccharomyces cerevisiae*.

Embodiment 49. A method of co-producing 2,4-FDME and ethanol comprising: contacting the recombinant microorganism of any one of the preceding embodiments with a fermentable carbon source under conditions sufficient to produce 2,4-FDME and ethanol, optionally wherein the fermentable carbon source comprises formate.

Embodiment 50. The method of embodiment 49, wherein the recombinant microorganism further produces acetone.

Embodiment 51. The method of embodiment 49 or 50, wherein the recombinant microorganism further produces isopropanol.

Embodiment 52. The method of any one of embodiments 49 to 51, wherein the conditions comprise anaerobic conditions.

Embodiment 53. A method of producing 2,4-furandicarboxylic acid (2,4-FDCA), the method comprising: enzymatically converting 2,4-FDME to 2,4-FDCA with one or more oxidases, one or more laccases, one or more lipases, and/or one or more dehydrogenases, including combinations of oxidases, laccases, lipases, and/or dehydrogenases, either directly or through production of one or more intermediates selected from 5-(hydroxymethyl)-3-furaldehyde, 4-(hydroxymethyl)furfural, 5-(hydroxymethyl)furan-3-carboxylic acid, 2,4-furandicarbaldehyde, 4-(hydroxymethyl)-2-furancarboxylic acid, 5-formyl-3-furoic acid, or 4-formyl-2-furoic acid.

Embodiment 54. The method of embodiment 53, wherein the oxidase is classified as EC number 1.1.3.-, preferably wherein the oxidase is classified as EC number 1.1.3.47, EC number 1.1.3.7, EC number 1.1.3.9, and/or EC number 1.1.3.22.

Embodiment 55. The method of embodiment 53 or 54, wherein the laccase is classified as EC number 1.10.3.-.

Embodiment 56. The method of embodiment any one of embodiments 53 to 55, wherein the lipase is classified as EC number 3.1.1.-.

Embodiment 57. The method of embodiment any one of embodiments 53 to 56, wherein the dehydrogenase is classified as EC number 1.1.1.-, preferably wherein the dehydrogenase is classified as EC number 1.1.1.1.

Embodiment 58. The method of any one of embodiments 53 to 57, wherein enzymatically converting 2,4-FDME to 2,4-FDCA is performed in a vessel substantially free of microorganisms.

Embodiment 59. The method of any one of embodiments 53 to 57, wherein enzymatically converting 2,4-FDME to 2,4-FDCA is performed by a microorganism.

Embodiment 60. The method of any one of embodiments 53 to 59, further comprising converting $H_2O_2$ to oxygen and water with a catalase, peroxidase, and/or peroxygenase, preferably wherein the catalase or peroxidase is classified as EC number 1.11.1.-, and/or the peroxygenase is classified as EC number 1.11.2.-.

Embodiment 61. The method of any one of embodiments 53 to 60, wherein the 2,4-FDME is produced by the recombinant microorganism of any one of embodiments 1 to 48.

Embodiment 62. The method of any one of embodiments 53 to 60, wherein the 2,4-FDME is produced by the method of any one of embodiments 49 to 52.

The invention claimed is:

1. A recombinant microorganism that is an ethanol-producing yeast capable of producing 2,4-furandimethanol (2,4-FDME) and ethanol from a carbon source, wherein the recombinant microorganism expresses the following:
   (a) at least one exogenous nucleic acid molecule encoding a polypeptide that catalyzes the production of 4-hydroxymethylfurfural phosphate from glyceraldehyde 3-phosphate (G3P);
   (b) at least one endogenous and/or exogenous nucleic acid molecule encoding a polypeptide that catalyzes the production of 4-hydroxymethylfurfural (4-HMF) from 4-hydroxymethylfurfural phosphate;
   (c) at least one endogenous and/or exogenous nucleic acid molecule encoding one or more polypeptides that catalyze the production of 2,4-furandimethanol (2,4-FDME) from 4-HMF; and
   wherein the recombinant microorganism has at least one genetic modification that leads to a deletion or a down-regulation of an enzyme in a glycerol-production pathway in the microorganism and wherein 2,4-FDME production totally or partially replaces glycerol as co-product.

2. The recombinant microorganism of claim 1, wherein the polypeptide that catalyzes the production of 2,4-FDME from 4-HMF is a NADH-consuming dehydrogenase, wherein the dehydrogenase is selected from alcohol dehydrogenases classified as EC number 1.1.1.1, alcohol dehydrogenases (NADP$^+$) classified as EC number 1.1.1.2, D-xylose reductases classified as EC number 1.1.1.307, aryl-alcohol dehydrogenases classified as EC number 1.1.1.90, aryl-alcohol dehydrogenases classified as EC number 1.1.1.91, and/or a mutated alcohol dehydrogenase 1 from *Saccharomyces cerevisiae*.

3. The recombinant microorganism of claim 1, wherein the enzyme in the glycerol-production pathway is GPD1, GPD2, glycerol-3-phosphate phosphatase, or a combination thereof.

4. The recombinant microorganism of claim 1, wherein the microorganism further contains at least one endogenous and/or exogenous nucleic acid molecule encoding one or more polypeptides that catalyze the production of NADH and $CO_2$ from externally added formate.

5. The recombinant microorganism of claim 4 wherein the polypeptide that catalyzes the production of NADH and $CO_2$ from formate is a NAD$^+$-dependent formate dehydrogenase.

6. The recombinant microorganism of claim 1, wherein the microorganism further contains: (i) at least one endogenous and/or exogenous nucleic acid molecule encoding one or more polypeptides that catalyze the production of 6-phospho-D-gluconate and NADPH from D-glucose-6-phosphate; and (ii) at least one endogenous and/or exogenous nucleic acid molecule encoding one or more polypeptides that catalyze the production of D-ribulose-5-phosphate, $CO_2$, and NADPH from 6-phospho-D-gluconate.

7. The recombinant microorganism of claim 6, wherein the polypeptides that catalyze the production of 6-phospho-D-gluconate and NADPH from D-glucose-6-phosphate are a glucose-6-phosphate dehydrogenase and a gluconolactonase.

8. The recombinant microorganism of claim 6, wherein the polypeptide that catalyzes the production of D-ribulose-5-phosphate, $CO_2$, and NADPH from 6-phospho-D-gluconate is a 6-phosphogluconate dehydrogenase.

9. The recombinant microorganism of claim 6, wherein the polypeptide that catalyzes the NADPH-driven reduction of NAD(+) is a transhydrogenase.

10. The recombinant microorganism of claim 6, further comprising at least one deletion of a gene encoding an enzyme in a pathway for converting fructose-6-phosphate and ATP to fructose-1,6-biphosphate, or at least one genetic modification that leads to a down-regulation of an enzyme in a pathway for converting fructose-6-phosphate and ATP to fructose-1,6-biphosphate.

11. The recombinant microorganism of claim 10, wherein the enzyme in the pathway for converting fructose-6-phosphate and ATP to fructose-1,6-biphosphate is a phosphofructokinase.

12. The recombinant microorganism of claim 1, wherein the microorganism is selected from *Saccharomyces* spp., *Saccharomyces cerevisiae*, *Candida krusei*, *Issatchenkia* spp., *Issatchenkia orientalis*, *Hansenula* spp., *Debaryomyces* spp., *Rhodotula* spp., *Pachysolen* spp., *Cryptococcus* spp., *Trichosporon* spp., *Myxozyma* spp., *Candida* spp., *Kluyveromyces* spp., *Pichia* spp., *Pichia kudriavzevii*, *Schizosaccharomyces* spp., *Torulaspora* spp., *Zygosaccharomyces* spp., *Yarrowia* spp., *Yarrowia lipolytica*, *Scheffersomyces* spp., or *Scheffersomyces stipitis*.

13. A method of producing 2,4-FDME comprising: contacting the recombinant ethanol-producing yeast of claim 1 with a fermentable carbon source under conditions sufficient to produce 2,4-FDME and ethanol.

14. The method of producing 2,4-FDME of claim 13, wherein the fermentable carbon source comprises a hexose, a pentose, glycerol, $CO_2$, sucroses or combinations thereof.

15. The method of claim 13 wherein the fermentable carbon source further comprises formate as a co-substrate.

16. The method of claim 13, wherein the 2,4-FDME and ethanol are coproduced under anaerobic or microaerobic conditions.

17. A method of producing 2,4-furandicarboxylic acid (2,4-FDCA), the method comprising: (i) contacting the recombinant ethanol-producing yeast of claim 1 with a fermentable carbon source under conditions sufficient to produce 2,4-FDME and ethanol; and (ii) converting the 2,4-FDME to 2,4-FDCA.

18. The method of claim 17, wherein step (ii) comprises enzymatically converting the 2,4-FDME to 2,4-FDCA with one or more oxidases or oxidative enzymes.

19. The method of claim 17, wherein step (ii) comprises converting the 2,4-FDME to 2,4-FDCA by the same ethanol-producing yeast or by another microorganism in a vessel in presence of a sufficient amount of oxygen to convert the 2,4-FDME to 2,4-FDCA, wherein the microorganism express necessary amounts of the oxidative enzymes needed for 2,4-FDME oxidation into 2,4-FDCA.

20. The method of claim 18, wherein enzymatically converting the 2,4-FDME to 2,4-FDCA is performed in a vessel free of microorganisms and in presence of a sufficient amount of oxygen to enzymatically convert the 2,4-FDME to 2,4-FDCA.

21. The recombinant microorganism of claim 2, wherein the mutated alcohol dehydrogenase comprises one to six non-conservative amino acid substitution(s) at one or more of residues 59, 110, 117, 148, 152, or 295.

22. The recombinant microorganism of claim 21, wherein the mutated alcohol dehydrogenase comprises mutations S110P, L117S, and/or Y295C.

23. The recombinant microorganism of claim 5, wherein the NAD$^+$-dependent formate dehydrogenase is classified as EC number 1.2.1.2.

24. The method of claim 6, wherein the microorganism further contains at least one endogenous and/or exogenous nucleic acid molecule encoding one or more polypeptides that catalyze NADPH-driven reduction of NAD(+).

* * * * *